(12) United States Patent
Skinner et al.

(10) Patent No.: US 8,263,068 B2
(45) Date of Patent: Sep. 11, 2012

(54) MODIFIED CELLS EXPRESSING A PROTEIN THAT MODULATES ACTIVITY OF BHLH PROTEINS, AND USES THEREOF

(75) Inventors: Michael K. Skinner, Pullman, WA (US); Jaideep Chaudhary, Atlanta, WA (US)

(73) Assignee: Washington State University Research Foundation, Pullman, WA (US)

(*) Notice: Subject to any disclaimer, the term of this patent is extended or adjusted under 35 U.S.C. 154(b) by 657 days.

(21) Appl. No.: 11/587,888

(22) PCT Filed: Apr. 29, 2005

(86) PCT No.: PCT/US2005/014857
§ 371 (c)(1),
(2), (4) Date: Jun. 6, 2008

(87) PCT Pub. No.: WO2006/118564
PCT Pub. Date: Nov. 9, 2006

(65) Prior Publication Data
US 2008/0233089 A1 Sep. 25, 2008

Related U.S. Application Data

(60) Provisional application No. 60/566,685, filed on Apr. 29, 2004.

(51) Int. Cl.
| | |
|---|---|
| C12N 5/06 | (2006.01) |
| C12N 15/85 | (2006.01) |
| A61K 35/34 | (2006.01) |
| A61K 35/30 | (2006.01) |
| A61K 35/48 | (2006.01) |
| A61K 48/00 | (2006.01) |
| C12Q 1/68 | (2006.01) |
| A61P 41/00 | (2006.01) |

(52) U.S. Cl. ............ 424/93.21; 435/325; 435/347; 435/455; 435/375; 435/6

(58) Field of Classification Search .............. None
See application file for complete search history.

(56) References Cited

U.S. PATENT DOCUMENTS

| | | | |
|---|---|---|---|
| 4,822,470 A | 4/1989 | Chang | |
| 4,868,121 A | 9/1989 | Scharp et al. | |
| 4,955,378 A | 9/1990 | Grasso | |
| 5,273,904 A | 12/1993 | Langley | |
| 5,322,790 A | 6/1994 | Scharp et al. | |
| 5,447,863 A | 9/1995 | Langley | |
| 5,531,997 A | 7/1996 | Cochrum | |
| 5,620,883 A | 4/1997 | Shao et al. | |
| 5,702,700 A | 12/1997 | Sanberg et al. | |
| 5,725,854 A | 3/1998 | Selawry | |
| 5,759,534 A | 6/1998 | Selawry | |
| 5,821,121 A | 10/1998 | Brothers | |
| 5,827,736 A | 10/1998 | Heller et al. | |
| 5,830,460 A | 11/1998 | Sanberg et al. | |
| 5,849,285 A | 12/1998 | Selawry | |
| 5,958,404 A | 9/1999 | Selawry | |
| 6,001,643 A | 12/1999 | Spaulding | |
| 6,080,412 A | 6/2000 | Jordan et al. | |
| 6,214,334 B1 | 4/2001 | Lee et al. | |
| 6,262,255 B1 | 7/2001 | Mares-Guia | |
| 6,264,943 B1 | 7/2001 | Cherksey | |
| 6,303,355 B1 | 10/2001 | Opara | |
| 6,365,385 B1 | 4/2002 | Opara | |
| 2004/0098767 A1* | 5/2004 | Spangenberg et al. | 800/320 |

OTHER PUBLICATIONS

Gleichmann et al. (Journal of Neurochemistry. 2002; 80: 755-762).*
Chaudhary et al. (Endorinology. 2001; 142: 1727-1736).*
Morrow et al. (Molecular Immunology. 1999; 36: 491-503).*
Anway et al.(Biology of Reproduction. 2003; 68: 996-1002).*
Hsu et al. (Experimental Cell Research. 2004; 294: 185-198).*
Toma et al. (The Journal of Neuroscience. 2000; 20(20): 7648-7656).*
Visser et al. (Jounal of Virology. 1981; p. 684-693).*
Tanaka et al. (The Journal of Biological Chemistry. 1998; 273(40): 25922-25928).*
Pajalunga et al. (PLoS ONE 2010; 5(7): e11559, 1-12).*
Abel, Margaret H. et al., "The Effect of a Null Mutation in the Follicle-Stimulating Hormone Receptor Gene on Mouse Reproduction," *Endocrinology*, 2000, 141:1795-803 (Exhibit 24).
Alani, Rhoda M. et al., "Id1 regulation of cellular senescence through transcriptional repression of p16/Ink4a," *PNAS*, 2001, 98:7812-6 (Exhibit 25).
Alani, Rhoda M. et al., "Immortalization of primary human keratinocytes by the helix-loop-helix protein, Id-1," *Proc. Natl. Acad. Sci. USA*, 1999, 96:9637-41 (Exhibit 26).
Andreason, Grai L. and Glen A. Evans, "Introduction and Expression of DNA Molecules in Eukaryotic Cell by Electroporation," *BioTechniques*, 1988, 6:650-60 (Exhibit 27).
Anderson, W. French et al., "Replication and expression of thymidine kinase and human globin genes microinjected into mouse fibroblasts," *Proceedings of the National Academy of Sciences USA*, 1980, 77:5399-403 (Exhibit 28).
Anthony, Catherine Tananis et al., "Actions of the Testicular Paracrine Factor (P-Mod-S) on Sertoli Cell Transferrin Secretion Throughout Pubertal Development," *Endocrinology*, 1991, 129:353-60 (Exhibit 29).
Anway, Matthew D. et al., "Isolation of Sertoli Cells from Adult Rat Testes: An Approach to Ex Vivo Studies of Sertoli Cell Function," *Biology of Reproduction*, 2003,68:996-1002 (Exhibit 30).

(Continued)

Primary Examiner — Scott Long
(74) Attorney, Agent, or Firm — Adriano & Associates

(57) ABSTRACT

The present invention relates to modified cells carrying a heterologous gene sequence encoding a protein, such as an Inhibitor of differentiation (Id) gene sequence that binds a basic helix-loop-helix (bHLH) protein to inhibit cell growth, differentiation and/or tumorigenesis of the modified cells. The modified cells are differentiated, proliferate and do not become tumorigenic when grafted into a recipient subject. Additionally, the modified cells produce a factor or factors that enhance the viability of co-grafted organs, tissues or cells. Thus, the modified cells are useful for testing agents for effects on the cells, for co-grafting with transplant organs, tissues or cells. The modified cells are also useful for enhancing the viability of thawing cells that have been cryo-preserved. In one embodiment, the modified cells are modified Sertoli cells.

3 Claims, 7 Drawing Sheets

OTHER PUBLICATIONS

Aubin, Rémy J. et al., "Factors Influencing Efficiency and Reproducibility of Polybrene-Assisted Gene Transfer," *Somatic Cell and Molecular Genetics*, 1988, 14:155-67 (Exhibit 31).

Backlund, Erik-Olof et al., "Transplantation of adrenal medullary tissue to striatum in parkinsonism," *J. Neurosurg*, 1985, 62:169-73 (Exhibit 32).

Bain, Gretchen et al., "E2A and E2-2 Are Subunits of B-Cell-Specific E2-Box DNA-Binding Proteins," *Molecular and Cellular Biology*, 1993, 13:3522-9 (Exhibit 33).

Barone, M. Vittoria et al., "Id proteins control growth induction in mammalian cells," *Proc. Natl. Acad. Sci. USA*, 1994, 91:4985-8 (Exhibit 34).

Behr, Jean-Paul et al., "Efficient gene transfer into mammalian primary endocrine cells with lipopolyamine-coated DNA," *Proc. Natl. Acad. Sci. USA*, 1989, 86:6982-6 (Exhibit 35).

Benezra, Robert et al., "The Protein Id: A Negative Regulator of Helix-Loop-Helix DNA Binding Proteins," *Cell*, 1990, 61:49-59 (Exhibit 36).

Berkner, Kathleen L., "Development of Adenovirus Vectors for the Expression of Heterologous Genes," *Bio Techniques*, 1988, 6:616-29 (Exhibit 37).

Bitter, Grant A. et al., "Expression and Secretion Vectors for Yeast," *Methods in Enzymology*, 1987, 153:516-44 (Exhibit 38).

Björklund, Anders, "Dopaminergic transplants in experimental parkinsonism: cellular mechanisms of graft-induced functional recovery," *Current Opinion in Neurobiology*, 1992, 2:683-9 (Exhibit 39).

Boer, G. J. et al., "Vasopressin Neuron Survival in Neonatal Brattleboro Rats; Critical Factors in Graft Development and Innervation of the Host Brain," *Neuroscience*, 1985, 15:1087-109 (Exhibit 40).

Borlongan, Cesario V. et al., "Intracerebral Transplantation of Testis-Derived Sertoli Cells Promotes Functional Recovery in Female Rats with 6-Hydroxydopamine-Induced Hemiparkinsonism," *Experimental Neurology*, 1997, 148:388-92 (Exhibit 41).

Boshart, Michael et al., "A Very Strong Enhancer is Located Upstream of an Immediate Early Gene of Human Cytomegalovirus," *Cell*, 1985, 41:521-30 (Exhibit 42).

Bourdon, Véronique et al., "Characterization of a Clonal Sertoli Cell Line Using Adult PyLT Transgenic Mice," *Biology of Reproduction*, 1998, 58:591-9 (Exhibit 43).

Braun, Kirt W. et al., "Positive Regulation of Retinoic Acid Receptor Alpha by Protein Kinase C and Mitogen-Activated Protein Kinase in Sertoli Cells," *Biology of Reproduction*, 2002, 67:29-37 (Exhibit 44).

Bremner, William J. et al., "Immunohistochemical Localization of Androgen Receptors in the Rat Testis: Evidence for Stage-Dependent Expression and Regulation by Androgens," *Endocrinology*, 1994, 135:1227-34 (Exhibit 45).

Buzzard, Jeremy J. et al., "Thyroid Hormone, Retinoic Acid, and Testosterone Suppress Proliferation and Induce Markers of Differentiation in Cultured Rat Sertoli Cells," *Endocrinology*, 2003, 144:3722-31 (Exhibit 46).

Capecchi, Mario R., "High Efficiency Transformation by Direct Microinjection of DNA into Cultured Mammalian Cells," *Cell*, 1980, 22:479-88 (Exhibit 47).

Capel, Blanche et al., "Establishment and characterization of conditionally immortalized cells from the mouse urogenital ridge," *Journal of Cell Science*, 1996, 109:899-909 (Exhibit 48).

Chaudhary, Jaideep and Michael K. Skinner, "Comparative Sequence Analysis of the Mouse and Human Transferrin Promoters: Hormonal Regulation of the Transferrin Promoter in Sertoli Cells," *Molecular Reproduction and Development*, 1998, 50:273-83 (Exhibit 49).

Chaudhary, Jaideep and Michael K. Skinner, "Basic Helix-Loop-Helix Proteins Can Act at the E-Box within the Serum Response Element of the *c-fos* Promoter to Influence Hormone-Induced Promoter Activation in Sertoli Cells," *Molecular Endocrinology*, 1999, 13:774-86 (Exhibit 50).

Chaudhary, Jaideep and Michael K. Skinner, "The Basic Helix-Loop-Helix E2A Gene Product E47, Not E12, Is Present in Differentiating Sertoli Cells," *Molecular Reproduction and Development*, 1999, 52:1-8 (Exhibit 51).

Chaudhary, Jaideep and Michael K. Skinner, "Role of the Transcriptional Coactivator CBP/p300 in Linking Basic Helix-Loop-Helix and CREB Responses for Follicle-Stimulating Hormone-Mediated Activation of the Transferrin Promoter in Sertoli Cells," *Biology of Reproduction*, 2001, 65:568-74 (Exhibit 52).

Chaudhary, Jaideep et al., "Expression of the Basic Helix-Loop-Helix Protein REBα in Rat Testicular Sertoli Cells," *Biology of Reproduction*, 1999, 60:1244-50 (Exhibit 53).

Chaudhary, Jaideep et al., "Hormonal Regulation and Differential Actions of the Helix-Loop-Helix Transcriptional Inhibitors of Differentiation (Id1, Id2, Id3, and Id4) in Sertoli Cells," *Endocrinology*, 2001, 142:1727-36 (Exhibit 54).

Chaudhary, Jaideep et al., "Identification of a novel Sertoli cell gene product SERT that influences follicle stimulating hormone actions," *Gene*, 2004, 324:79-88 (Exhibit 55).

Chaudhary, Jaideep et al., "Role of Basic-Helix-Loop-Helix Transcription Factors in Sertoli Cell Differentiation: Identification of an E-Box Response Element in the Transferrin Promoter," *Endocrinology*, 1997, 138:667-75 (Exhibit 56).

Chaudhary, J. et al., "Role of Winged Helix Transcription Factor (WIN) in the Regulation of Sertoli Cell Differentiated Functions: WIN Acts as an Early Event Gene for Follicle-Stimulating Hormone," *Endocrinology*, 2000, 141:2758-66 (Exhibit 57).

Chen, Claudia A. and Hiroto Okayama, "Calcium Phosphate-Mediated Gene Transfer: A Highly Efficient Transfection System for Stably Transforming Cells with Plasmid DNA," *BioTechniques*, 1988, 6:632-8 (Exhibit 58).

Cheng, C. Yan and C. Wayne Bardin, "Identification of Two Testosterone-responsive Testicular Proteins in Sertoli Cell-enriched Culture Medium Whose Secretion is Suppressed by Cells of the Intact Seminiferous Tubule," *The Journal of Biological Chemistry*, 1987, 262:12768-79 (Exhibit 59).

Christy, Barbara A. et al., "An Id-related helix-loop-helix protein encoded by a growth factor-inducible gene," *Proc. Natl. Acad. Sci. USA*, 1991, 88:1815-9 (Exhibit 60).

Colbère-Garapin, Florence et al., "A New Dominant Hybrid Selective Marker for Higher Eukaryotic Cells," *Journal of Molecular Biology*, 1981, 150:1-14 (Exhibit 61).

Crépieux, Pascale et al., "The ERK-dependent signalling is stage-specifically modulated by FSH, during primary Sertoli cell maturation," *Oncogene*, 2001, 20:4696-709 (Exhibit 62).

Daggett, Melissa A. F. et al., "Expression of Steroidogenic Factor 1 in the Testis Requires an E Box and CCAAT Box in its Promoter Proximal Region," *Biology of Reproduction*, 2000, 62:670-9 (Exhibit 63).

Deed, Richard W. et al., "Nucleotide sequence of the cDNA encoding human helix-loop-helix Id-1 protein: identification of functionally conserved residues common to Id proteins," *Biochimica et Biophysica Acta*, 1994, 1219:160-2 (Exhibit 64).

Dunnett, Stephen B. et al., "Behavioural Recovery Following Transplantation of Substantia Nigra in Rats Subjected to 6-OHDA Lesions of the Nigrostriatal Pathway. I. Unilateral Lesions," *Brain Research*, 1981, 215:147-61 (Exhibit 65).

Dunnett, Stephen B. et al., "Behavioral Recovery Following Transplantation of Substantia Nigra in Rats Subjected to 6-OHDA Lesions of the Nigrostriatal Pathway. II. Bilateral Lesions," *Brain Research*, 1981, 229:457-70 (Exhibit 66).

Dutertre, Martin et al., "A mouse Sertoli cell line expressing anti-Müllerian hormone and its type II receptor," *Molecular and Cellular Endocrinology*, 1997, 136:57-65 (Exhibit 67).

Eckner, Richard et al., "Molecular cloning and functional analysis of the adenovirus E1A-associated 300-kD protein (p300) reveals a protein with properties of a transcriptional adaptor," *Genes & Development*, 1994, 8:869-84 (Exhibit 68).

Einarson, Margret B. and Moses V. Chao, "Regulation of Id1 and Its Association with Basic Helix-Loop-Helix Proteins during Nerve Growth Factor-Induced Differentiation of PC12 Cells," *Molecular and Cellular Biology*, 1995, 15:4175-83 (Exhibit 69).

European Mycophenolate Mofetil Cooperative Study Group, "Placebo-controlled study of mycophenolate mofetil combined with cyclosporin and corticosteroids for prevention of acute rejection," *The Lancet*, 1995, 345:1321-5 (Exhibit 70).

Field, Jane et al., "Improved Islet Isolation from Rat Pancreas Using 35% Bovine Serum Albumin in Combination with Dextran Gradient Separation," *Transplantation*, 1996, 61:1554-6 (Exhibit 71).

Fiers, W. et al., "Complete nucleotide sequence of SV40 DNA," *Nature*, 1978, 273:113-20 (Exhibit 72).

Fortini, Mark E. et al., "An activated Notch receptor blocks cell-fate commitment in the developing *Drosophila* eye," *Nature*, 1993, 365:555-7 (Exhibit 73).

Freed, William J. et al., "Restoration of Dopaminergic Function by Grafting of Fetal Rat Substantia Nigra to the Caudate Nucleus: Long-Term Behavioral, Biochemical, and Histochemical Studies," *Annals of Neurology*, 1980, 8:510-9 (Exhibit 74).

Freed, William J. et al., "Normalization of Spiroperidol Binding in the Denervated Rat Striatum by Homologous Grafts of Substantia Nigra," *Science*, 1983, 222:937-9 (Exhibit 75).

Fu, Weiming et al., "Telomerase Mediates the Cell Survival-Promoting Actions of Brain-Derived Neurotrophic Factor and Secreted Amyloid Precursor Protein in Developing Hippocampal Neurons," *The Journal of Neuroscience*, 2002, 22:10710-9 (Exhibit 76).

Gage, F. H. et al., "Grafting Genetically Modified Cells to the Brain: Possibilities for the Future," *Neuroscience*, 1987, 23:795-807 (Exhibit 77).

Gilboa, Eli et al., "Transfer and Expression of Cloned Genes Using Retoviral Vectors," *BioTechniques*, 1986, 4:504-12 (Exhibit 78).

Goetz, Tamara L. et al., "Role of E Box and Initiator Region in the Expression of the Rat Follicle-stimulating Hormone Receptor," *The Journal of Biological Chemistry*, 1996, 271:33317-24 (Exhibit 79).

Graessmann, A. et al., "Retransformation of a Simian Virus 40 Revertant Cell Line, Which is Resistant to Viral and DNA Infections, by Microinjection of Viral DNA," *Journal of Virology*, 1979, 32:989-94 (Exhibit 80).

Graham, F. L. and A. J. Van Der Eb, "A New Technique for the Assay of Infectivity of Human Adenovirus 5 DNA," *Virology*, 1973, 52:456-67 (Exhibit 81).

Griswold, Michael D., "Protein Secretions of Sertoli Cells," *International Review of Cytology*, 1988, 110:133-56 (Exhibit 82).

Grønning, Line M. et al., "Isoform-Specific Regulation of the CCAAT/Enhancer-Binding Protein Family of Transcription Factors by 3',5'-Cyclic Adenosine Monophosphate in Sertoli Cells," *Endocrinology*, 1999, 140:835-43 (Exhibit 83).

Guillou, Florian et al., "Sertoli Cell-specific Expression of the Human Transferrin Gene," *The Journal of Biological Chemistry*, 1991, 266:9876-84 (Exhibit 84).

Hacker, Adam et al., "Expression of *Sry*, the mouse sex determining gene," *Development*, 1995, 121:1603-14 (Exhibit 85).

Hansson, Vidar et al., "Cyclic-AMP-dependent protein kinase (PKA) in testicular cells. Cell specific expression, differential regulation and targeting of subunits of PKA," *Journal of Steroid Biochemistry & Molecular Biology*, 2000, 73:81-92 (Exhibit 86).

Hara, Eiji et al., "Id-related Genes encoding Helix-Loop-Helix Proteins are Required for $G_1$ Progression and Are Repressed in Senescent Human Fibroblasts," *The Journal of Biological Chemistry*, 1994, 269:2139-45 (Exhibit 87).

Hartman, Standish C. and Richard C. Mulligan, "Two dominant-acting selectable markers for gene transfer studies in mammalian cells," *Proc. Natl. Acad. Sci. USA*, 1988, 85:8047-51 (Exhibit 88).

Hatano, Osamu et al., "Sex-dependent expression of a transcription factor, Ad4BP, regulating steroidogenic P-450 genes in the gonads during prenatal and postnatal rat development," *Development*, 1994, 120:2787-97 (Exhibit 89).

Heckert, Leslie L. et al., "Multiple Promoter Elements Contribute to Activity of the Follicle-Stimulating Hormone Receptor (FSHR) Gene in Testicular Sertoli Cells," *Molecular Endocrinology*, 1998, 12:1499-512 (Exhibit 90).

Hitzeman, Ronald A. et al., "Isolation and Characterization of the Yeast 3-Phosphoglycerokinase Gene (*PGK*) by an Immunological Screening Technique," *The Journal of Biological Chemistry*, 1980, 255:12073-80 (Exhibit 91).

Hofmann, Marie-Claude et al., "Immortalization of Germ Cells and Somatic Testicular Cells Using the SV40 Large T Antigen," *Experimental Cell Research*, 1992, 201:417-35 (Exhibit 92).

Holland, Michael J. and Janice P. Holland, "Isolation and Identification of Yeast Messenger Ribonucleic Acids Coding for Enolase, Glyceraldehyde-3-phosphate Dehydrogenase, and Phosphoglycerate Kinase," *Biochemistry*, 1978, 17:4900-7 (Exhibit 93).

Holsberger, Denise R. et al., "Thyroid Hormone Regulates the Cell Cycle Inhibitor p27$^{Kip1}$ in Postnatal Murine Sertoli Cells," *Endocrinology*, 2003, 144:3732-8 (Exhibit 94).

Hu, Jing-Shan et al., "HEB, a Helix-Loop-Helix Protein Related to E2A and ITF2 That Can Modulate the DNA-Binding Ability of Myogenic Regulatory Factors," *Molecular and Cellular Biology*, 1992, 12:1031-42 (Exhibit 95).

Iavarone, Antonio et al., "The helix-loop-helix protein Id-2 enhances cell proliferation and binds to the retinoblastoma protein," *Genes & Development*, 1994, 8:1270-84 (Exhibit 96).

Isacson, Ole et al., "Graft-induced behavioral recovery in an animal model of Huntington disease," *Proc. Natl. Acad. Sci. USA*, 1986, 83:2728-32 (Exhibit 97).

Israel, Mark A. et al., "*Id* Gene Expression as a Key Mediator of Tumor Cell Biology," *Cancer Research*, 1999, 59:1726s-30s (Exhibit 98).

Jia, Meng-Chun et al., "Regulation of *c-fos* mRNA expression in Sertoli cells by cyclic AMP, calcium, and protein kinase C mediated pathways," *Molecular and Cellular Biochemistry*, 1996, 156:43-9 (Exhibit 99).

Karin, Michael and Robert I. Richards, "Human metallothionein genes—primary structure of the metallothionein-II gene and a related processed gene," *Nature*, 1982, 299:797-802 (Exhibit 100).

Kawai, Sadaaki and Makoto Nishizawa, "New Procedure for DNA Transfection with Polycation and Dimethyl-Sulfoxide," *Molecular and Cellular Biology*, 1984, 4:1172-4 (Exhibit 101).

Kebebew, Electron et al., "The helix-loop-helix transcription factor, Id-1, is overexpressed in medullary thyroid cancer," *Surgery*, 2000, 128:952-7 (Exhibit 102).

Ketola, Ilkka et al., "Developmental expression and spermatogenic stage specificity of transcription factors GATA-1 and GATA-4 and their cofactors FOG-1 and FOG-2 in the mouse testis," *European Journal of Endocrinology*, 2002, 147:397-406 (Exhibit 103).

Korbutt, Gregory S. et al., "Cotransplantation of Allogeneic Islets With Allogeneic Testicular Cell Aggregates Allows Long-Term Graft Survival Without Systemic Immunosuppression," *Diabetes*, 1997, 46:317-22 (Exhibit 104).

Korbutt, G. S. et al., "Testicular Sertoli cells exert both protective and destructive effects on syngeneic islet grafts in non-obese diabetic mice," *Diabetologia*, 2000, 43:474-480 (Exhibit 105).

Krishnamurthy, Hanumanthappa et al., "Qualitative and Quantitative Decline in Spermatogenesis of the Follicle-Stimulating Hormone Receptor Knockout (FORKO) Mouse," *Biology of Reproduction*, 2000, 62:1146-59 (Exhibit 106).

Kroll, David J. et al., "A Multifunctional Prokaryotic Protein Expression System: Overproduction, Affinity Purification, and Selective Detection," *DNA and Cell Biology*, 1993, 12:441-53 (Exhibit 107).

Kumar, T. Rajendra et al., "Follicle stimulating hormone is required for ovarian follicle maturation but not male fertility," *Nature Genetics*, 1997, 15:201-4 (Exhibit 108).

Langlands, Kenneth et al., "Differential Interactions of Id Proteins with Basic-Helix-Loop-Helix Transcription Factors," *The Journal of Biological Chemistry*, 1997, 272:19785-93 (Exhibit 109).

Langlands, Kenneth et al., "Id Proteins are Dynamically Expressed in Normal Epidermis and Dysregulated in Squamous Cell Carcinoma," *Cancer Research*, 2000, 60:5929-33 (Exhibit 110).

Lasorella, Anna et al., "Id2 is a retinoblastoma protein target and mediates signalling by Myc oncoproteins," *Nature*, 2000, 407:592-8 (Exhibit 111).

Lasorella, Anna et al., "Id2 Is Critical for Cellular Proliferation and is the Oncogenic Effector of N-Myc in Human Neuroblastoma," *Cancer Research*, 2002, 62:301-6 (Exhibit 112).

Lasorella, A. et al., "Id2 Specifically Alters Regulation of the Cell Cycle by Tumor Suppressor Proteins," *Molecular and Cellular Biology*, 1996, 16:2570-8 (Exhibit 113).

Lassar, Andrew B. et al., "Functional Activity of Myogenic HLH Proteins Requires Hetero-Oligomerization with E12/E47-like Proteins In Vivo," *Cell*, 1991, 66:305-15 (Exhibit 114).

Law, G. Lynn and Michael D. Griswold, "Activity and Form of Sulfated Glycoprotein 2 (Clusterin) from Cultured Sertoli Cells, Testis, and Epididymis of the Rat," *Biology of Reproduction*, 1994, 50:669-79 (Exhibit 115).

Lim, Kyu and Byung-Doo Hwang, "Follicle-stimulating hormone transiently induces expression of protooncogene c-myc in primary Sertoli cell cultures of early pubertal and prepubertal rat," *Molecular and Cellular Endocrinology*, 1995, 111:51-6 (Exhibit 116).

Lim, Kyu et al., "Testosterone Regulation of Proto-Oncogene c-myc Expression in Primary Sertoli Cell Cultures from Prepubertal Rats," *Journal of Andrology*, 1994, 15:543-50 (Exhibit 117).

Lin, Claudia Qiao et al., "A Role for Id-1 in the Aggressive Phenotype and Steroid Hormone Response of Human Breast Cancer Cells," *Cancer Research*, 2000, 60:1332-40 (Exhibit 118).

Lindvall, Olle et al., "Transplantation in Parkinson's Disease: Two Cases of Adrenal Medullary Grafts to the Putamen," *Annals of Neurology*, 1987, 22:457-68 (Exhibit 119).

Lindvall, Olle et al., "Grafts of Fetal Dopamine Neurons Survive and Improve Motor Function in Parkinson's Disease," *Science*, 1990, 247:574-7 (Exhibit 120).

Linetsky, Elina et al., "Improved Human Islet Isolation Using a New Enzyme Blend, Liberase," *Diabetes*, 1997, 46:1120-3 (Exhibit 121).

Liu, Hwan-Wun et al., "Intrastriatal transplantation of Sertoli cells may improve amphetamine-induced rotation and tyrosine hydroxylase immunoreactivity of the striatum in hemiparkinsonian rats," *Brain Research*, 1999, 838:227-33 (Exhibit 122).

Loeffler, J. Ph. et al., "Lipopolyamine-Mediated Transfection Allows Gene Expression Studies in Primary Neuronal Cells," *Journal of Neurochemistry*, 1990, 54:1812-5 (Exhibit 123).

Logan, John and Thomas Shenk, "Adenovirus tripartite leader sequence enhances translation of mRNAs late after infection," *Proceedings of the National Academy of Sciences USA*, 1984, 81:3655-9 (Exhibit 124).

Lovell-Badge, Robin and Adam Hacker, "The molecular genetics of Sry and its role in mammalian sex determination," *Phil. Trans. R. Soc. Lond. B*, 1995, 350:205-14 (Exhibit 125).

Loveys, Deborah A. et al., "E2A basic-helix-loop-helix transcription factors are negatively regulated by serum growth factors and by the Id3 protein," *Nucleic Acids Research*, 1996, 24:2813-20 (Exhibit 126).

Lowy, Israel et al., "Isolation of Transforming DNA: Cloning the Hamster aprt Gene," *Cell*, 1980, 22:817-23 (Exhibit 127).

Luca, Giovanni et al., "Sertoli Cell-Induced Reversal of Adult Rat Pancreatic Islet β-Cells Into Fetal-Like Status: Potential Implications for Islet Transplantation in Type I Diabetes Mellitus," *Journal of Investigative Medicine*, 2000, 48:441-8 (Exhibit 128).

Luthman, Holger and Göran Magnusson, "High efficiency polyoma DNA transfection of chloroquine treated cells," *Nucleic Acids Research*, 1983, 11:1295-308 (Exhibit 129).

Madrazo, Ignacio et al., "Open Microsurgical Autograft of Adrenal Medulla to the Right Caudate Nucleus in Two Patients With Intractable Parkinson's Disease," *The New England Journal of Medicine*, 1987, 316:831-4 (Exhibit 130).

Maruyama, Haruhisa et al., "Id-1 and Id-2 are Overexpressed in Pancreatic Cancer and in Dysplastic Lesions in Chronic Pancreatitis," *American Journal of Pathology*, 1999, 155:815-22 (Exhibit 131).

Massari, Mark Eben and Cornelis Murre, "Helix-Loop-Helix Proteins: Regulators of Transcription in Eucaryotic Organisms," *Molecular and Cellular Biology*, 2000, 20:429-40 (Exhibit 132).

Mather, Jennie P., "Establishment and Characterization of Two Distinct Mouse Testicular Epithelial Cell Lines," *Biology of Reproduction*, 1980, 23:243-52 (Exhibit 133).

McCutchan, James H. and Joseph S. Pagano, "Enhancement of the Infectivity of Simian Virus 40 Deoxyribonucleic Acid With Diethylaminoethyl-Dextran," *Journal of the National Cancer Institute*, 1968, 41:351-7 (Exhibit 134).

McGuinness, Michael P. et al., "Relationship of a Mouse Sertoli Cell Line (MSC-1) to Normal Sertoli Cells," *Biology of Reproduction*, 1994, 51:116-24 (Exhibit 135).

McLean, Derek J. et al., "Oligonucleotide Microarray Analysis of Gene Expression in Follicle-Stimulating Hormone-Treated Rat Sertoli Cells," *Molecular Endocrinology*, 2002, 16:2780-92 (Exhibit 136).

Moens, Ugo et al., "Mechanisms of Transcriptional Regulation of Cellular Genes by SV40 Large T- and Small T-Antigens," *Virus Genes*, 1997, 15:135-54 (Exhibit 137).

Moldes, Marthe et al., "Id3 Prevents Differentiation of Preadipose Cells," *Molecular and Cellular Biology*, 1997, 17:1796-804 (Exhibit 138).

Morihisa, John M. et al., "Adrenal Medulla Grafts Survive and Exhibit Catecholamine-Specific Fluorescence in the Primate Brain," *Experimental Neurology*, 1984, 84:643-53 (Exhibit 139).

Murre, Cornelis et al., "A New DNA Binding and Dimerization Motif in Immunoglobulin Enhancer Binding, *daughterlass*, *MyoD*, and *myc* Proteins," *Cell*, 1989, 56:777-83 (Exhibit 140).

Murre, Cornelis et al., "Interactions between Heterologous Helix-Loop-Helix Proteins Generate Complexes That Bind Specifically to a Common DNA Sequence," *Cell*, 1989, 58:537-44 (Exhibit 141).

Murre, Cornelis et al., "Structure and function of helix-loop-helix proteins," *Biochimica et Biophysica Acta*, 1994, 1218:129-35 (Exhibit 142).

Neumann, E. et al., "Gene transfer into mouse lyoma cells by electroporation in high electric fields," *The EMBO Journal*, 1982, 1:841-5 (Exhibit 143).

Nickoloff, Brian J. et al., "Id-1 Delays Senescence but Does Not Immortalize Keratinocytes," *The Journal of Biological Chemistry*, 2000, 275:27501-4 (Exhibit 144).

Nieto-Sampedro, M. et al., "Brain Injury Causes a Time-Dependent Increase in Neuronotrophic Activity at the Lesion Site," *Science*, 1982, 217:860-1 (Exhibit 145).

Nieto-Sampedro, M. et al., "The survival of brain transplants is enhanced by extracts from injured brain," *Proceedings of the National Academy of Sciences USA*, 1984, 81:6250-4 (Exhibit 146).

Norton, John D., "ID helix-loop-helix proteins in cell growth, differentiation and tumorigenesis," *Journal of Cell Science*, 2000, 113:3897-905 (Exhibit 147).

Norton, John N. and Michael K. Skinner, "Regulation of Sertoli Cell Differentiation by the Testicular Paracrine Factor PModS: Potential Role of Immediate-Early Genes," *Molecular Endocrinology*, 1992, 6:2018-26 (Exhibit 148).

Ohtani, Naoko et al., "Opposing effects of Ets and Id proteins on $p16^{INK4a}$ expression during cellular senescence," *Nature*, 2001, 409:1067-70 (Exhibit 149).

Orth, Joanne M. et al., "Evidence From Sertoli Cell-Depleted Rats Indicates That Spermatid Number in Adults Depends on Number of Sertoli Cells Produced During Perinatal Development," *Endocrinology*, 1988, 122:787-94 (Exhibit 150).

Othberg, Agneta I. et al., "Preparation of cell suspensions for co-transplantation: methodological considerations," *Neuroscience Letters*, 1998, 247:111-14 (Exhibit 151).

Perlow, Mark J. et al., "Brain Grafts Reduce Motor Abnormalities Produced by Destruction of Nigrostriatal Dopamine System," *Science*, 1979, 204:643-7 (Exhibit 152).

Peschon, Jacques J. et al., "Directed Expression of an Oncogene to Sertoli Cells in Transgenic Mice Using Mullerian Inhibiting Substance Regulatory Sequences," *Molecular Endocrinology*, 1992, 6:1403-11 (Exhibit 153).

Petersen, C. et al., "Interleukin-1 is a potent growth factor for immature rat Sertoli cells," *Molecular and Cellular Endocrinology*, 2002, 186:37-47 (Exhibit 154).

Prabhu, Sumangala et al., "Regulation of the Expression of Cyclin-Dependent Kinase Inhibitor p21 by E2A and Id Proteins," *Molecular and Cellular Biology*, 1997, 17:5888-96 (Exhibit 155).

Prasad, K. N. et al., "Defects in cAMP-pathway may initiate carcinogenesis in dividing nerve cells: A review," *Apoptosis*, 2003, 8:579-86 (Exhibit 156).

Quong, Melanie W. et al., "A New Transcriptional-Activation Motif Restricted to a Class of Helix-Loop-Helix Proteins is Functionally Conserved in Both Yeast and Mammalian Cells," *Molecular and Cellular Biology*, 1993, 13:792-800 (Exhibit 157).

Rassoulzadegan, Minoo et al., "Transmeiotic Differentiation of Male Germ Cells in Culture," *Cell*, 1993, 75:997-1006 (Exhibit 158).

Redmond, D. Eugene et al., "Fetal Neuronal Grafts in Monkeys Given Methylphenyltetrahydropyridine," *The Lancet*, 1986, 1:1125-7 (Exhibit 159).
Rhodes, Carol A. et al., "Transformation of Maize by Electroporation of Embryos," *Methods in Molecular Biology*, 1995, 55:121-31 (Exhibit 160).
Roberts, Kenneth P. et al., "Immortalization and Characterization of a Sertoli Cell Line from the Adult Rat," *Biology of Reproduction*, 1995, 53:1446-53 (Exhibit 161).
Rosenberg, Michael B. et al., "Grafting Genetically Modified Cells to the Damaged Brain: Restorative Effects of NGF Expression," *Science*, 1988, 242:1575-8 (Exhibit 162).
Sablitzky, Fred et al., "Stage- and Subcellular-specific Expression of Id Proteins in Male Germ and Sertoli CellS Implicates Distinctive Regulatory Roles for Id Proteins during Meiosis, Spermatogenesis, and Sertoli Cell Function," *Cell Growth & Differentiation*, 1998, 9:1015-24 (Exhibit 163).
Sanberg, Paul R. et al., "Testis-derived Sertoli cells survive and provide localized immunoprotection for xenografts in rat brain," *Nature Biotechnology*, 1996, 14:1692-5 (Exhibit 164).
Sanberg, Paul R. et al., "Testis-derived Sertoli cells have a trophic effect on dopamine neurons and alleviate hemiparkinsonism in rats," *Nature Medicine*, 1997, 3:1129-32 (Exhibit 165).
Saxlund, Melissa A. et al., "Role of Basic Helix-Loop-Helix (bHLH) and CREB Transcription Factors in the Regulation of Sertoli Cell Androgen-Binding Protein Expression," *Molecular Reproduction and Development*, 2004, 68:269-78 (Exhibit 166).
Schaefer-Ridder, Maria et al., "Liposomes as Gene Carriers: Efficient Transformation of Mouse L Cells by Thymidine Kinase Gene," *Science*, 1982, 215:166-8 (Exhibit 167).
Scharf, Klaus-Dieter et al., "Heat Stress Promoters and Transcription Factors," *Results and Problems in Cell Differentiation*, 1994, 20:125-62 (Exhibit 168).
Schlatt, Stefan et al., "Discriminative Analysis of Rat Sertoli and Peritubular Cells and Their Proliferation In Vitro: Evidence for Follicle-Stimulating Hormone-Mediated Contact Inhibition of Sertoli Cell Mitosis," *Biology of Reproduction*, 1996, 55:227-35 (Exhibit 169).
Schurch-Rathgeb, Y. and D. Monard, "Brain development influences the appearance of glial factor-like activity in rat brain primary cultures," *Nature*, 1978, 273:308-9 (Exhibit 170).
Scobey, M. Joseph et al., "The Id2 Transcriptional Repressor Is Induced by Follicle-stimulating Hormone and cAMP," *The Journal of Biological Chemistry*, 2004, 279:16064-70 (Exhibit 171).
Sharpe, R. M. et al., "Effect of Neonatal Gonadotropin-Releasing Hormone Antagonist Administration on Sertoli Cell Number and Testicular Development in the Marmoset: Comparison with the Rat," *Biology of Reproduction*, 2000, 62:1685-93 (Exhibit 172).
Sharpe, Richard M. et al., "Proliferation and functional maturation of Sertoli cells, and their relevance to disorders of testis function in adulthood," *Reproduction*, 2003, 125:769-84 (Exhibit 173).
Shima, James E. et al., "The Murine Testicular Transcriptome: Characterizing Gene Expression in the Testis During the Progression of Spermatogenesis," *Biology of Reproduction*, 2004, 71:319-30 (Exhibit 174).
Shimohama, S. et al., "Grafting genetically modified cells into the rat brain: characteristics of *E. coil* β-galactosidase as a reporter gene," *Molecular Brain Research*, 1989, 5:271-8 (Exhibit 175).
Shokouh-Amiri, M. H. et al., "Does Survival Depend on the Amount of Autotransplanted Splenic Tissue?," *Arch Surg*, 1990, 125:1472-4 (Exhibit 176).
Silva, Fátima R. M. B. et al., "Rapid signal transduction in Sertoli cells," *European Journal of Endocrinology*, 2002, 147:425-433 (Exhibit 177).
Skinner, Michael K., "Cell-Cell Interactions in the Testis," *Endocrine Reviews*, 1991, 12:45-77 (Exhibit 178).
Skinner, Michael K. and Michael D. Griswold, "Secretion of Testicular Transferrin by Cultured Sertoli Cells is Regulated by Hormones and Retinoids," *Biology of Reproduction*, 1982, 27:211-21 (Exhibit 179).

Skinner, Michael K. et al., "Purification of a Paracrine Factor, P-Mod-S, Produced by Testicular Peritubular Cells That Modulates Sertoli Cell Function," *The Journal of Biological Chemistry*, 1988, 263:2884-90 (Exhibit 180).
Skinner, Michael K. et al., "Regulation of Sertoli Cell Differentiated Function: Testicular Transferrin and Androgen-Binding Protein Expression," *Endocrinology*, 1989, 124:3015-24 (Exhibit 181).
Southern, E. M., "Detection of Specific Sequences Among DNA Fragments Separated by Gel Electrophoresis," *Journal of Molecular Biology*, 1975, 98:503-17 (Exhibit 182).
Stenevi, Ulf et al., "Transplantation of Central and Peripheral Monoamine Neurons to the Adult Rat Brain: Techniques and Conditions for Survival," *Brain Research*, 1976, 114:1-20 (Exhibit 183).
Stork, Philip J. S. and John M. Schmitt, "Crosstalk between cAMP and MAP kinase signaling in the regulation of cell proliferation," *Trends in Cell Biology*, 2002, 12:258-66 (Exhibit 184).
Suarez-Pinzon, Wilma et al., "Testicular Sertoli Cells Protect Islet β-Cells from Autoimmune Destruction in NOD Mice by a Transforming Growth Factor-β1-Dependent Mechanism," *Diabetes*, 2000, 49:1810-8 (Exhibit 185).
Suire, S. et al., "Follicle Stimulating Hormone (FSH) Stimulates Transferrin Gene Transcription in Rat Sertoli Cells: *cis* and *trans*-Acting Elements Involved in FSH Action via Cyclic Adenosine 3',5'—Monophosphate on the Transferrin Gene," *Molecular Endocrinology*, 1995, 9:756-66 (Exhibit 186).
Tabuchi, Yoshiaki et al., "Development of a Conditionally Immortalized Testicular Sertoli Cell Line RTS3-3 from Adult Transgenic Rats Harboring Temperature-Sensitive Simian Virus 40 Large T-antigen Gene," *Cell Structure and Function*, 2003, 28:87-95 (Exhibit 187).
Takai, Noriyuki et al., "Id1 expression is associated with histological grade and invasive behavior in endometrial carcinoma," *Cancer Letters*, 2001, 165:185-93 (Exhibit 188).
Tam, S. K. C. et al., "Cardiac Myocyte Terminal Differentiation: Potential for Cardiac Regeneration," *Annals New York Academy of Sciences*, 1995, 752:72-9 (Exhibit 189).
Tang, Jun et al., "The Helix-Loop-Helix Protein Id-1 Delays Onset of Replicative Senescence in Human Endothelial Cells," *Laboratory Investigation*, 2002, 82:1073-9 (Exhibit 190).
Toyama, Reiko and Hiroto Okayama, "Human chorionic gonadotropin a and human cytomegalovirus promoters are extremely active in the fission yeast *Schizosaccharomyces pombe*," FEBS, 1990, 268:217-21 (Exhibit 191).
Tung, Pierre S. et al., "Fibronectin Synthesis is a Marker for Peritubular Cell Contaminants in Sertoli Cell-Enriched Cultures," *Biology of Reproduction*, 1984, 30:199-211 (Exhibit 192).
Turlejski, Kris and Ruzanna Djavadian, "Life-long stability of neurons: a century of research on neurogenesis, neuronal death and neuron quantification in adult CNS," *Progress in Brain Research*, 2002, 136:39-65 (Exhibit 193).
Tze, W. J. and J. Tai, "Manipulation of Pancreatic Islet Cells in Allotransplantation," *Transplantation Proceedings*, 1982, 14:714-23 (Exhibit 194).
Unsicker, K. et al., "Nerve growth factor-induced fiber outgrowth from isolated rat adrenal chromaffin cells: Impairment by glucocorticoids," *Proceedings of the National Academy of Sciences USA*, 1978, 75:3498-502 (Exhibit 195).
Unsicker, Klaus et al., "C6 glioma cell-conditioned medium induces neurite outgrowth and survival of rat chromaffin cells in vitro: Comparison with the effects of nerve growth factor," *Proceedings of the National Academy of Sciences USA*, 1984, 81:2242-6 (Exhibit 196).
Walker, William H., "Molecular Mechanisms Controlling Sertoli Cell Proliferation and Differentiation," *Endocrinology*, 2003, 144:3719-21 (Exhibit 197).
Walker, William H. et al., "Expression of the Gene Encoding Transcription Factor Cyclic Adenosine 3',5'-Monophosphate (cAMP) Response Element-Binding Protein (CREB): Regulation by Follicle-Stimulating Hormone-Induced cAMP Signaling in Primary Rat Sertoli Cells," *Endocrinology*, 1995, 136:3534-45 (Exhibit 198).
Walther, Norbert et al., "Sertoli Cell Lines Established from *H-2K$^b$-tsA58* Transgenic Mice Differentially Regulate the Expression of Cell-Specific Genes," *Experimental Cell Research*, 1996, 255:411-21 (Exhibit 199).

Wegner, Michael, "Expression of Transcription Factors During Oligodendroglial Development," *Microscopy Research and Technique*, 2001, 52:746-52 (Exhibit 200).

Wei, Qin and Bruce M. Paterson, "Regulation of MyoD function in the dividing myoblast," *FEBS Letters*, 2001, 490:171-8 (Exhibit 201).

Whitaker-Azmitia, Patricia M. and Efrain C. Azmitia, "Stimulation of astroglial serotonin receptors produces culture media which regulates growth of serotonergic neurons," *Brain Research*, 1989, 497:80-5 (Exhibit 202).

Widner, Håkan et al., "Bilateral Fetal Mesencephalic Grafting in Two Patients With Parkinsonism Induced by 1-Methyl-4-Phenyl-1,2,3,6-Tetrahydropyridine (MPTP)," *The New England Journal of Medicine*, 1992, 327:1556-63 (Exhibit 203).

Wigler, M. et al., "Transformation of mammalian cells with an amplifiable dominant-acting gene," *Proceedings of the National Academy of Sciences USA*, 1980, 77:3567-70 (Exhibit 204).

Wigler, Michael et al., "Transfer of Purified Herpes Virus Thymidine Kinase Gene to Cultured Mouse Cells," *Cell*, 1977, 11:223-32 (Exhibit 205).

Willing, Alison E. et al., "Sertoli cells enhance the survival of co-transplanted dopamine neurons," *Brain Research*, 1999, 822:246-50 (Exhibit 206).

Wilson, James W. et al., "Expression of Id Helix-Loop-Helix Proteins in Colorectal Adenocarcinoma Correlates with p53 Expression and Mitotic Index," *Cancer Research*, 2001, 61:8803-10 (Exhibit 207).

Wong, W. S. Felix et al., "Establishment and Characterization of a New Human Cell Line Derived from Ovarian Clear Cell Carcinoma," *Gynecologic Oncology*, 1990, 38:37-45 (Exhibit 208).

Yang, Hua and James R. Wright, Jr., "Co-Encapsulation of Sertoli Enriched Testicular Cell Fractions Further Prolongs Fish-to-Mouse Islet Xenograft Survival," *Transplantation*, 1999, 67:815-20 (Exhibit 209).

Yokota, Yoshifumi and Seiichi Mori, "Role of Id Family Proteins in Growth Control," *Journal of Cellular Physiology*, 2002, 190:21-8 (Exhibit 210).

Yomogida, Kentaro et al., "Developmental stage- and spermatogenic cycle-specific expression of transcription factor GATA-1 in mouse Sertoli cells," *Development*, 1994, 120:1759-66 (Exhibit 211).

Yoshikawa, Kazuaki, "Cell cycle regulators in neural stem cells and postmitotic neurons," *Neuroscience Research*, 2000, 37:1-14 (Exhibit 212).

Zebedee, Zoe and Eiji Hara, "Id proteins in cell cycle control and cellular senescence," *Oncogene*, 2001, 20:8317-25 (Exhibit 213).

Zheng, Wenjie et al., "Regulation of Cellular Senescence and $p16^{INK4a}$ Expression by Id1 and E47 Proteins in Human Diploid Fibroblast," *The Journal of Biological Chemistry*, 2004, 279:31524-32 (Exhibit 214).

* cited by examiner

MODIFIED CELLS EXPRESSING A PROTEIN THAT MODULATES ACTIVITY OF BHLH PROTEINS, AND USES THEREOF

This application is based on PCT Application No. PCT/US2005/014857, filed Apr. 29, 2005, which claims the priority of the provisional application U.S. Ser. No. 60/566,685, filed Apr. 29, 2004, the contents of which are hereby incorporated by reference, in their entirety, into this application.

The invention disclosed herein was made with government support under Grant No. HD34707 awarded by the National Institutes of Health. The government has certain rights in this invention.

Throughout this application various publications are referenced. The disclosures of these publications are hereby incorporated by reference, in their entirety, into this application in order to more fully describe the state of the art to which the invention pertains.

FIELD OF INVENTION

The present invention relates to modified cells carrying a heterologous helix-loop-helix gene sequence, and expressing a heterologous protein that binds and modulates the activity of a basic helix-loop-helix (bHLH) protein, and more particularly to the use of such modified cells that do not become tumorigenic, in cell therapies, degenerative diseases and tissue treatments, including transplantation, and as targets in cell-based assays.

BACKGROUND OF THE INVENTION

Sertoli cells are the testicular epithelial cells that form the seminiferous tubule and provide the cytoarchitectural support and microenvironment for the developing germ cells (B Jegou 1992 Bailliere's Clin Endocrinol Metab 6:273-311; M K Skinner 1991 Endocr Rev 12:45-77). In a mammalian male testicle, the Sertoli cells are the predominant cells which function to support spermatogenesis by providing a microenvironmental and structural support for the developing germ cells.

Before puberty, the Sertoli cells undergo active proliferation, but at puberty and through adulthood they become a terminally differentiated, post-mitotic cell population. The Sertoli cell number per testis determines the efficiency of spermatogenesis. Sertoli cell function is regulated by the gonadotropin FSH and locally produced paracrine factors. Before puberty, these hormones and growth factors can increase Sertoli cell proliferation, but after puberty they fail to influence cell growth.

The molecular mechanisms involved in the post-mitotic block in post-pubertal Sertoli cells are unknown, but may involve up-regulation of cell cycle inhibitory genes such as p16 and p21. The four known helix-loop-helix Id proteins (Id1, Id2, Id3, and Id4), are considered dominant negative regulators of differentiation pathways, but positive regulators of cellular proliferation. The Id proteins are expressed by post-pubertal Sertoli cells. Similar to other cell systems, Id1, Id2 and Id3 are also transiently induced by serum in Sertoli cells.

Terminal differentiation is the state achieved when a cell exits the cell cycle, to become post-mitotic, and the differentiated gene expression profile allows a specialized function for the cell. Often, these terminally differentiated cells cannot be replenished and once lost can cause abnormal tissue function. Examples of terminally differentiated cells include neurons (Yoshikawa 2000), myocytes (Tam et al. 1995; Wei and Paterson 2001) and Sertoli cells (Walker 2003). Abnormalities or loss of these terminally differentiated cells causes corresponding neuro-degeneration (Jellinger 2003; Turlejski and Djavadian 2002), muscle degeneration (Bicknell et al. 2003) or infertility disease states (Sharpe et al. 2003).

The cellular mechanisms that promote and maintain terminal differentiation are poorly understood. The speculation is that altered signal transduction and cell cycle pathways influenced by unique transcriptional events allow a cell to exit irreversibly the cell cycle and promote a unique spectrum of gene expression required by the cell (Prasad et al. 2003; Wegner 2001; Wei and Paterson 2001; Yoshikawa 2000).

Sertoli cell fate is established in the embryonic gonad at the time of sex determination (Hacker et al. 1995; Lovell-Badge and Hacker 1995) and is followed by a phase of rapid cell proliferation and differentiation. During puberty the final phase of Sertoli cell differentiation occurs which is marked by cessation of proliferation and irreversible changes in Sertoli cell morphology and physiology (Jegou 1992). The changes associated with terminal differentiation of Sertoli cells at puberty, include exit from the cell cycle and the formation of the blood testis barrier. This differentiated phenotype is needed for the proper microenvironment and cytoarchitectural support of the developing spermatogenic cells. The Sertoli cell differentiation is accompanied by the expression of many gene products not present in immature cells such as aromatase, androgen receptor (Bremner et al. 1994), GATA-1 (Ketola et al. 2002), p27kip (Holsberger et al. 2003), SGP-2 (Law and Griswold 1994), and laminin alpha 5 (Schlatt et al. 1996) and transferrin (Norton and Skinner 1992).

In general, hormones and growth factors such as FSH (Simoni et al. 1999), thyroid hormone (Holsberger et al. 2003; Palmero et al. 1995), interleukin-1 alpha (Petersen et al. 2002) and TGF alpha (Petersen et al. 2002), increase proliferation of Sertoli cells obtained from prenatal and pre-pubertal testis. The early post pubertal Sertoli cells also remain responsive to these hormones and growth factors, but fail to proliferate and enter the cell cycle (Buzzard et al. 2003; Sharpe et al. 2003). The molecular mechanisms involved in this switch to a post-mitotic and irreversible exit from the cell cycle at puberty are largely unknown. The altered expression of certain regulatory signaling networks involved in the action of these hormones and growth factors is likely involved (Buzzard et al. 2003; Holsberger et al. 2003). For example, pre-pubertal Sertoli cell proliferation may involve activation of the ERK-MAP kinase pathway and subsequent up-regulation of cyclin D1 in response to FSH (Crepieux et al. 2001). Sertoli cells' exit from the cell cycle may be due to induction of the growth inhibitor p27-CIP1 by TH, T and RA (Holsberger et al. 2003). In addition, FSH may also inhibit post-pubertal proliferation through the activation of the PKA-cAMP pathway (Crepieux et al. 2001). This is consistent with the role of cAMP as an inhibitor of proliferation for many cells (Stork and Schmitt 2002).

The majority of the Sertoli cell functions are regulated by the gonadotropin FSH (Simoni et al. 1999). The loss of FSH actions are reflected in reduced Sertoli cell numbers with no qualitative loss on spermatogenesis, but the total number of sperm are reduced (Krishnamurthy et al. 2000). Previous observations have suggested that quantitative spermatogenesis is dependent on the total number of Sertoli cells established prepubertally (Sharpe et al. 2000). The functions of differentiated Sertoli cell are regulated by a combination of hormones and various growth factors. Optimum cell function is maintained through the activation of various signal transduction pathways including protein kinase A, protein kinase C and calcium mobilization (Braun et al. 2002; Hansson et al.

2000; Jia et al. 1996; Silva et al. 2002). These signal transduction pathways activate a number of transcription factors such as cAMP response element-binding protein (Walker et al. 1995), C/EBPβ (Gronning et al. 1999), c-fos (Norton and Skinner 1992), c-myc (Lim and Hwang 1995), GATA-1 (Yomogida et al. 1994), SF-1 (Hatano et al. 1994), and WIN (Chaudhary et al. 2000). It is postulated that the activation of specific combinations of these transcription factors is in part responsible for stage dependent proliferation and differentiation of Sertoli cells.

Sertoli cells have been shown to express members of the basic helix-loop-helix (bHLH) transcription factor family (Chaudhary et al. 1997; Chaudhary et al. 1999; Chaudhary and Skinner 1999a). The family members of bHLH transcription factors are critical cell-type determinants and play important roles in cellular differentiation. A bHLH domain that is conserved from yeast to mammals characterizes the members of this family (Quong et al. 1993). The bHLH domain consists of two amphipathic helices separated by a loop that mediates homo- and heterodimerization adjacent to a DNA-binding region rich in basic amino acids (Murre et al. 1994). The bHLH dimers bind to an E Box (CANNTG) DNA consensus sequence present in a wide variety of tissue-specific promoters (Murre et al. 1989a; Murre et al. 1989b). The E box domain has been shown to influence the promoters of a number of Sertoli cell genes, including transferrin (Chaudhary et al. 1997), c-fos (Chaudhary and Skinner 1999b), SF-1 (Daggett et al. 2000), and FSH receptor (Goetz et al. 1996). The bHLH proteins have been classified into two distinct classes. The ubiquitously expressed class A bHLH proteins consist of E2-2 (Bain et al. 1993), HEB (Hu et al. 1992), and E12 and E47 (i.e. differentially spliced products of the E2A gene (Murre et al. 1989b)). The class A bHLH dimerize with tissue-restricted and developmentally regulated class B proteins, such as MyoD and neuroD (Lassar et al. 1991; Massari and Murre 2000). Previous observations suggest that the Sertoli cells express the class A proteins E47 (Chaudhary and Skinner 1999a) and human HEB (Chaudhary et al. 1999) (i.e. the rat isoform of human HEB). Sertoli cell-specific class B bHLH proteins are yet to be determined. However, reports suggest that bHLH proteins regulate FSH-stimulated Sertoli cell gene expression (Chaudhary et al. 1997; Chaudhary and Skinner 1999b; Chaudhary and Skinner 1999c).

The members of the Id (inhibitor of differentiation/DNA binding) family modulate the transcriptional activity of class A and B bHLH heterodimers. The four known Id proteins (Id1, Id2, Id3, and Id4) share a homologous HLH domain, but lack the basic DNA binding region (Benezra et al. 1990; Daggett et al. 2000). Thus, the Id proteins act to sequester bHLH proteins by forming inactive dimers to prevent binding of bHLH proteins to the E-box responsive elements (Einarson and Chao 1995; Langlands et al. 1997; Loveys et al. 1996). Therefore, Id proteins are largely considered as dominant negative regulators of differentiation pathways (Barone et al. 1994; Hara et al. 1994; Moldes et al. 1997), but positive regulators of cellular proliferation. The induction of Id in various cell types has been studied in response to serum, which is known to induce proliferation of most cells.

The biphasic expression pattern of Id1 and Id2 in human diploid fibroblasts after serum stimulation corresponding to G1 phase and G1-S transition supports their role in proliferation (Hara et al. 1994). In addition to Id1 and Id2, Id3 is also induced early after cell cycle stimulation (Christy et al. 1991). The mechanisms by which Id proteins promote the cell cycle are diverse but appear to involve suppression of p21, p27, cyclin A, cyclin E, cyclin dependent kinase-2 (cdK2), and interactions with pRb (Zebedee and Hara 2001). Previous observations suggest that the differentiated Sertoli cells also express Id proteins (Buzzard et al. 2003; Chaudhary et al. 2001; Sablitzky et al. 1998). The functional significance of Id protein expression in terminally differentiated and post-mitotic Sertoli cells is unclear. Recent observations suggest that long-term (72 hour) stimulation of Sertoli cells in culture with FSH down-regulates Id1 and Id3. In contrast, serum up-regulates Id and Id3 expression (Chaudhary et al. 2001). Short-term stimulation of Sertoli cells with FSH (30 min-12 h) up-regulates Id2 in a biphasic manner. This response mimics the effect of mitogens on other cell systems (Zebedee and Hara 2001). The transient up regulation of Id genes in response to FSH suggests that differentiated Sertoli cells may be competent to re-enter the cell cycle if Id gene expression is sustained.

Organ transplantation remains a last-resort treatment for certain diseases that cause chronic organ damage. One of the main obstacles to long-term disease relief is transplant rejection, caused by immune response destruction of the transplanted organ. Presently, the only recourse to combat this immune response is to administer nonspecific immunosuppressive agents (Lancet 345:1321-1325 (1995). Unfortunately, life-long use of immunosuppressive agents increases the risks of cardiovascular disease, infections and malignancies. There remains a need for compositions and methods that decrease transplant rejection in the recipient subject.

One of the diseases that causes chronic organ damage is diabetes mellitus. Organ transplantation has been used to treat diabetes mellitus, but with limited success. Diabetes mellitus is characterized by a relative or complete lack of insulin secretion by the beta cells within the islets of Langerhans of the pancreas, or by defective insulin receptors. A vast number of diabetic patients receiving islet transplants experience transplant rejection and short-term insulin independence. For example, only 12.4% of the patients receiving islet allograft transplants experienced insulin independence for periods of more than one week, and only 8.25% have been insulin independent for periods of more than one year (Linsley et al. 1997 Diabetes 46: 1120-3).

One method for inhibiting transplant rejection includes co-grafting the transplant organ, tissue or cells with non-modified Sertoli cells. It has been previously shown that co-grafting non-modified Sertoli cells with the transplant enhances the viability of transplant organs in the recipient subject (U.S. Pat. Nos. 5,702,700; 5,725,854; 5,759,534; 5,830,460; and 5,849,285). The non-modified Sertoli cells produce a cellular factor, or factors, which create an immuno-privileged site for the co-grafted transplant, thereby enhancing the ability of the transplant to function, mature, proliferate, and/or survive (e.g., enhanced viability). The identity of the factor(s) is not yet known. However, non-modified Sertoli cells are known to produce cellular factors, including IGF (insulin-like growth factor), EGF (epidermal growth factor), and/or transferrin. These factors may or may not inhibit transplant rejection.

Although co-grafting methods using non-modified Sertoli cells offer some relief from transplant rejection, these methods also suffer drawbacks, because the grafted non-modified Sertoli cells do not proliferate and cannot regenerate the tissue. Thus, there still exists a need for cells that inhibit transplant rejection and do not undergo tumorigenesis.

The bHLH proteins are known to mediate cell growth and differentiation. In general, the bHLH proteins form a family of transcription activation factors having a helix-loop-helix domain (C Murre, et al 1994 Biochem Biophys Acta 1218: 129-135; C Murre, et al., 1989 Cell 56:777-783) and a DNA binding domain. The helix-loop-helix domain is essential for dimerization with other bHLH proteins. The dimerized protein complex is an activated transcription factor. In the dimerized complex, the DNA-binding domain mediates binding to a consensus E-box (CANNTG) DNA sequence resulting in transcription activation (A B Lassar, et al., 1991 Cell 66:305-315). The E-box sequence is present in various tissue-specific promoters including-specific promoters such as transferrin and others (C Murre, et al., 1989 Cell 56:777-783; C Murre, et al., Cell 58:537-544; J Chaudhary, et al., 1997 Endocrinology 138:667-675; J Chaudhary and M K Skinner 1999 Mol Endocrinol 13:774-786; M A Daggett, et al., 2000 Biol Reprod 62:670-679; T L Goetz, et al., 1996 J Biol Chem 271:33317-33324).

The family of bHLH proteins includes class A and B bHLH heterodimers (M W Quong, et al 1993 Mol Cell Biol 13:792-800). The class A bHLH proteins include E2-2 (G Bain, et al 1993 Mol Cell Biol 13:3522-3529), HEB (J S Hu, et al 1992 Mol Cell Biol 12:1031-1042), E47 (J Chaudhary and M K Skinner 1999 Mol Reprod Dev 52:1-8), REB-alpha (J Chaudhary, et al 1999 Biol Reprod 60:1244-1250), and E12 and E47 which are differentially spliced products of the E2A gene sequence (C Murre, et al 1989 Cell 58:537-544). The class B bHLH proteins include MyoD and neuroD (A B Lassar, et al 1991 Cell 66:305-315; M E Massari and C Murre 2000 Mol Cell Biol 20:429-440).

The Id proteins are also members of the bHLH family of proteins. The Id proteins share the structural helix-loop-helix domains found in the bHLH proteins, however the Id proteins lack the DNA-binding domain. The Id proteins bind the bHLH proteins to form inactive heterodimers, thereby preventing the bHLH proteins from binding their cognate E-box DNA sequences and preventing transcriptional activation by the bHLH protein (M B Einarson and M V Chao 1995 Mol Cell Biol 15:4175-4183; K Langlands, et al. 1997 J Biol Chem 272:19785-19793; D A Loveys, et al., 1996 Nucleic Acids Res 24:2813-2820; M V Barone, et al., 1994 Proc Natl Acad Sci USA 91:4985-4988; E Hara, et al., 1994 J Biol Chem 269:2139-2145; M Moldes, et al., 1997 Mol Cell Biol 17:1796-1804). Thus, the members of the Id protein family modulate transcriptional activity of the bHLH proteins thereby modulating cellular differentiation. The Id2 protein also includes an N-terminal domain which mediates apoptosis.

The bHLH proteins are postulated to interact with other cellular proteins to mediate transcriptional activation of genes involved in cell growth and/or differentiation. It has been suggested that the bHLH proteins activate transcription of gene sequences controlled by an E-box promoter sequence through transcriptional co-activator proteins, such as CREB (e.g., a CRE-binding protein or a cAMP response element-binding protein) (S Suire, et al., 1995 Mol Endocrinol 9:756-766; J Chaudhary and M K Skinner 1999 Endocrinology 140:1262-1271; J Chaudhary and M K Skinner 2001 Biology of Reproduction 65:568-574) and/or through adaptor proteins, such as CBP (cAMP response element-binding protein-binding protein) (J C Chrivia, et al., 1993 Nature 365:855-859; J Chaudhary and M K Skinner 2001 Biology of Reproduction 65:568-574) and/or p300 (R Eckner, et al., 1994 Genes Dev 8:869-884; J Chaudhary and M K Skinner 2001 Biology of Reproduction 65:568-574). Accordingly, the heterologous protein (e.g., Id proteins) expressed in the inventive modified cells may bind the CREB, CBP, and/or p300 proteins to inhibit transcriptional activation, thereby inhibiting cell growth, differentiation, or tumorigenesis of the modified cells.

There still remains a need for cells able to be used as therapeutic agents for treatment of diseases and to inhibit transplant rejection, that do not become tumorigenic in the recipient subject, and as targets in cell based assays for drug discovery and screening.

SUMMARY OF THE INVENTION

Accordingly, the present invention provides modified cells carrying a heterologous gene sequence encoding a heterologous protein that binds and inhibits the normal activity of a basic helix-loop-helix (bHLH) protein, or a bHLH protein binding complex, thereby inhibiting cell growth, differentiation, and/or tumorigenesis, and or mediating apoptosis of the modified cell. Thus, the modified cells of the invention are transgenic cells which are useful for inhibiting transplant rejection in a recipient subject, and do not become tumorigenic in a recipient subject. The modified cells are useful for individual cell therapy and/or co-grafting with transplant organs, tissue, or cells.

The modified cells of the present invention express the heterologous protein that binds and inhibits the normal activity of the bHLH protein, and the cells can produce factor(s) for cell therapy and/or to inhibit transplant rejection.

The modified cells of the invention can be Sertoli, neuron or muscle cells. In one embodiment, the heterologous gene sequence encodes at least one Inhibitor of differentiation (Id) protein, such as Id1, Id2, Id3, or Id4.

The modified cells can change to a less-differentiated state or to a dedifferentiated state.

The present invention also provides pharmaceutical compositions and kits, containing the modified cells of the invention and other ingredients.

The present invention includes methods for generating the modified cells of the invention. In one embodiment, the modified cells are generated using any isolated cell that produces factor(s) for cell therapy and/or inhibit transplant rejection.

The present invention further provides methods for inhibiting transplant rejection in a recipient subject, by co-grafting to the recipient subject, the modified cells with a transplant organ, tissue or cell.

Additional methods of the invention are methods for co-culturing the modified cells of the invention with other cells, in order to enhance the function of the co-cultured cells.

Other methods include co-culturing the modified cells of the invention with thawing cells, that have been cryo-preserved, in order to enhance the viability of the thawing cells.

Still other methods include use of the cells of the invention as targets in cell based assays, for drug discovery and screening.

BRIEF DESCRIPTION OF FIGURES

FIG. 2A: Id1 corrected. FIG. 2B: Id2 days/dbl corrected. FIG. 2C: Id1 doubling/day. FIG. 2D: Id2 doubling/day.

FIGS. 4A and B: Primary Sertoli cells. FIGS. 4C and D: Sertoli cells over-expressing Id1. FIGS. 4E and F: Sertoli cells over-expressing Id2. FIGS. 4A, C and D are representative images of un-stimulated Sertoli cells, whereas FIGS. 4B, D and F are images of Sertoli cells following cAMP stimulation for 72 hours.

DETAILED DESCRIPTION OF THE INVENTION

Figure 1:
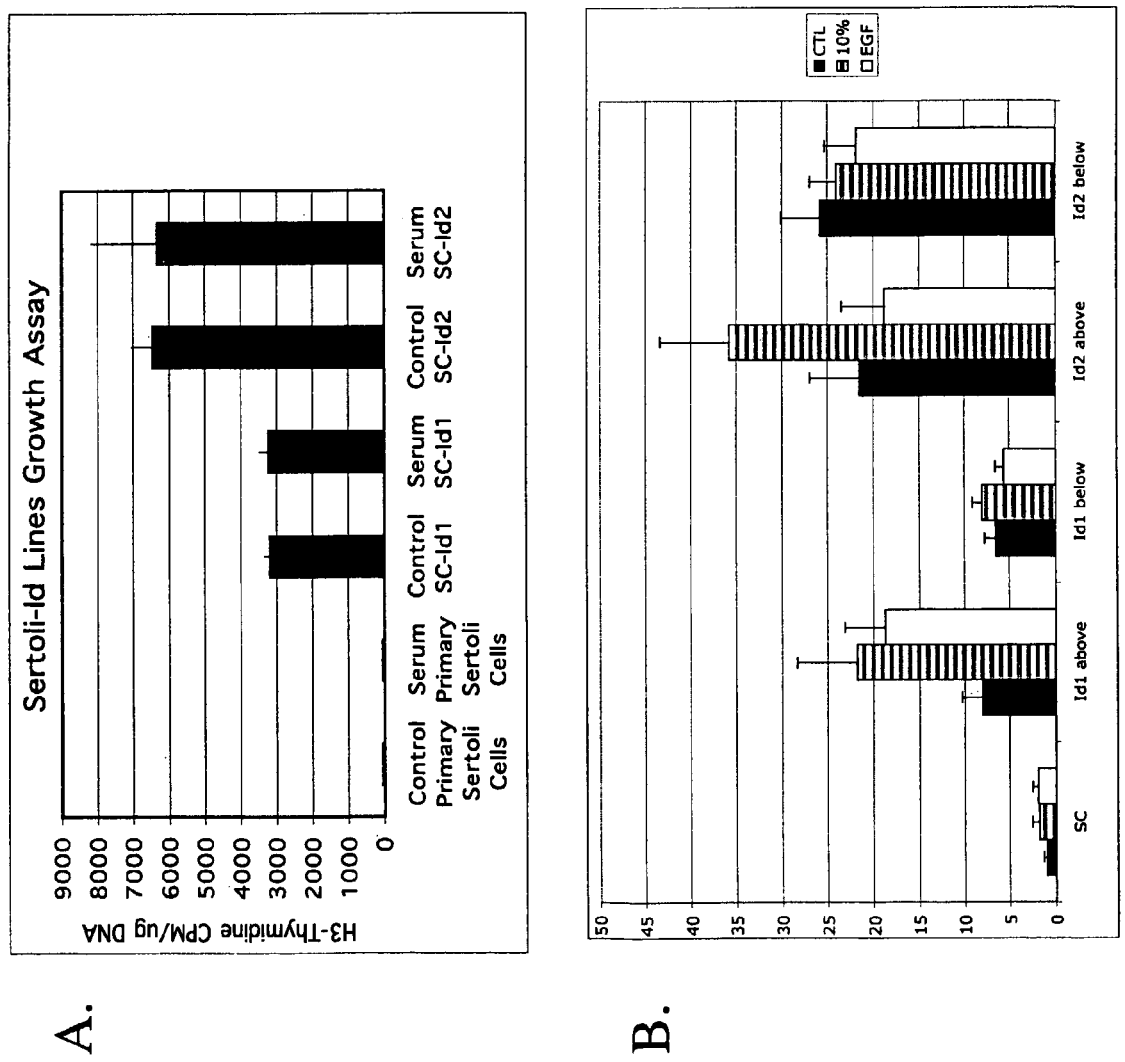
FIG. 1: Graphs showing the effect of Id1 and Id2 over-expression on Sertoli cell proliferation, as described in Example 2, infra. A) Sertoli cell proliferation rate expressed in terms of $^3$H incorporation per microgram of DNA. A representative of three experiments performed in triplicate is shown. B) Sertoli cell proliferation measured above and below 50 doublings in response to growth factors such as EGF and 10% serum.

All scientific and technical terms used in this application have meanings commonly used in the art, unless otherwise specified.

The present invention provides modified cells expressing carrying at least one heterologous gene sequence encoding a protein, or encoding a fragment of the protein, which binds a bHLH (basic helix-loop-helix) protein, or binds a bHLH-containing protein complex, and methods for generating these modified cells.

The present invention also provides pharmaceutical compositions and kits, comprising the modified cells of the invention.

The present invention further provides methods for individual cell therapy and/or co-grafting to a recipient subject, the modified cells of the invention, along with a transplant organ, tissue or cell. Additional methods provided include methods for co-culturing the modified cells of the invention, with other cells, in order to enhance the viability of the other cells. In one embodiment, the modified cells of the invention are co-cultured with thawing, cryo-preserved cells, in order to enhance the viability of the thawing cells.

The invention also provides methods for using the cells of the invention in cell based assays, including high throughput screening assays, for drug discovery.

The Modified Cells of the Invention:

The present invention provides modified cells carrying at least one heterologous gene sequence encoding a protein, or encoding a fragment of the protein, which binds a bHLH (basic helix-loop-helix) protein, or binds a bHLH-containing protein complex, and methods for generating these modified cells. Accordingly, the modified cells are transgenic cells. The modified cells are generated by introducing isolated cells with at least one heterologous gene sequence encoding a protein, or a fragment of the protein, which binds a bHLH or a bHLH complex. The heterologous gene sequence can be expressed in the modified cell in order to cause a change in the differentiated state of the cell. In one embodiment, the heterologous gene sequence is expressed in the modified cell in order to cause the cell to change to a dedifferentiated state or to cause the cell to change to a less differentiated state. In another embodiment, the heterologous gene sequence is expressed in the modified cell in order to cause the cell to change to a more differentiated state. In yet another embodiment, the heterologous gene sequence is expressed in the modified cell, in order to cause the cell to proliferate.

In general terms, differentiation is the process of cellular maturation. The modified cells are generated from isolated cells which are at any differentiated state, including an undifferentiated cell, a differentiating cell, or a terminally differentiated cell (e.g., a mature cell), a dedifferentiated cell, or a mixture of these cells. The modified cells are generated from cells isolated at any cell cycle stage, including pre-mitotic or post-mitotic, or a mixture of these cells.

The modified cell undergoing differentiation or dedifferentiation may undergo at least one cellular change, including changes in the levels and/or compositions of: RNA; proteins (e.g., intracellular, membrane-bound or secreted proteins); lipids; polysaccharides; and/or ionic composition. The differentiating or dedifferentiating cell may undergo changes in metabolic pathways and/or signal transduction pathways. The differentiating or dedifferentiating cell may undergo changes in cellular proliferation. The differentiating or dedifferentiating cell may undergo changes in passage through any stage of the cell cycle, including G0, G1, S, G2 and mitosis. The differentiating or dedifferentiating cell may undergo changes in morphology (e.g, size, shape), granularity, cell receptor composition, or cell adhesion properties. The differentiating or dedifferentiating cell may undergo changes in cell function.

One skilled in the art will recognize the differentiated state or the dedifferentiated state of a cell, by observing and/or monitoring any of these cellular changes using known methods. Thus, the differentiated or dedifferentiated state of the cell is monitored by any means, including visual observation, enzymatic analysis, biochemical analysis, metabolic analysis, functional analysis, fluorescence activated cell sorting (e.g., FACS), immunochemistry, molecular analysis (e.g., DNA, RNA or protein levels), and/or by monitoring cell culture properties.

The modified cells of the invention carry a heterologous gene sequence encoding a heterologous protein, or a fragment of the protein, which binds a bHLH protein or binds a bHLH-containing protein complex. The modified cells produce (i.e. express) the RNA transcript encoded by the heterologous gene sequence and express the heterologous protein. The expressed protein binds a bHLH protein, or binds a bHLH-containing protein complex, inhibiting normal function of the bHLH protein, or of the bHLH-containing protein complex. Thus, cell growth and/or differentiation and/or tumorigenesis of the modified cell is inhibited, and/or cellular apoptosis of the modified cell is mediated.

Transcription of the heterologous gene sequence carried by the modified cells, and/or translation of the heterologous protein, can be inducible with a hormone, a growth factor, or a trophic factor. In one embodiment, transcription and/or translation can be inducible with follicle stimulating hormone (FSH), cAMP, or serum such as bovine calf serum.

The modified Sertoli cells of the invention are generated from Sertoli cells isolated from mammalian male testes using well-known methods (J H Dorrington, et al 1975 Mol Cell Endocrinol 3:57-70; P S Tung, et al 1984 Biol Reprod 30:199-211; Cheng, et al. 1987 J Biol Chem 26:12768-12779). The modified cells of the invention are generated from Sertoli cells isolated from males of any age including fetal, newborn, infant, child, pubescent, adolescent, and/or adult, of any mammalian species including bovine, porcine, murine, equine, canine, feline, simian, human, ovine, piscine or avian.

The isolated Sertoli cells are enriched by separation away from other non-Sertoli testicular cells, including testicular Leydig cells, peritubular cells and germ cells, using conventional techniques. The enrichment methods include removing non-Sertoli cells from the Sertoli cells using proteases and nucleases, including trypsin and DNase, respectively. The enrichment methods further include washing and centrifugation steps. The enrichment methods also include a collagenase step, a hyaluronidase step, and/or a DNase step.

The modified Sertoli cells are generated from Sertoli cells isolated at any cell cycle stage, including pre-mitotic or post-mitotic, or a mixture of these cells. The modified Sertoli cells are generated from Sertoli cells isolated in any state, including an undifferentiated, a differentiating, or a terminally differentiated state, or a mixture of these states. The isolated Sertoli cells are identified by cellular morphology and/or physiology, or the cell cycle, or differentiated state. The isolated Sertoli cells are identified using various cell markers, expression of certain genes (M D Grisold 1988 Int Rev Cytol 110:133-156) and/or Sertoli cell functions. For example, the isolated Sertoli cells can be differentiated Sertoli cells expressing transferrin, an iron-binding protein (M K Skinner, et al 1982 Biol Reprod 27:211-221; M K Skinner, et al 1989 Endocrinology 124:3015-3024; Norton and Skinner 1992). Differentiated Sertoli cells express aromatase, androgen receptor (Bremner et al. 1994), GATA-1 (Ketola et al. 2002), p27kip (Holsberger et al. 2003), SGP-2 (Law and Griswold 1994) and laminin alpha 5 (Schlatt et al. 1996). The modified Sertoli cells can maintain their Sertoli cell functions.

Additionally, the isolated Sertoli cells can function as nutritive supply cells (Bardin et al., 1988 "The Sertoli Cell" in: The Physiology of Reproduction, Knobil, E. and J. Neill (eds). Raven Press, Ltd., New York, pp. 933-947).

The modified Sertoli cells can be freshly isolated cells, primary cell cultures or established cell cultures. The modified Sertoli cells can be cultured in vitro using conventional methods (P S Tung, et al., 1984 Biol Reprod 30:199-211; M K Skinner, et al., 1988 J Biol Chem 263:2884-2890; C J Anthony, et al., 1991 Endocrinology 129:353-360). The modified Sertoli cells can be cultured in a variety of media, including commercially-available media such as Ham F-12 (Sigma), Minimal Essential Medium (MEM, Sigma), RPMI-1640 (Sigma), or Dulbecco's Modified Eagle's Medium (DMEM, Sigma). The culture media can be supplemented with hormones, growth factors (e.g., insulin, transferrin, epidermal growth factor, follicle stimulating hormone and its derivatives including o-FSH-16, cAMP and its derivatives including dibutryl cAMP and $(Bu)_2$cAMP, bovine calf serum, or BSA), salts (e.g., sodium chloride, calcium, magnesium, or phosphate), buffers such as HEPES, nucleotides, antibiotics, trace elements, or a carbon energy source such as glucose. The modified Sertoli cells can be cultured in a medium that includes antibiotic and/or antifungal agents, including penicillin, streptomycin, gentamycin and/or fungizone. The modified Sertoli cells can be cultured under standard conditions including $CO_2$ and under a range of temperatures, including about 28 degrees Celsius to about 37 degrees Celsius. The modified Sertoli cells of the invention can be cultured for a multitude of passages.

In another embodiment, the modified cells of the invention are generated from neurons or muscle cells.

The modified cells of the invention do not become tumorigenic, for example when transplanted into a recipient subject.

The Heterologous Gene Sequence

The modified cells of the invention carry at least one heterologous gene sequence encoding at least one protein. The encoded heterologous protein in the modified cells of the invention can include a helix-loop-helix domain which shares structural homology with the helix-loop-helix domain of a bHLH protein (C Murre, et al 1994 Biochem Biophys Acta 1218:129-135; C Murre, et al., 1989 Cell 56:777-783). The encoded heterologous protein can include a DNA binding domain. The encoded heterologous protein can inhibit the function of a bHLH protein or a bHLH-containing protein complex, by binding to the bHLH protein or complex.

The heterologous gene sequence can encode an Inhibitor of differentiation protein (e.g., an Id protein) such as an Id1, Id2, Id3, or Id4 protein (R Benezra, et al 1990 Cell 61:49-59; R W Deed, et al., 1994 Biochim Biophys Acta 1219:160-162), or a homolog of the Id1, Id2, Id3, or Id4 proteins, or a fragment of an Id protein (M W Quong, et al 1993 Mol Cell Biol 13:792-800 (C Murre, et al 1994 Biochem Biophys Acta 1218:129-135).

The modified cells can be introduced with any number and/or combination of the Id1, Id2, Id3, and/or Id4 gene sequences.

The heterologous gene sequence can also encode a wild-type or a variant heterologous protein, or a fragment of such a protein. The variant heterologous protein can be a codon-usage variant, or a polymorphic, allelic, mutant, homolog, or ortholog variant protein. The present invention also provides a modified cell carrying a heterologous gene sequence encoding a fusion heterologous protein.

The introduced, heterologous gene sequence, including any one of the Id gene sequences, is isolated from any source, including bacterial, yeast, insect, or plant. The introduced gene sequence is isolated from a bovine, porcine, murine, equine, canine, feline, simian, human, ovine, piscine, or avian animal. The modified cells can be introduced with more than one type of Id gene sequences, for example Id gene sequences each isolated from different sources including bovine, porcine, murine, equine, canine, feline, simian, human, ovine, piscine, or avian animals.

The Heterologous Protein Expressed by the Modified Cells Inhibits bHLH Proteins

The present invention provides modified cells expressing at least one heterologous protein, such as an Id protein, which binds and inhibits the normal function of a bHLH protein or a bHLH-containing protein complex. The expressed heterologous protein can bind a bHLH protein which includes a helix-loop-helix domain (C Murre, et al 1994 Biochem Biophys Acta 1218:129-135; C Murre, et al., 1989 Cell 56:777-783). The helix-loop-helix domain of the bHLH protein can bind other bHLH proteins to form a bHLH-containing protein complex.

The expressed heterologous protein binds a first bHLH protein and inhibits the first bHLH protein from binding a second bHLH protein and forming a complex. The expressed heterologous protein can bind to the same or to a different epitope on the first bHLH protein which normally binds with the second bHLH protein. The heterologous protein can bind a naturally-occurring or recombinant bHLH protein. In one embodiment, the heterologous protein can form a dimer, trimer, tetramer, or a higher order protein complex with the bHLH protein.

The bHLH protein can also include a DNA-binding domain. The normal function of the bHLH protein or complex is to form a heterodimer (e.g., bind a second bHLH protein), or bind a transcription factor, in order to mediate transcription activation of gene sequences controlled by a consensus E-box (CANNTG) DNA sequence, contained in many naturally-occurring promoters (A B Lassar, et al., 1991 Cell 66:305-315, M B Einarson and M V Chao 1995 Mol Cell Biol 15:4175-4183; K Langlands, et al. 1997 J Biol Chem 272:19785-19793; D A Loveys, et al. 1996 Nucleic Acids Res 24:2813-2820; M V Barone, et al., 1994 Proc Natl Acad Sci USA 91:4985-4988; E Hara, et al., 1994 J Biol Chem 269: 2139-2145; M Moldes, et al., 1997 Mol Cell Biol 17:1796-1804). The E-box sequence can occur in any naturally-occurring or recombinant promoter, including various tissue-specific promoters, Sertoli-specific promoters, transferrin promoters and other promoters (C Murre, et al., 1989 Cell 56:777-783; C Murre, et al., Cell 58:537-544; J Chaudhary, et al., 1997 Endocrinology 138:667-675; J Chaudhary and M K Skinner 1999 Mol Endocrinol 13:774-786; M A Daggett, et al., 2000 Biol Reprod 62:670-679; T L Goetz, et al., 1996 J Biol Chem 271:33317-33324). It is known that the E-box sequence controls activation of gene sequences that mediate cell growth inhibition, cell differentiation inhibition, tumorigenesis inhibition, or mediate cellular apoptosis.

Additionally, the heterologous protein expressed by the modified cells inhibits a bHLH protein or a bHLH-containing protein complex from binding other transcription factors, such as CREB (e.g., a CRE-binding protein or a cAMP response element-binding protein). The expressed heterologous protein can bind to the bHLH protein or a bHLH-containing complex, inhibiting the bHLH protein or complex from binding the transcription factor, or causing the bHLH protein or complex to bind the transcription factor less efficiently. The expressed Id protein can bind to the same or to a different epitope on the bHLH protein which normally binds with the transcription factor. The transcription factor can mediate transcription activation of gene sequences controlled by the E-box sequence. The transcription factor can act in trans or in cis to activate transcription of gene sequences controlled by the E-box sequence. The transcription factor includes CREB (S Suire, et al., 1995 Mol Endocrinol 9:756-766; J Chaudhary and M K Skinner 1999 Endocrinology 140:1262-1271; J Chaudhary and M K Skinner 2001 Biology of Reproduction 65:568-574).

The heterologous protein expressed by the modified cells can also inhibit a bHLH protein or a bHLH-containing protein complex from binding an adapter protein, such as CBP (cAMP response element-binding protein-binding protein) that mediates transcription activation of gene sequences controlled by an E-box sequence (J C Chrivia, et al., 1993 Nature 365:855-859; J Chaudhary and M K Skinner 2001 Biology of Reproduction 65:568-574) and p300 (R Eckner, et al., 1994 Genes Dev 8:869-884; J Chaudhary and M K Skinner 2001 Biology of Reproduction 65:568-574). The expressed heterologous protein can bind to the bHLH protein or a bHLH-containing complex, at the same epitope that binds the adapter protein, or to a different epitope on the bHLH protein, inhibiting the bHLH protein from binding the adapter protein, or causing the bHLH protein or complex to bind the adapter protein less efficiently.

The bHLH protein inhibited by the modified cells of the invention, includes all the members of the family of bHLH proteins, such as the class A and B bHLH proteins (MW Quong, et al 1993 Mol Cell Biol 13:792-800). The class A bHLH proteins include E2-2 (G Bain, et al 1993 Mol Cell Biol 13:3522-3529), HEB (J S Hu, et al 1992 Mol Cell Biol 12:1031-1042), E47 (J Chaudhary and M K Skinner 1999 Mol Reprod Dev 52:1-8), REB-alpha (J Chaudhary, et al 1999 Biol Reprod 60:1244-1250), and E12 and E47 which are differentially spliced products of the E2A gene sequence (C Murre, et al 1989 Cell 58:537-544). The class B bHLH proteins include MyoD and neuroD (A B Lassar, et al 1991 Cell 66:305-315; M E Massari and C Murre 2000 Mol Cell Biol 20:429-440).

Thus, the present invention provides modified cells that express a protein, such as an Id protein, that inhibits cell growth, inhibits cell differentiation, inhibits tumorigenesis, or mediates apoptosis, of the modified cells. The expressed Id protein acts by 1) inhibiting a first bHLH protein from binding a second bHLH protein; 2) binding the bHLH protein to form an Id-bHLH protein complex, which cannot bind, or binds less efficiently, to an E-box sequence; 3) binding bHLH protein to form an Id-bHLH protein complex, which cannot bind, or binds less efficiently, with other transcription factors; or 4) binding a bHLH protein to form an Id-bHLH protein complex, which cannot bind, or binds less efficiently, with an adapter protein.

Nucleotide Sequences Encoding the Heterologous Protein

In one embodiment, the heterologous gene sequence is a wild-type nucleotide sequence encoding a protein, or a fragment thereof, having bHLH-binding activity. In another embodiment, the heterologous gene sequence encodes a wild-type Id protein or a fragment thereof. The wild-type Id sequence can be mouse (e.g., Id1: 010495; Id2: NM-010496), rat (e.g., Id1: D10862; Id2: D10863), or human (e.g., Id 1: NM-002165; Id2: NM-002166, see also XM 046179, XM 045365, XM 086357, or NM 001546) Id sequences.

In another embodiment, the heterologous gene sequence is a variant nucleotide sequence. The variant sequence can be a codon-usage variant that differs from the wild-type heterologous gene sequence encoding a protein that binds the bHLH, or a fragment of that protein. In one embodiment, the codon-usage variant can be a heterologous gene sequence which differs from the wild-type Id nucleotide sequence, yet does not alter the predicted Id amino acid sequence or biological activity (e.g., ability to bind a bHLH protein). For example, a number of amino acids are designated by more than one triplet. Codons that specify the same amino acid may occur due to degeneracy in the genetic code. Examples include nucleotide codons CGT, CGG, CGC, and CGA encoding the amino acid, arginine (R); or codons GAT, and GAC encoding the amino acid, aspartic acid (D). Thus, a protein can be encoded by one or more nucleic acid molecules that differ in their specific nucleotide sequence, but still encode protein molecules having identical amino acid sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The codon-usage variants may be generated by recombinant DNA technology. Codons may be selected to optimize the level of production of the heterologous protein in the modified cell, in accordance with the frequency of codon-usage utilized by the cell. Alternative reasons for altering the nucleotide sequence encoding a heterologous protein, include the production of RNA transcripts having more desirable properties, such as an extended half-life or increased stability. A multitude of variant nucleotide sequences that encode the respective heterologous protein may be generated, as a result of the degeneracy of the genetic code. Accordingly, the present invention provides selecting every possible triplet codon to generate every possible combination of nucleotide sequences that encode the heterologous proteins, or that encode polypeptides having the biological activity of the heterologous proteins such as the Id1, Id2, Id3, or Id4 proteins.

It will be appreciated by one skilled in the art that variations may exist among individuals within a population due to natural polymorphic or allelic variation. The present invention provides a modified cell which is introduced with a variant, heterologous gene sequence which includes one or more nucleotides that differ from the wild type sequence.

The present invention provides a modified cell introduced with a heterologous gene sequence comprising a polymorphic form of the wild-type Id gene sequence.

Typically, isolated polymorphic forms of naturally-occurring gene sequences are isolated from different subjects of the same species (e.g., intraspecies). The polymorphic forms include sequences having one or more nucleotide substitutions that may or may not result in changes in the amino acid codon sequence. These nucleotide substitutions may encode a protein having the biological activity of the wild-type Id protein (e.g., binds a bHLH protein), or encodes a mutant polymorphic form of the wild-type Id protein having a different or null activity. Any and all such nucleotide variations and resulting amino acid sequences, are within the scope of the invention.

The present invention provides a modified cell introduced a heterologous gene sequence comprising an allelic form of the wild-type heterologous gene sequences. The introduced gene sequence can be an allelic form of the wild-type Id sequences. The allelic forms can be isolated from different subjects of the same species (e.g., intraspecies).

Typically, isolated allelic forms of naturally-occurring gene sequences include wild-type and mutant alleles. For example, a wild-type Id gene sequence will encode an Id protein having normal Id biological activity, such as, for example, binding a bHLH protein. A mutant Id gene sequence may encode an Id protein having an activity not found in normal Id proteins. Alternatively, a mutant Id gene sequence may encode an Id protein having normal activity. The various allelic forms of the heterologous gene sequence may or may not encode a heterologous protein having the same biological activity as the wild-type heterologous proteins.

The present invention provides a modified cell introduced with a heterologous gene sequence comprising a mutant form of the wild-type heterologous gene sequence. The mutant forms can be isolated from different subjects of the same species.

In one embodiment, the mutant heterologous gene sequence can encode a mutant form of the heterologous protein comprising one or more amino acid substitutions, insertions, deletions, truncations, or frame shifts. Such mutant forms of proteins may or may not exhibit the same biological activity as the wild-type heterologous proteins.

The amino acid substitutions can include conservative amino acid changes, where a substituted amino acid has similar structural or chemical properties, such as replacement of leucine with isoleucine. Alternatively, the amino acid substitutions include nonconservative amino acid changes, such as replacement of a glycine with a tryptophan. Guidance in determining which and how many amino acid residues may be substituted, inserted or deleted may be found using computer programs well known in the art, for example, DNASTAR software.

Conservative amino acid substitutions can frequently be made in a protein without altering either the conformation or the biological activity of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered conservative in particular environments.

The amino acid substitutions can be conservative or nonconservative. Guidance in determining which and how many amino acid residues may be substituted in the heterologous protein may be found in the properties of a naturally-occurring heterologous protein, such as an Id protein. These properties include the amino acid length, the physical length, or in the folded conformation. These properties may be derived by prediction (e.g., based on amino acid sequence) and/or experiment (e.g., based on X-ray crystallography). The substituted amino acids are selected so that the properties of the variant heterologous protein, are identical or similar to that of a naturally-occurring heterologous protein.

The present invention provides a variant heterologous gene sequence which is a homolog of the wild-type heterologous gene sequence. A homolog is related to the heterologous gene by descent from a common ancestral gene sequence. A homolog will differ in sequence from the wild-type heterologous gene sequence. The homolog can encode a protein having the same functional activity of the wild-type heterologous protein, such as the Id protein.

The present invention provides a variant heterologous gene sequence which is an ortholog of the wild-type heterologous gene sequence. An ortholog is one of a set of gene homologs that have diverged from each other as a consequence of speciation. An ortholog will differ in sequence from the wild-type heterologous gene sequence. The ortholog can encode a protein having the same functional activity of a wild-type heterologous protein, such as the Id protein.

The present invention provides a variant heterologous gene sequence which is a paralog of the wild-type heterologous gene sequence. A paralog is one of a set of gene homologs that have diverged from each other as a consequence of duplication. A paralog will differ in sequence from the wild-type heterologous gene sequence. The paralog can encode a protein having the same functional activity of a wild-type heterologous protein, such as the Id protein.

Fusion Genes

The present invention includes modified cells carrying a heterologous gene sequence comprising a fusion gene sequence. The fusion gene sequence can encode a chimeric protein comprising the whole or a portion of the heterologous protein from one source fused (e.g., linked or joined) to the same or a different portion of the heterologous protein from the same or another source. The portion can be the N-terminal, the helix-loop-helix, the DNA-binding, or the C-terminal domain, or any combination, or any order of these. The fusion gene sequence can encode a protein comprising at least the helix-loop-helix domain of the heterologous protein, such as the helix-loop-helix domain of the Id protein. Methods of generating fusion gene sequences and proteins are known in the art.

The fusion gene sequence encodes a protein comprising the heterologous protein from one source fused to a non-heterologous gene sequence. The non-heterologous gene sequence includes an epitope tag, such as histidine (His) tags, glutathione-S-transferase (GST) tags, V5 tags, FLAG tags, influenza hemagglutinin (HA) tags, Myc tags, VSV-G tags, or thioredoxin (Trx) tags. The tagged-fusion molecules are useful for facilitating isolation and/or purification the modified hepsin molecule (D R Marshak, et al., 1996 in: "Strategies for Protein Purification and Characterization" pp 396; Kroll, D. J., et al., 1993 DNA Cell Biol 12:441-53).

The fusion gene sequence encodes a heterologous protein fused to a reporter molecule. The reporter molecule can be a full-length protein, or a fragment or derivative thereof. Reporter molecules commonly used include glutathione-S-transferase (GST), horseradish peroxidase (HRP), chloramphenicol acetyltransferase (CAT) beta-galactosidase, beta-glucuronidase (GUS), luciferase, luciferin, anthocyanins, green fluorescent protein (GFP), and autofluorescent proteins including blue fluorescent protein (BFP). The reporter protein can be used to quantify the amount of protein produced in the cell of the invention (C A Rhodes, et al., 1995 Methods Mol. Biol. 55:121-131).

Other fusion gene sequence constructs include maltose binding protein (MBP), S-tag, Lex A DNA binding domain (DBD) fusions, GAL4 DNA binding domain fusions, and herpes simplex virus (HSV) BP16 protein fusions.

The fusion gene sequence can be engineered to encode a proteolytic cleavage site located between the heterologous protein and the non-heterologous protein portion, so that the encoded fusion protein can be cleaved by a protease. The cleavage site provides a method for purifying the heterologous protein away from the non-heterologous protein. The cleavage site can include recognition sequences for the following enzymes: enterokinase, trypsin, chymotrypsin, elastase, thrombin, or V signal peptide.

The different portions comprising the fusion heterologous gene sequence can be isolated from any source, including bacterial, viral, yeast, insect, plant, bovine, porcine, murine, equine, canine, feline, monkey, ape, or human. Alternatively, the different portions comprising the fusion gene sequence can each be wild-type or a variant form including allelic, polymorphic, mutant, homolog, ortholog, or paralog forms, or a mixture of any of these forms.

Generating the Modified Cells of the Invention

The present invention provides methods for generating the modified cells of the invention. To generate the modified cell of the invention, the isolated animal or mammalian cell is introduced with a nucleic acid molecule comprising the heterologous gene sequence (e.g., nucleotide sequence) encoding a heterologous protein, such as the Id protein, using methods known in the art. The heterologous gene sequence encodes a heterologous protein which is full-length, wild-type, or a variant, or any fragment of these proteins, having bHLH-binding activity. The heterologous gene sequence is operably linked to a vector (e.g., an expression vector) that permits expression of the heterologous RNA transcript. In another embodiment, the heterologous RNA transcript is translated to produce the heterologous protein.

Vectors

The present invention provides modified cells generated by introducing isolated cells with a heterologous gene sequence encoding the heterologous protein operably linked to a vector. Suitable vectors are known in the art. Such vectors include, but are not limited to, plasmids, cosmids, and phagemids.

In one embodiment, the vector is an autonomously replicating vector comprising a replicon that directs the replication of the vector within a eukaryotic host cell. In another embodiment, the vector is integrated into the host genome. Various viral vectors may also be used, such as, for example, a number of well known retroviral and adenoviral vectors (Berkner 1988 Biotechniques 6:616-629).

In one embodiment, the vector permits transcription of the heterologous gene sequence in a eukaryotic host cell. In another embodiment, the vector permits translation of the heterologous RNA transcript. The vectors include expression vectors, comprising an expression control element, such as a promoter or enhancer sequence, which enables transcription of the linked heterologous gene sequence and can be used for regulating the expression (e.g., transcription and/or translation) of an operably linked heterologous gene sequence. Expression control elements are known in the art and include, but are not limited to, inducible promoters, constitutive promoters, secretion signals, enhancers, transcription terminators, and other transcriptional regulatory elements. The efficiency of expression may be enhanced by the inclusion of enhancers appropriate to the cell system in use (Scharf, D., et al, 1994 Results Probl. Cell. Differ. 20:125-62; Bittner, et al., 1987 Methods in Enzymol. 153:516-544). Other expression control elements include translation sequences, including and ATG-initiation and termination codons. The ATG-initiation codon is preferably linked in the correct reading-frame with the heterologous gene sequence to ensure transcription and translation of the heterologous gene sequence.

The expression control elements can be of various origins, including naturally-occurring and synthetic. The naturally-occurring elements can be cellular or viral in origin. The expression control element can be a cell-specific promoter, such as a transferrin promoter (M K Skinner, et al., 1989 Endocrinology 124:3015-3024; R L Idzerda, et al., 1989 Cell Biol 9:5154-5162; F Guillou, et al., 1991 J Biol chem. 266: 9876-84; J Chaudhary and M K Skinner 1998 Mol Reprod Dev 50:273-283; J Chaudhary and M K Skinner 1999 Endocrinology 140:1262-1271). The promoter can be a viral promoter including an SV40 early promoter or the promoter contained within the LTR of a retroviral vector. The promoter can be a cytomegalovirus promoter (CMV) (M Boshart, et al., 1985 Cell 41:521-530).

Regulatory sequences may be placed at the 3' end of the coding sequences. These sequences may act to stabilize messenger RNA. Such terminators are found in the 3' untranslated region following the coding sequences in several yeast-derived and mammalian genes.

Commonly used eukaryotic control sequences for use in expression vectors include promoters and control sequences compatible with mammalian cells such as, for example, a CMV promoter and avian sarcoma virus (ASV) (πLN vector). Other commonly used promoters include the early and late promoters from Simian Virus 40 (SV40) (Fiers, et al., 1973 Nature 273:113), or other viral promoters such as those derived from polyoma, Adenovirus 2, and bovine papilloma virus.

The promoter can be inducible, for example regulated by environmental stimuli or the growth medium of the cells, including those from the genes for heat shock proteins, alcohol dehydrogenase 2, isocytochrome C, acid phosphatase, enzymes associated with nitrogen catabolism, and enzymes responsible for maltose and galactose utilization. An inducible promoter, such as hMTII (Karin, et al., 1982 Nature 299:797-802) may be used.

The promoters can be constitutive including yeast beta-factor, alcohol oxidase and PGH promoters. Other constitutive promoters include the cytomegalovirus promoter (CMV) (Boshart, M. et al., 1985 Cell 41:521-530). For reviews, see Maniatis, et al., (1989 Molecular Cloning, in: "A Laboratory Manual", Cold Spring Harbor Laboratory, Cold Spring Harbor, N.Y.) and Ausubel et al. (1989 in: "Current Protocols in Molecular Biology", John Wiley & Sons, New York N.Y.) and Grant et al (1987 in: "Methods in Enzymology" 153:516-544).

Examples of expression vectors for eukaryotic host cells include, but are not limited to, vectors for mammalian host cells including pCIneo (Promega), BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene), retroviral vectors (e.g., pFB vectors (Stratagene)), pCDNA-3 (Invitrogen) or modified forms thereof, adenoviral vectors; Adeno-associated virus vectors, baculovirus vectors, yeast vectors (e.g., pESC vectors (Stratagene)).

Transcriptional control sequences for yeast vectors include promoters for the synthesis of glycolytic enzymes (Hess et al., 1968 J Adv Enzyme Reg 7:149; Holland et al., 1978 Biochemistry 17:4900). Additional promoters known in the art include the CMV promoter provided in the CDM8 vector (Toyama and Okayama, 1990 FEBS 268:217-221); the promoter for 3-phosphoglycerate kinase (Hitzeman et al., 1980 J Bio Chem 255:2073), and those for other glycolytic enzymes.

The vector can include at least one marker gene that confers a selectable marker. The marker gene can encode a gene product that confers drug resistance such as resistance to ampicillin, tetracycline, kanamycin, or neomycin. The vector can include any marker gene. These include, but are not limited to, the herpes simplex virus thymidine kinase (M Wigler et al., 1977 Cell 11:223-32) and adenine phosphoribosyltransferase (I Lowy et al., 1980 Cell 22:817-23) genes which can be employed in tk-minus or aprt-minus cells, respectively. Also, antimetabolite, antibiotic or herbicide resistance can be used as the basis for selection; for example, dhfr which confers resistance to methotrexate (M Wigler et al., 1980 Proc Natl Acad Sci 77:3567-70); npt, which confers resistance to the aminoglycosides neomycin and G-418 (F Colbere-Garapin et al., 1981 J. Mol. Biol. 150:1-14) and als or pat, which confer resistance to chlorsulfuron and phosphinotricin acetyltransferase, respectively (L E Murry, in: McGraw Yearbook of Science and Technology (1992) McGraw Hill New York N.Y., pp 191-196). Additional selectable genes have been described, for example, trpB, which allows cells to utilize indole in place of tryptophan, or hisD, which allows cells to utilize histinol in place of histidine (Hartman, and Mulligan 1988 Proc. Natl. Acad. Sci. 85:8047-51).

The vector also comprises multiple endonuclease restriction sites that enable convenient insertion of exogenous DNA sequences. Methods for generating recombinant expression vectors are well known in the art, and can be found in Maniatis (1989 in: "Molecular Cloning, A Laboratory Manual", Cold Spring Harbor Laboratory, Cold Spring Harbor, N.Y.) and Ausubel et al. (1989 in: "Current Protocols in Molecular Biology", John Wiley & Sons, New York N.Y.).

Methods for Introducing the Heterologous Gene Sequence into the Cells

The modified cells can be generated by introducing a heterologous gene sequence into the isolated cells using any well-known method. For example, vectors can be introduced by calcium phosphate-mediated DNA transfection (Graham and Van der Eb 1973 Virology 52:456-467; M Wigler, et al 1977 Cell 11:223-232) or other cationic-mediated transfection methods, electroporation (E Neuman, et al 1982 EMBO J 1:841-845; G L Andreason and G A Evans 1988 BioTechniques 6:650), microinjection (W F Anderson, et al 1980 Proc Natl Acad Sci USA 77:5399-5403; M R Cappechi 1980 Cell 22:479-488; A Graessman, et al 1979 J Virology 32:989-994). Other methods include cationic lipid methods (J P Behr 1989 Proc Natl Acad Sci USA 86:6982; J P Loeffler 1990 J Neurochem 54:1812), or lipid methods including encapsulation of DNA in lipid vesicles (M Schaefer-Ridder 1982 Science 215:166-168). Still other methods include DEAE-dextran methods (J H McCutchan and J S Pagano 1968 J Natl Cancer Inst 41:351; M I Al-Moslih and G R Dubes 1973 J Gen Virol 18:189; H Luthman and G Magnusson 1983 Nucl Acids Res 11:1295), polybrene-DMSO methods (S Kawai and M Nishizawa 1984 Mol Cell Biol 4:1172; R J Aubin, et al., 1988 Som Cell Mol Genet 14:155), and particle gun methods.

Still other methods include using an adenovirus transcription/translation vector comprising the late promoter and tripartite leader sequence. A nucleic acid sequence can be inserted in a nonessential E1 or E3 region of the adenoviral genome to create a viable virus capable of expressing the protein encoded by the nucleic acid sequence (Logan and Shenk 1984 Proc Natl Acad Sci 81:3655-59). Alternatively, retroviral transfer methods can be used (E Gibloa, et al 1986 BioTechniques 4:504-512).

In one embodiment, the heterologous gene sequence can be introduced into an isolated cell by employing a calcium phosphate method. In another embodiment, the introduced cells can be further treated with hyper osmotic shock conditions (J Chaudhary, et al., 1997 Endocrinology 138:667-675; C A Chen and H Okayama 1988 Biotechniques 6:632-638; J Chaudhary, et al., 2001 Endocrinology 142:1727-1736). Alternatively, the modified cells can be generated by introducing isolated cells with the expression vector which includes the heterologous gene sequence using a cationic liposomal transfection reagent such as DOTAP™ or DOSPER™ (Roche Molecular Biochemicals), or using a non-liposomal transfection reagent such as FuGENE 6™ (Roche Molecular Biochemicals).

The modified cells introduced with and carrying the heterologous gene sequence, are identified by techniques well known in the art. In one embodiment, the cells are selected, lysed and their DNA content examined for the presence of the heterologous gene sequence, using a DNA gel blot method or similar method (Southern 1975 J Mol Biol 98:503; Berent et al., 1985 Biotech 3:208). Alternatively, the heterologous proteins produced from the modified cells of the invention can be assayed via a biochemical assay or immunological method. The presence of the heterologous protein, such as the Id protein, can be assayed using an anti-Id antibody or an Id ligand.

Culturing the Modified Cells of the Invention

The modified cells can be cultured in vitro. The modified cells are cultured under conditions that permit expression of the heterologous RNA transcript or the heterologous protein, within the modified cells of the invention. In one embodiment, the cells can are cultured under suitable conditions that permit inducible expression of the heterologous gene sequence. In this embodiment, the culture conditions include the appropriate inducing compound and/or inducing growth conditions. In another embodiment, the cells are cultured under suitable conditions that permit constitutive expression of the heterologous gene sequence. The modified cells can be cultured in the same medium used to culture the isolated, non-modified cells.

Cultures of the modified cells can be primary cultures or established cultures. In one embodiment, the cultured modified cells are immortalized by viral treatments well known in the art. Other embodiments include cultured, modified cells that are infected with virus-containing medium including SV40 virus or polyoma virus, and a conventional growth medium such as F12/DMEM, for sufficient time to propagate the modified cells. The cultured, modified cells can be infected with a temperature-sensitive mutant of the SV40 virus that permits propagation and promotes differentiation of the cells. The cultured, modified cells can be introduced with an infectious virus cell or an attenuated virus.

In another embodiment, the cultured, modified cells are immortalized by chemical treatments well known in the art, including treatment with N-nitrosylmethylureas, nitrous acid, hypoxanthine, or nitrosamines (I R Freshney in: "Culture of Animal Cells, A Manual of Basic Technique," 3 ed., Chapter 15, Wiley-Liss, New York).

Pharmaceutical Compositions of the Invention

The present invention provides pharmaceutical compositions and kits comprising the modified cells of the invention. The pharmaceutical compositions can also include suitable carriers and adjuvants. These carriers and adjuvants include, but are not limited to, cell culture medium, ion exchangers, alumina, aluminum stearate, lecithin, and serum proteins, such as human serum albumin. The carriers and adjuvants also include buffer substances such as phosphates, glycine, sorbic acid, potassium sorbate, and salts or electrolytes, such as protamine sulfate. Other examples include partial glyceride mixtures of saturated vegetable fatty acids, phosphate buffered saline solution, water, emulsions (e.g. oil/water emulsion), disodium hydrogen phosphate, potassium hydrogen phosphate, sodium chloride, zinc salts, colloidal silica, magnesium trisilicate, polyvinyl pyrrolidone, cellulose-based substances and polyethylene glycol. Typically such carriers include excipients such as starch, milk, sugar (e.g. sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients.

The pharmaceutical compositions are formulated by well known conventional methods including include sterile solutions; tablets, including coated tablets and capsules. Such compositions may also be formulated as a lipid composition, such as, for example, liposomes. The pharmaceutical compositions may be formulated as polymeric compositions, such as polymer microspheres.

Methods and Uses of the Modified Cells of the Invention

The modified cells of the invention, can be administered to a recipient subject in the form of pharmaceutical compositions as therapeutic agents. Alternatively, the modified cells of the invention, can be co-cultured with other cells, to affect properties of these other cells. In addition, the modified cells of the invention can be co-grafted to a recipient subject with a transplant organ, tissue, cell aggregate, or cell, in order to enhance the viability and/or vascularization of the transplanted organ, tissue or cell and/or to reduce rejection of the transplanted organ, tissue or cell. The administration of the modified cells to a subject can be used to treat certain diseases that cause chronic organ damage or degenerative diseases.

The invention provides proliferating, non-transformed cells, such as Sertoli, neuron and muscle cells, that maintain their normal state of differentiation, in contrast to transformed cells, and can be used as target cells in a variety of methods, for example to identify agents that can modify the activity of the cells, providing new therapeutic agents (drugs). In one embodiment, modified Sertoli cells are used in a high-throughput screening (HTS) assay, to identify agents that can increase male fertility by increasing differentiation of these cells.

In one embodiment, modified Sertoli cells expressing a heterologous protein, that binds bHLH protein, are co-cultured with other cells, to enhance the viability of the co-cultured cells. In another embodiment, modified Sertoli cells are administered or co-grafted to a recipient subject with a transplant organ, tissue, cell aggregate, or cell, in order to enhance the viability and/or vascularization of the transplanted organ, tissue, cell aggregate or cell, and/or to treat diseases that cause chronic organ damage.

The transplantation of individual modified cells expressing Id proteins can be used to treat degenerative diseases. For example, in neurodegeneration, lost neurons cannot be replaced. Transplantation of a neuronal cell modified according to the present invention to express an Id protein in effective amounts, can permit neuronal regeneration to occur. Id expression is then "turned off," using, for example an inducible promoter, so that normal neuronal function can resume. Alternatively, myocytes modified according to the methods of the invention to express an Id protein can be used for muscle regeneration. In these methods, Id protein expression is "on" during the regeneration process, and then turned "off," once regeneration is complete to allow for normal tissue function.

The modified cells of the invention can be formulated into pharmaceutical compositions using standard methods and can be administered as cells, or co-grafted to a recipient subject with an organ, tissue or cell, using conventional modes of administration including, but not limited to, intravenous (i.v.) administration, intraperitoneal (i.p.) administration, intramuscular (i.m.) administration, subcutaneous (s.c.) administration, oral administration, administration as a suppository, or as a topical contact, or the implantation of a slow-release device such as a miniosmotic pump.

The pharmaceutical compositions of the invention may be in a variety of dosage forms, which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration, or co-grafting, and dosage regimen for the pharmaceutical compositions of the invention depends upon many factors including, but not limited to the type of organ affected, the type of autoimmune disease being treated, the severity of the disease, and also the subject's health, weight, and age. Accordingly, dosages of the pharmaceutical compositions can vary depending on the subject and the mode of administration.

The pharmaceutical compositions of the invention containing the modified cells, may be administered or co-grafted to a recipient subject, in an appropriate amount, and for a suitable time period (e.g. length of time and/or multiple times) to enhance viability, enhance vascularization or reduce rejection of the co-grafted organ, tissue or cell. Administration or co-grafting of the pharmaceutical compositions of the invention can be performed over various times. The pharmaceutical compositions of the invention can be administered or co-grafted for one or more hours. In addition, the administration of co-grafting can be repeated depending on the severity of the disease, as well as other factors, as understood in the art.

Methods for Co-Culturing and Co-Grafting the Modified Cells of the Invention

The present invention provides methods for enhancing the function, survival, viability and/or vascularization of transplant organs, tissues, cell aggregates, or cells, by co-grafting to the recipient subject the modified cells of the invention and a transplant organ, tissue, cell aggregate, or cell. The modified cells produce a factor, or factors, that enhance the function, survival, viability, vascularization and/or reduce rejection of the co-grafted transplant.

The term "transplant" is used generally herein to mean a transplant organ, transplant tissue, transplant cell aggregate, or transplant cell.

The transplant, which is co-grafted with the modified cells, will exhibit viability to a greater extent than transplants grafted alone or co-grafted with cells other than the modified cells. The enhanced viability of the transplant includes an increase in transplant function, maturation, proliferation, and/or survival. The viability of the transplant can be characterized by detecting and monitoring the normal functions of the transplant. For example, viable pancreatic islet cells are glucose-responsive, produce insulin, and/or proliferate.

In the present invention, the transplant organ includes a whole organ or a part of a whole organ which is removed from a donor subject and transplanted (e.g., grafted) to a recipient subject. The transplant organ includes any type of organ including solid organs. The transplant organ is functioning and/or viable. The transplant organ can produce a hormone, a growth factor, or a trophic factor.

The transplant tissue is a tissue which is removed from a donor subject and grafted to a recipient subject. The transplant tissue can be any type of naturally-occurring or artificial tissue including tissues that are cultured subsequent to removal from the donor subject. The transplant tissue can be any type of tissue amenable to transplantation. The transplant tissue is functioning and/or viable. The transplant tissue can produce a hormone, a growth factor, or a trophic factor.

The transplant cell is a cell which is removed from a donor subject and grafted to a recipient subject. The transplant cell can be cultured subsequent to removal from the donor subject. The transplant cell can be any cell amenable to transplantation. The transplant cell is functioning and/or viable. The transplant cell can produce a hormone, a growth factor, or a trophic factor. The transplant cell can be freshly isolated, cultured, and/or encapsulated prior to grafting to the recipient subject.

In one embodiment, the transplant organ is skin, heart, lung, pancreas, kidney, liver, or brain. In another embodiment, the transplant tissue or cells are pancreatic islet cells, bone marrow, endocrine cells, stem cells, hepatocytes or liver cells, ligaments, tendons or cartilage. The transplant cell also includes cell suspensions and genetically modified cells.

The transplant tissue or cells can be from fetal, neonatal or adult sources.

The transplant can come from any one donor species subject including bovine, porcine, murine, equine, canine, feline, simian, human, ovine, piscine or avian, or from any combination of these species.

The transplant received by the recipient subject can be an autograft, isograft, allograft, or xenograft, or any combination thereof.

The present invention provides transplant organs, tissue, or cells which are isolated from the pancreas, for co-grafting with the modified cells of the invention. The transplant cells can be pancreatic islet cells. The islet cells are isolated by conventional methods including mincing, teasing, comminution and/or collagenase treatment (Field et al., 1996 Transplantation 61:1554; Linetsky et al., 1997 Diabetes 46:1120). The islet cells are separated away from contaminating cells and materials by washing, filtering, centrifuging and/or picking procedures. The islet cells can be isolated using methods disclosed in U.S. Pat. Nos. 5,447,863, 5,322,790, 5,273,904, and 4,868,121.

In another embodiment, the present invention provides transplant tissue or cells isolated from neural or paraneural sources. The neural transplant tissue or cells are isolated using well known methods such as the methods disclosed in: U.S. Pat. No. 5,830,460 (issued to P R Sanberg on Nov. 3, 1998); U.S. Pat. No. 5,849,285 (issued to H Selawry on Dec. 15, 1998); U.S. Pat. No. 6,214,334 (issued to V Lee on Apr. 10, 2001); and U.S. Pat. No. 6,264,943 (issued to Cherksey on Jul. 24, 2001).

Neural sources include: mesencephalic tissue (C A Freed, et al. 1992 New Engl J Med 327:1549-1555; D D Spencer, et al. 1992 New Engl J Med 327:1541-1548; H Widner, et al. 1992 New Engl J Med 327:1556-1563); chromaffin cells (A Bjorklund and U Stenevi 1985 in: Neural Grafting in the Mammalian CNS, Amsterdam, Elsevier, pp 3-11); substantia nigra (S B Dunnett, et al., 1981 Brain Res. 215: 147-161; S B Dunnett, et al., 1981 Brain Res 229:457-470; J M Morisha, et al., 1984 Exp Neurol 84:643-654; M J Perlow, et al., 1979 Science 204:643-647; D E Redmond, et al., 1986 Lancet 8490:1125-27), or striatal lateral eminence cells.

In another embodiment, the transplant tissue is isolated from the central nervous system (CNS) including astrocytes or neurons (Stenevi et al. 1976 Brain Res. 114:1-20; L A Olson, et al., In: Neural Transplants: Development and Function, J R Sladek, et al., eds, Plenum Press, New York, 1984, pp. 125-165; G J Boer, et al., 1985 Neuroscience 15:1087-1109; M Nieto-Sampedro, et al., 1982 Science 217:860-861; M Nieto-Sampedro, et al. 1984 Proc Natl Acad Sci USA 81:6250-6254).

In another embodiment, the transplant tissue or cells are glial cells (G Barbin, et al., 1985 Devel Neurosci 7:296-307; Y Schurch-Rathgeb, et al., 1978 Nature 273:308-309; K Unsicker, et al. 1984 Proc Natl Acad Sci USA 81:2242-2246; P M Whitaker-Azmitia, et al., 1989 Brain Res 497:80-85).

The transplant tissue can be fetal neural tissue (A Bjorklund 1992 Current Opinion in Neurobiology 2:683-689; Isacson, et al., 1986 Proc Natl Acad Sci USA 83:2728-2732; Lindvall, et al., 1990 Science 247:574-577; P R Sanberg, et al., 1994 in: Cell Transplantation for Huntington's disease, R G Landes Company, Boca Raton, Fla., Chapter 4, pp 19-22).

In another embodiment, the transplant tissue or cell can be paraneural cells, such as adrenal chromaffin cells or adrenal medullary cells (A Lieberman, et al., 1990 Adv Tech Stand Neurosurg 17:65-76; O J Lindvall, 1989 Neurol Neurosurg Psychiat, Special Supplement, pp. 39-54; Lindvall et al., 1987 Ann Neruol 22:457-468; R A Bakay 1990 Neurosurg Clin N Amer 1:881-895; K Unsicker, et al., 1978 Proc Natl Acad Sci USA 75:3498-3502; S B Dunnett, et al., 1981 Brain Res 229:457-470; W J Freed, et al., 1980 Ann Neurol 8:510-519; W J Freed, et al., 1983 Science 222:937-939).

The transplant tissue or cells can be fibroblast cells including transgenic fibroblast cells that express an exogenous gene product (F H Gage, et al., 1987 Neuroscience 23:795-807; M B Rosenberg, et al., 1988 Science 242:1575-1578; S Shimohama, et al., 1989 Mol Brain Res 5:271-278).

The transplant organ, tissue or cell is prepared for grafting to the recipient subject using conventional methods. The conventional methods include slicing an organ or tissue, digesting with collagenase, and/or performing gradients to enrich for the desired tissue or the desired cell fraction. The transplant can be removed from a donor subject and transplanted directly to a recipient subject (e.g., freshly isolated transplant).

Alternatively, the transplant tissue or cell can be cultured in vitro, using conventional methods, prior to grafting to the recipient subject. For example, the transplant tissue or cell is cultured according to the methods disclosed in U.S. Pat. No. 5,821,121 or cultured under conditions that reduce antigenic components (1982 Transplant Proc 14:714-23). The transplant tissue or cell can be a primary culture (Roberts et al. 1995 Biology of Reprod. 53:1446-1453). The transplant tissue or cell can be cultured for several passages. The transplant tissue or cell can be an established culture having been passaged many times.

The transplant can be preserved prior to grafting to the recipient subjection. The preservation methods of the transplant organ, tissue and/or cell, include conventional method, such as the methods disclosed in U.S. Pat. No. 6,001,643. The transplant can be a cryo-preserved organ, tissue or cell using the methods disclosed in U.S. Pat. No. 6,303,355.

The transplant and/or the modified cells of the invention can be encapsulated prior to grafting to the recipient subject. The transplant and the modified cells of the invention can be encapsulated together. Alternatively, the transplant and the modified cells of the invention can be separately encapsulated. The encapsulated transplant and the modified cells, are encapsulated using the same, or different methods. The transplant cells and/or the modified cells can be cultured prior to encapsulation.

The transplant and/or modified cells of the invention can be encapsulated in a biological or a non-biological encapsulating material. The encapsulating material is biocompatible. The encapsulating material can be a semi-permeable membrane or a polymer or a barrier that excludes passage of larger molecules or charged molecules. The encapsulating material can be a membrane that excludes inward passage of molecules of the immune system that cause transplant rejection, including immunoglobulin and lytic factors of the complement system. The encapsulating material can permit the inward and outward passage of smaller molecules such as glucose and insulin. In one embodiment, the encapsulating material can be an isolated segment of a small intestine preferably with intact circulation, an omental pouch or a gastric pouch (Amiri, et al. 1990 Arch Surg 125:1472-1474; Bayat, et al. 1995 Surg Res Commun 17:87-91).

In one embodiment, the encapsulating material is a polymeric scaffold, a polymeric sponge or a matrix. The encapsulating material includes reticulated thermoplastics such as acylnitrile vinyl chloride copolymer (PAN-PVC) and hydrogels. The transplant cells and/or the modified cells can be encapsulated using an alginate-polyamino acid method prior to grafting (U.S. Pat. No. 6,303,355). Alternatively, the transplant cell and/or the modified cells are encapsulated and/or grafted to the recipient subject using the methods disclosed in the following U.S. Pat. Nos. 5,531,997; 5,620,883; 6,080,412; 6,262,255; 6,303,355; and 6,365,385.

The transplant cells and/or the modified cells of the invention can be grafted to the recipient subject as fused transplant cells or fused, modified cells. The fused transplant cells and/or the fused modified cells are generated using conventional methods (U.S. Pat. No. 4,822,470 Chang, et al, issued Apr. 18, 1989; U.S. Pat. No. 4,955,378 Grasso, et al, issued Sep. 11, 1990; U.S. Pat. No. 5,827,736 Heller, et al, issued Oct. 27, 1998). The fused transplant cells maintain the desirable characteristics of the transplant cell. In one embodiment, the fused transplant cells are capable of maintaining the function of the transplant cells, including replacing or augmenting the non-functioning cell, tissue or organ. The fused, modified cells maintain the desirable characteristics of the modified cells.

The fused, modified cells express a heterologous protein, such as an Id protein. The fused, modified cells inhibit rejection of the co-grafted transplant or the co-grafted fused transplant cell, in the recipient subject.

It will be appreciated by one skilled in the art that these grafting methods can be modified for the methods of the present invention.

In the methods of the present invention, the effective amount of transplant grafted to the recipient subject is dependent upon the type of organ, tissue or cell transplant. The amount can also be dependent upon the type of disease or condition to be treated, and the age and health of the subject. Additionally, the amount of the transplant to be grafted is dependent upon the source, such as autograft, isograft, allograft, or xenograft. One of ordinary skill in the art can determine the effective amount using conventional methods.

The transplanted cells can be pancreatic islet cells. The dose of transplanted islet cells is about 6,000 to about 8,000 cells. The dose of the islet cells is equivalent to about 150 micro meters in size per kilogram of the recipient subject body weight. The dose of the islet cells to be grafted is based on recommendations of the International Islet Transplant Registry (Third Medical Department, University Hospital Giessen, D-35385, Giessen, Germany).

The transplanted cells can be allograft pancreatic islet cells that are grafted to the subject in an amount of about 1 to 1000, or 1 to 10, or 10 to 20, or 20 to 30, or 5 to 20 cells/gm body weight. In another embodiment, xenograft islet cells are grafted to the subject in an amount of about 20 to 1000, or 40 to 1000, or 60 to 1000, or 80 to 1000, or 100 to 1000 cells/gm body weight.

The transplant and the modified cells of the invention are co-grafted in the recipient, to the location of the non-functioning or the reduced-functioning organ, tissue or cell, such as the pancreas, brain, renal subcapsular space or subcutaneous facie, pituitary, liver, parathyroid, thyroid, ovary, and brain. The graft location includes the peritoneal cavity or the brain of the subject.

The transplant and modified cells of the invention are co-grafted to the recipient subject using conventional methods that are appropriate for the type of transplant, the location of grafting, the disease or condition to be treated, and the health and age of the patient. The grafting methods include surgical implantation such as stereotaxic surgery. The grafting methods also include injection methods such as parenteral, subcutaneous, intraperitoneal, intravenous, intramuscular. The grafting methods also include slow-release procedures using a miniosmotic pump. Prior to grafting, it may be desirable to anesthetize the recipient subject using local or general anesthesia according to conventional techniques.

The co-grafting methods can be based on well-known methods for co-implanting non-modified cells with islet cells, including the methods disclosed in U.S. Pat. No. 5,958,404 (issued to H P Selawry on Sep. 28, 1999). Other grafting methods include co-implanting into the abdominal testicular region, renal, or subcapsular space of the recipient subject (H P Selawry and D F Cameron 1993 Cell Transplant 2:123-129; G S Korbutt, et al., 2000 Diabetlogia 43:474-480; W Suarez-Pinzon, et al., 2000 Diabetes 49:1810-1818). Other methods include co-implanting cell aggregates of the modified cells and islet cells (S Korbutt, et al., 1997 Diabetes 46:317-322), or implanting cells encapsulated with islet cells (H Yang and J R Wright 1999 Transplantation 67:815-820).

Another method includes co-culturing the modified cells and islet cells prior to co-implantation (G Luca, et al., 2000 J Investig Med 48:411-448).

The co-grafting methods can also be based on well-known methods for implanting tissue or cells into the brain, or co-implanting non-modified cells with neural or paraneural cells into the brain of a recipient subject (E-O Backlund, et al., 1985 J Neurosurg 62:169-173; O Lindvall, et al., 1987 Ann Neurol 22:457-468; I Madrazo, et al., 1987 New Engl J Med 316:831-834; and also U.S. Pat. No. 5,830,460 issued to P R Sanberg on Nov. 3, 1998; U.S. Pat. No. 5,849,285 issued to H Selawry on Dec. 15, 1998; U.S. Pat. No. 6,214,334 issued to V Lee on Apr. 10, 2001; U.S. Pat. No. 6,264,943 issued to Cherksey on Jul. 24, 2001).

The grafting methods include co-implanting modified cells and bovine adrenal chromaffin cells into rat brain (P R Sanberg, et al., 1996 Nat Biotechnol 14:1692-1695). Other grafting methods include co-implanting cells and neuronal tissue (A E Willig, et al., 1999 Brain Res 822:246-250). Yet other methods include injecting a co-suspension of non-modified cells and ventral mesencephalic cells (A I Othberg, et al., 1998 Neurosci Lett 247:111-114). Another method includes co-grafting modified cells and neuron-like cells to a lesioned striatum (A E Willig, et al., 1999 Brain Res Bull 48:441-444).

Alternative methods include grafting non-modified cells to the brain. The grafting methods can be used to relieve hemi-parkinson symptoms in male rats (P R Sanberg, et al., 1997 Nat Med 3:1129-1132) or female rats (C V Borlongan, et al., 1997 Exp Neurol 148:388-392). Other methods include intrastriatal grafting of modified cells (H W Liu, et al., 1999 Brain Res 838:227-233).

The transplants are grafted to the recipient subject prior to, during, or subsequent to the grafted modified cells of the invention. The transplant can be grafted simultaneously, essentially simultaneously, or sequentially with the modified cells of the invention.

The transplant is grafted to the recipient subject in proximity or in juxtaposition to the modified cells of the invention. The transplant and modified cells of the invention can be grafted as an aggregation or mixture of the two. The transplant and modified cells of the invention can be grafted to the recipient subject at different locations in or on the subject.

The methods of the invention further provide administering to the recipient subject an agent that will give therapeutic relief of the condition or disease to be treated. The agent can be a hormone, a growth factor, or a trophic factor, and can be produced by the grafted transplant or modified cell of the invention. The agent is administered in an amount sufficient to provide the subject with therapeutic relief of the condition or disease to be treated. The agent can also be administered prior to, during, or subsequent to grafting the transplant and/or modified cells of the invention.

The methods of the invention further provide administering to the recipient subject an immunosuppressant for a time sufficient to permit the grafted transplant to become functional. The immunosuppressant is administered prior to, during, or subsequent to grafting the transplant and/or modified cells of the invention. The immunosuppressant can be administered for about 40 to 100 days, or for about 50 to 60 days.

The immunosuppressant includes but is not limited to, corticosteroids, cyclosporine, prednisone, azathioprine, methotrexate, cyclophosphamide, lymphocyte immune globulin, anti-CD3 antibodies, Rho (D) immune globulin, adrenocorticosteroids, sulfasalzine, FK-506, methoxsalen, mycophenolate mofetil (CELLCEPT™), horse anti-human thymocyte globulin (ATGAM™), humanized anti-TAC (HAT™), basiliximab (SIMULECT™), rabbit anti-human thymocyte globulin (THYMOGLOBULIN™), sirolimus, thalidomide, Anti-human IL-2 R mAb, tacrolimus, despergulin, TNFα blockers or antagonists or any other biological agent targeting any inflammatory cytokine, nonsteroidal anti-inflammatory drugs/Cox-2 inhibitors, hydroxychloroquine, sulphasalazopryine, gold salts, etanercept, infliximab, rapamycin, mycophenolate mofetil, tacrolismus, basiliximab, cytoxan, interferon beta-1a, interferon beta-1b, glatiramer acetate, mitoxantrone hydrochloride, anakinra and/or other biologics.

The immunosuppressant can be administered in an amount of about 0.5 to about 200 mg/kg/body weight or about 5 to about 40 mg/kg/body weight.

The modified cells of the invention can provide a cellular factor or factors which suppress the recipient subject's immune response against the transplant. Thus, grafting the modified cells and transplant are useful for practicing other methods, including inhibiting transplant rejection, inhibiting graft versus host disease, tolerizing a subject, and treating a disease or condition.

The present invention also provides methods for inhibiting rejection of the transplanted organ, tissue or cell in the recipient subject. The methods comprise grafting to the recipient subject the modified cells of the invention and grafting the transplanted organ, tissue or cell. In one embodiment, inhibiting rejection of the transplant encompasses inhibiting the complete loss, or nearly complete loss, of the viable transplant in the recipient subject. The rejection can be caused by the recipient's immune system involving immunoglobulins, macrophages, proteins, lymphokines, toxic factors released by lymphokines, and/or lytic factors of the complement system.

The methods of the present invention can be used for inhibiting graft versus host disease in subject, comprising grafting a transplant and grafting the modified cells of the invention to the recipient subject.

The methods of the present invention can be used for tolerizing a recipient subject, where the tolerized subject shows a reduced transplant rejection. This method comprises: grafting an initial transplant and grafting the modified cells of the invention to the recipient; and grafting a subsequent transplant to the recipient subject. The subsequent graft may be at the same site as the initial site or at a different (e.g., secondary) site.

The methods of the present invention can be used for treating a subject suffering from a disease or condition associated with a loss of a normal function of an organ, tissue or cell. The methods comprise: grafting a functioning organ, tissue or cell that will replace or augment the non-functioning organ; and grafting the modified cells of the invention. The modified cells, so grafted, provide a cellular factor or factors which suppress the subject's immune response against the functioning grafted organ, tissue or cell, thereby inhibiting transplant rejection so that the transplanted organ, tissue or cell can function to treat the disease or condition. In one embodiment, the disease to be treated is diabetes mellitus.

It has been previously shown that co-grafting non-modified cells and islet cells will increase vascularization of the islet cells (U.S. Pat. No. 5,958,404 issued to H P Selawry on Sep. 28, 1999). The present invention provides methods for enhancing vascularization of the transplant in the recipient subject, comprising grafting to the recipient subject the transplant and the modified cells of the invention. The modified cells of the invention produce a cellular factor(s) that enhance vascularization (e.g., angiogenesis) of the transplant in the recipient subject. The transplant grafted with the modified cells of the invention vascularize faster and/or to a greater extent than transplants grafted alone or grafted with cells other than the modified cells.

The modified cells produce a factor, or factors, that enhance the viability of co-cultured cells (U.S. Pat. Nos. 5,702,700; 5,725,854; 5,759,534; 5,830,460; and 5,849,285). The present invention also provides methods for enhancing the viability of cultured cells, comprising co-culturing the cultured cells with the modified cells of the invention.

The present invention also provides methods for enhancing the viability of cells which have been preserved by freezing or cryo-preservation techniques, comprising co-culturing thawed, frozen or cryo-presevered cells with the modified cells of the invention.

The frozen, thawed or cryo-preserved cells include cells from any organ, such as skin, heart, lung, pancreas, kidney, and liver, and other cells including bone marrow, stem cells, ligaments, tendons, cartilage, cell suspensions, and genetically modified cells. The cells can be germ cells, including sperm cells and oocytes. The cells can be endocrine cells, including pancreatic islet cells (fetal, neonatal or adult), hepatocytes, parathyroid cells, Leydig cell, or ovarian cell. The cells can be nerve or brain cells, such as ventral mesencephalic tissue, chromaffin cells, striatal lateral eminence cells, adrenal chromaffin cells, and other sources of neural cells. The cells can be transgenic cells introduced with any heterologous gene sequence.

The modified cells of the invention, and the frozen, thawed or cryo-preserved cells are co-cultured using conventional methods, including culturing on solid medium (e.g., agar-solidified), or cell suspension.

The frozen cell is preserved using any conventional method. The freezing method (e.g., cryo-preservation method) includes freezing the cells in a freezing medium comprising a growth medium and another liquid that inhibits ice formation; and storing the frozen cells at temperatures ranging from about −80 to about −196 degrees C.

The frozen cell can also be preserved by freezing in a medium comprising an antibiotic, an anti-oxidant, an anti-cytokine, and/or an anti-endotoxin (see U.S. Pat. No. 6,303,355 issued to Opara on Oct. 16, 2001).

The modified cells of the invention are grafted to the recipient subject with cells or tissue for enhanced vascularization cells for enhanced viability, or cells that have been thawed, in an amount sufficient to enhance the vascularization or viability of the grafted transplant cells or tissue. In one embodiment, the modified cells of the invention are grafted in an amount about $10^1$ to about $10^{10}$ cells, or about $10^5$ to about $10^{10}$ cells.

The present invention provides pharmaceutical compositions and kits, comprising the modified cells of the invention expressing a heterologous protein such as an Id protein, and a suitable carrier. The kits may further include cells for co-culture with the modified cells of the invention including frozen, thawed or cryopreserved cells or tissue, or cells or tissue for vascularization, and a suitable carrier. The kits may comprise a transplant organ, tissue and/or cell, and the modified cells of the invention, and a suitable carrier described supra. The pharmaceutical compositions are formulated and may be in the various forms as described supra. The pharmaceutical compositions may be administered to the recipient subject using the various modes described supra.

The following examples are presented to illustrate the present invention and to assist one of ordinary skill in making and using the same. The methodology and results may vary depending on the intended goal of treatment and the procedures employed. The Examples are not intended in any way to otherwise limit the scope of the invention.

EXAMPLE 1

The following provides a description of the methods used to isolate Sertoli cells from rats.

The Sertoli cells were isolated using a modified version of well-known methods (J H Dorrington, et al 1975 Mol Cell Endocrinol 3:57-70; P S Tung, et al 1984 Biol Reprod 30:199-211; Cheng, et al. 1987 J Biol Chem 26:12768-12779). Sterile conditions were maintained throughout the isolation procedure (e.g., a sterile hood was used, when appropriate). All animal use and procedures were approved by the Washington State University Animal Care Committee.

Sertoli cells were isolated from dissected testes from 50 male, 20 day old rats. The tunica albuginia and testicular vein were removed from each dissected testes. The testes were placed in HBSS medium (Hank's Balanced Salt Solution; catalog no. 14170, Gibco), chopped using a razor, until the tissue appeared homogenously chopped. The chopped testes tissue was transferred to a sterile conical tube containing 5 mls of 2.5% trypsin, 1 ml DNAase (Sigma) (10 mg DNAase and 3 ml HBSS). The volume was brought to 50 ml using HBSS. The tube was inverted several times until the tissue lumps disappeared. The tube was vertically submerged and shaken gently in a 37 degree water bath for 20 minutes.

A trypsin inhibitor solution was prepared by dissolving 1.4 mls trypsin inhibitor powder (Invitrogen) in HBSS (bring volume to 13 ml). The trypsin inhibitor powder was allowed to dissolve slowly. At the end of 20 minutes, the tube was removed from the water bath, and the contents of the tube (e.g., cells) were allowed to settle by gravity for 10 minutes. The supernatant was carefully aspirated. The trypsin inhibitor solution was added to the tube and mixed gently by inverting several times. The cells were allowed to settle by gravity for 10 minutes. The supernatant was discarded. The cells were washed four times as follows. The volume was brought to 50 mls with HBSS; the cells were mixed gently by inverting several times; and the cells were allowed to settle by gravity for 10 minutes. After the fourth wash, the supernatant was aspirated. Two mls of collagenase (50 mg collagenase (Sigma) and 4 mls HBSS) and 1 ml of DNAase, were added to the tube, and the volume was brought to 50 mls with HBSS. The tube was shaken gently for 20 minutes in a 37 degree water bath. The tube was removed from the water bath and the cells were allowed to settle by gravity for 10 minutes. At this point, the supernatant contained peritubular cells. The supernatant was transferred to a second sterile conical tube (e.g., "PC" cells). The PC tube was set aside. The pellet in the first tube (e.g., containing the Sertoli cells) was treated with 2 mls hyaluronidase solution (100 mg hyaluronidase (Sigma) and 4 mls HBSS), and shaken gently in a 37 degree water bath for 20 minutes.

The tube containing the peritubular cells was processed further. The volume was brought to 50 mls with HBSS. The tube was centrifuged gently for 2 minutes to pellet the Sertoli cells. The supernatant was transferred to a new conical tube and the pellet was discarded. The peritubular cells were collected by moderate centrifugation for 6 minutes. The supernatant was discarded. The pellet was re-suspended in HBSS and plated in F12 medium containing 10% calf serum. The typical yield of peritubular cells was about 10×150 mm dishes plated. The cells were incubated at 32 degrees C.

The first tube, containing the Sertoli cells, was removed from the water bath after 20 minutes. The Sertoli cells were allowed to settle by gravity for 10 minutes. The supernatant was discarded. The volume was brought to 50 mls with HBSS and the Sertoli cells were mixed by gentle inversion. The Sertoli cells were allowed to settle by gravity for 10 minutes. The Sertoli cells were washed five times. The wash steps included: the volume was brought to 50 mls with HBSS; the Sertoli cells were mixed gently by inverting several times; and the Sertoli cells were allowed to settle by gravity for 10 minutes. After the fifth wash, the tube was gently centrifuged for 4 minutes. The supernatant was discarded. The pellet is highly enriched for Sertoli cells. The pellet was re-suspended in HBSS at a ratio of 1:5 [volume:volume]. The Sertoli cells were plated in F12 medium. The Sertoli cells were incubated at 32 degrees C.

The isolated Sertoli cells were more than 98% pure and were plated under serum-free conditions. Cells were maintained in a 5% $CO_2$ atmosphere in Ham's F-12 medium (Life Technologies, Inc., Rockville, Md.) at 32 degrees C. Sertoli cells were treated with either FSH (250 ng/ml; o-FSH-16, National Pituitary Program, Torrance, Calif.), dibutryl cAMP (200 µM), 10% bovine calf serum, or vehicle alone (Ham's F-12, control). These concentrations of FSH and cAMP have previously been shown to optimally stimulate cultured Sertoli cell differentiated functions (Anthony et al. 1991; Skinner et al. 1988). Cell number, purity, and viability did not change during the culture, in the absence or presence of treatment.

EXAMPLE 2

This Example provides a description of the methods used to generate modified Sertoli cells carrying a heterologous gene sequence encoding an Id1 or Id2 protein.

Plasmids

The eukaryotic expression plasmid pCI-neo-Id1 and Id2 were constructed. The human Id1 (GenBank Accession No. NM-002165) and Id2 (GenBank Accession No. NM-002166) sequences were used to design PCR primers which were then used to amplify the full length coding region from RNA extracted from cell lines.

```
Primers:
human Id-1 (5'):
GCC AAG AAT CAT GAA AGT CGC CAG TGG CAG human Id-1 (3"):
GGG AGG CGC TTC AGC GAC ACA AGA T human Id-2 (5'):
CGC GGT CAG CAT GAA AGC CTT CAG TCC human Id-2 (3'):
CAC CGC TTA TTC AGC CAC ACA GTG CTT TGC
```

Figure 6:
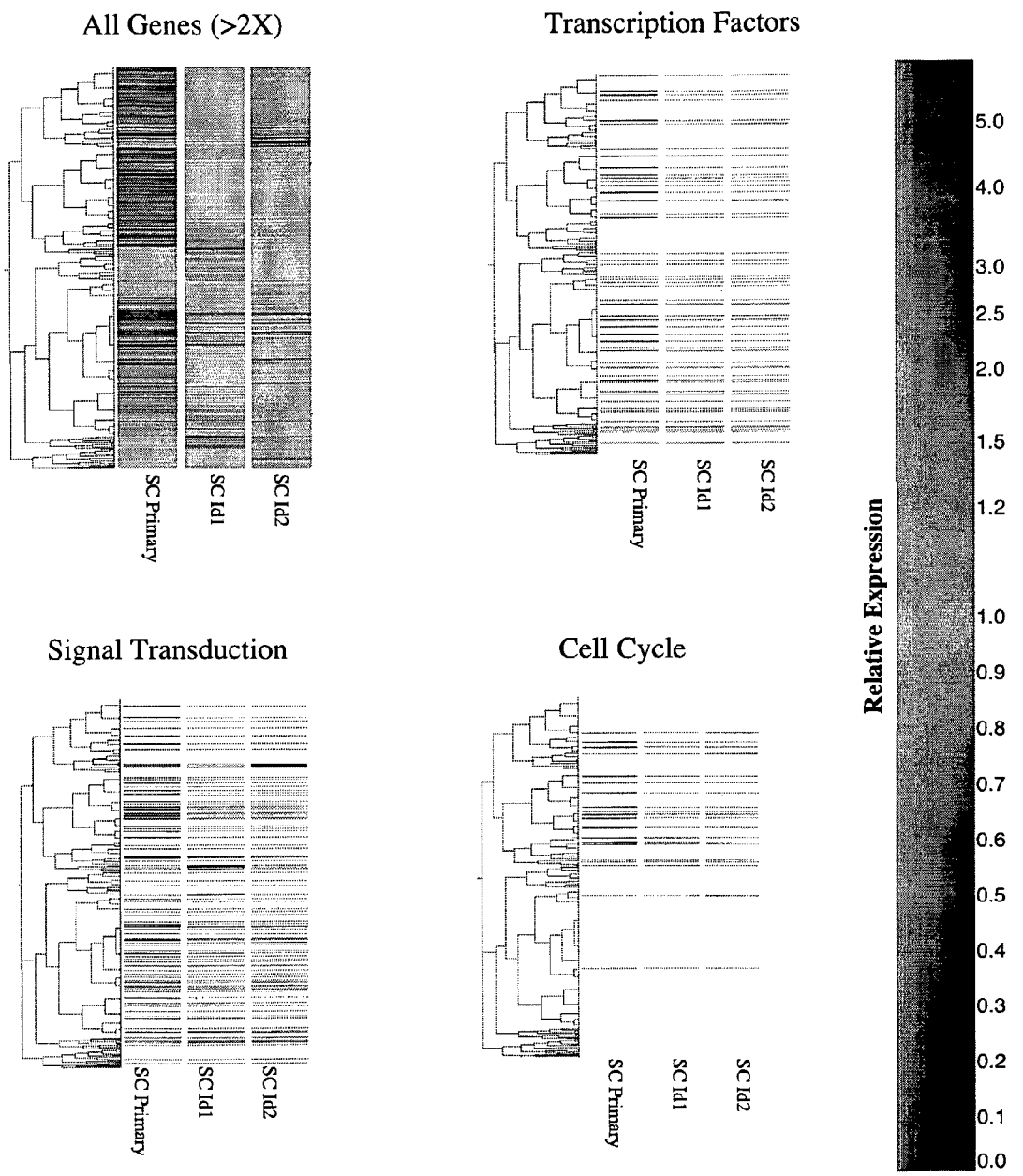
FIG. 6: Gene tree dendrogram smooth correlation cluster analysis of changes in the transcriptomes of primary Sertoli cells (SC Primary), Sertoli cell-Id1 (SC-Id1) and Sertoli cell-Id2 (SC-Id2) at 80 doublings, as described, infra.
Figure 7:
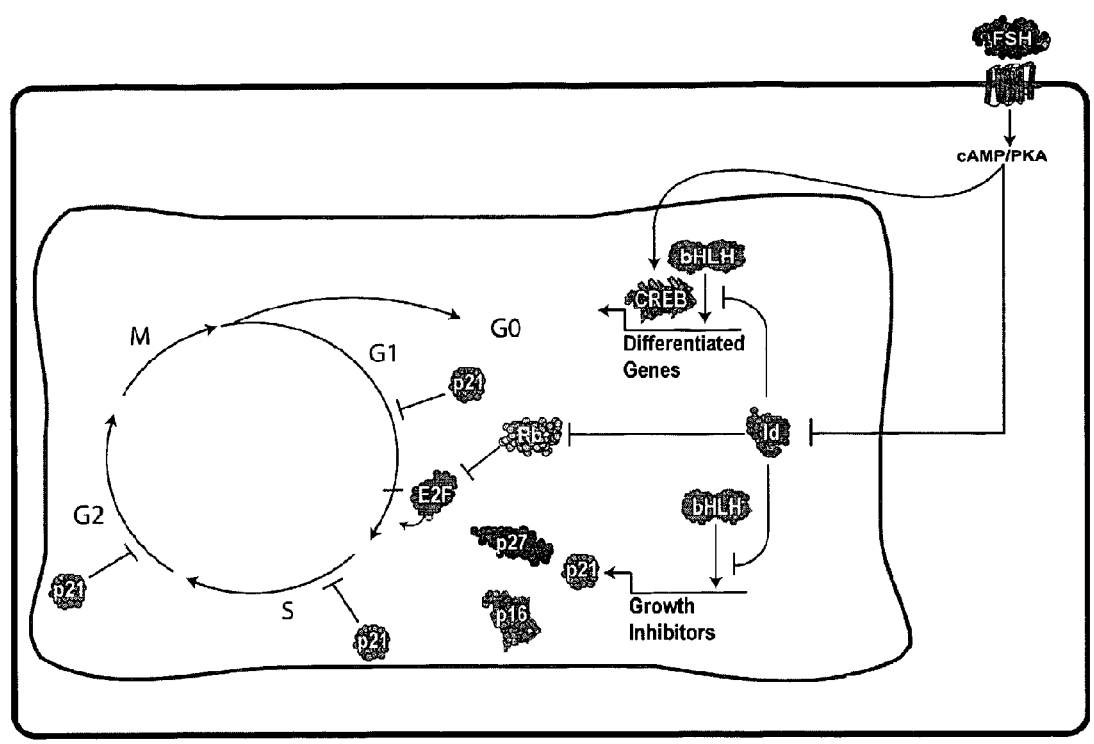
FIG. 7: Schematic of proposed ID interactions with the cell cycle proteins and cell differentiation proteins in the Sertoli cell, as described, infra.

The coding sequences of Id1 and Id2 were obtained through RT-PCR of human cell line RNA. RNA was extracted from human cell lines SKOV3 (ATCC catalog no. HTB77) and OCC1 (W S F Wong, et al., 1990 Gynecological Oncology 38:37-45). The fragments were first subcloned in a pGEM-T-EZ (Promega Corp.) plasmid. The pGEM-T-EZ plasmids containing the Id1 and Id2 fragments were digested with EcoRI, and the resulting fragment was ligated into EcoRI-digested pCIneo expression plasmid (catalog no. E1841, Promega Corp.). The nucleotide sequences of the human Id1 and Id2 gene sequences cloned in the pCIneo expression plasmid are shown in FIGS. 6 and 7, respectively.

Generating Stably Integrated Sertoli Cell Lines

Rat Sertoli cells were cultured in 24-well plates at the density of $10^6$ cells for 48 hours and then transfected with the Id1 or Id2 expression plasmid (described above) by the calcium phosphate method coupled with hyper osmotic shock (10% glycerol).

Briefly, 1.5 micrograms of the plasmid in 150 microliters transfection buffer (250 mM CaCl2, mixed 1:1 vol/vol with 2× Hebes (28 mM NaCl, 50 mM HEPES, and 1.47 mM Na2HPO4, pH 7.0)) was added to each well of a 24-well plate containing $1 \times 10^6$ Sertoli cells in 1 ml Ham's F-12 with 0.01% BSA and incubated at 32 degrees C. for 4 hours. The cells were subjected to a hyper osmotic shock. The medium was aspirated, and 1 ml of 10% glycerol in HBSS (Life Technologies, Inc.) was added. The cells were incubated for 3 min and the wells were washed twice with HBSS before fresh Ham's F-12 was added. Seventy-two hours after transfection the transformed cells were subjected to G418 selection (0-500 micrograms/ml). The transformed cells were subsequently maintained in the Ham's F12 medium containing 43 microM of G418. At this concentration of G418 (43 microM), all the primary non-transformed Sertoli cells failed to survive.

The cells were routinely reseeded at a concentration of $1-4 \times 10^5$ cells in 100-mm tissue culture dishes and incubated in the medium described above. Clones were maintained in the medium and passaged at 10% confluency on 60-mm tissue culture dishes. In vitro growth curves were obtained by plating the transformed cells in 100 mm plates at $10^5$ cells/plate. Cells were grown to confluency, trypsinized, counted and plated at a 1:4 dilution in new 100 mm plates.

Cell Proliferation Assay

The proliferation rate assays, as reflected by rate of DNA synthesis, were performed using $^3$H-thymidine incorporation assays.

Briefly, $10^4$ cells/well were seeded in 24-well plates. Twenty-four hours after the seeding, or when the cells reached ~50% confluency, the cells were incubated with $^3$H-thymidine at 32 degrees C. for 5 hours. Cells were subsequently washed with PBS, 10% TCA and 100% ethanol, and then dissolved with 0.55 NaOH at 37 degrees C. for 30 min. Radioactivity in the samples was determined by liquid scintillation counting. The amount of DNA in the well was assessed, and data expressed as thymidine incorporation per microgram DNA.

Western Blotting and Immunoprecipitation

Sertoli cells, peritubular cells and Sertoli cell lines, were cultured in 150-mm plates and were treated with either FSH, cAMP, serum or vehicle alone (control). After 72 hours of treatment the cells were washed twice with HBSS and lysed with 1 ml M-PER lysis buffer (Pierce Chemical Co., Rockford Ill.) supplemented with miniprotein protease inhibitor cocktail (Boehringer Ingelheim GmbH, Indianapolis, Ind.) at 4 degrees C. for 30 min. Lysates were centrifuged at 10,000×g for 30 min at 4 degrees C., and supernatants collected. The protein concentration in the supernatants was estimated using Bradford's assay (Bio-Rad Laboratories, Inc., Hercules, Calif.). Approximately 50-150 micrograms of protein in SDS sample loading buffer was boiled for 5 min and separated by electrophoresis on a 4-20% gradient mini-SDS gel (Bio-Rad Laboratories, Inc.). The protein was subsequently transferred onto a nitrocellulose membrane and probed with specific antibodies to Id1, Id2, Id3, and Id4 (Santa Cruz Biotechnology, Inc., Santa Cruz, Calif.). The specific antigen-antibody complex was visualized using an alkaline phosphatase chemiluminescent detection kit (Bio-Rad Laboratories, Inc.).

RNA Preparation

Freshly isolated, cultured or transformed Sertoli cells were lysed directly using Trizol Reagent (Invitrogen). The cell lysate was passed several times through a Pasteur pipette to form homogenous lysate. Total RNA was isolated from the cell lysate, following the manufacturer's protocol for RNA isolation using Trizol Reagent. The final RNA pellet was dissolved in distilled water at a concentration of 1.5 mg/ml.

PCR Analysis

Total RNA (2 microgram) was reverse transcribed in a final vol of 25 microliter containing 20 U RNasin (Promega Corp., Madison, Wis.); 0.0625 mM each of dNTP's; 1 microgram oligo dT (Pharmacia, Peapack, N.J.), 10 microM dithiothreitol, and 200 U MMLV reverse transcriptase (Life Technologies, Inc.) in the MMLV first-strand synthesis buffer supplied by the manufacturer (Life Technologies, Inc.). The RNA and oligo dT primer in the buffer were denatured for 10 min at 65 degrees C., then cooled on ice before addition of nucleotides and enzyme. The reverse transcriptase reaction was carried out at 42 degrees C. for 1 hour. PCR was performed using the GeneAmp kit (Perkin-Elmer Cetus, Norwalk, Conn.) with 30 cycles as follows: 94 degrees C, 1 min (denaturation); 58 degrees C., 2 min (primer annealing); and 72 degrees C., 1 min (primer extension). Each PCR reaction contained 250 pg reverse-transcribed DNA, 1 microM of each 5' and 3' oligonucleotide primers; 0.5 U Taq polymerase (AmpliTaq, Perkin-Elmer Cetus), 0.025 mM of each dNTP's. The primer pair sequences used were obtained from published sequences of Id1 and Id2, rat cyclophilin (Ib15), transferrin, GATA4, androgen binding protein (ABP), FSH receptor (FSHR), SERT-1 and smooth muscle iso-actin, or were synthesized from commercial sources.

The primers used for this analysis included:

```
Rat transferrin:
5': ATC TGG GAG ATC CTC AAA GTG GCT C
3': GGC ACT AGT CCA CAC TGG CCT GCT A FSH receptor:
5': CTG CCA AGA CAG CAA GGT GA
3': AGC CAT GGT TTG GTA AGG AA ABP androgen binding protein:
5': GAC GGA CCC TGA GAC ACA TT
3': GAA CAG TCC AGG TTG CAG GT Sert-1:
5': TCC TGC TCT GAC ACT TCC AGT T
3': AGC TGA CCC ATA ATT GAT GCA C Inhibin alpha:
5': TCT GAA CCA GAG GAG GAG GA
3': GGC CTC AGC AAG AAC AGA GT
```

The possible contamination of RNA with DNA was distinguished by performing the RT reaction without MMLV reverse transcriptase. The absence of any product in the amplification reaction using such a reverse transcribed preparation indicated the absence of any contaminating DNA in the RNA samples. Each RT reaction was performed using three different samples. The PCR-based amplification reactions were carried out in duplicate on each reverse-transcribed RNA sample. Simultaneous PCR reactions were also carried out using primers to rat cyclophilin designed to monitor the efficiency of the RT-PCR reactions. Cyclophilin was faithfully amplified in all the PCR reactions, indicating consistency in the quality of RT and PCR reactions. The identity of the corresponding PCR products and the sequence was confirmed by the Center for Reproductive Biology Molecular Biology Laboratory. The data presented is representative of three different RT-PCR reactions and DNA preparations.

Microarray Analysis

The gene expression profile of primary Sertoli cells and Sertoli cells over expressing Id1 or Id2 was determined using Affymetrix rat gene chips (RG-U34A; Affymetrix Inc., Santa Clara, Calif.). The RNA was purified and subjected to hybridization and analysis using the Affymetrix system. The gene profiling and data analysis was performed using GeneSpring software.

Results

Effect of Id1 and Id2 Over-Expression on Sertoli Cell Proliferation.

As shown in FIG. 1, over-expression of Id1 and Id2 initiated proliferation of the Sertoli cells, which did not occur in the primary non-transformed cells.

In order to analyze data from experiments performed on different days, the proliferation data similar to that shown in FIG. 1A, was normalized to the rate of proliferation of primary control Sertoli cells. This normalization allowed a uniform comparison and statistical analysis within different experiments. The proliferation rate of primary control Sertoli cells was negligible and was essentially the same as background. In a typical experiment, this background was approximately 400 cpm/ug DNA, which was due to non-specific binding and/or metabolism of $^3$H thymidine. As shown in FIG. 1A, the rate of proliferation of Sertoli cells over-expressing either Id1 or Id2 was significantly higher as compared to the primary Sertoli cells. (SC-Id1: Sertoli cells over-expressing Id1, SC-Id2: Sertoli cells over-expressing Id2; Above: proliferation rate of cells above 50 doublings; Below: proliferation rate of cell below 50 doublings, EGF: epidermal growth factor, 10% serum.)

Challenging the primary Sertoli cells in culture with 10% serum or EGF (FIGS. 1A and B) did not increase the proliferation rate. In contrast, the proliferation rate of the control un-stimulated Id1 or Id2 over-expressing Sertoli cells measured after 50 doublings, was 7 and 20 fold higher, respectively, as compared to primary Sertoli cells (FIGS. 1A and B).

The proliferation rate was also checked on the transformants before and after 50 doublings, in order to investigate if the rate of proliferation changed over time. The comparative data from these experiments also shows a striking difference between the Id and Id2 transformants. The data, shown in FIG. 1B, is normalized to counts per minute/mg DNA in primary control Sertoli cells set to 1. The cpm/mg DNA in primary control Sertoli cells was at or within 10% SEM of the background counts, suggesting that these cells failed to proliferate. This normalization allowed comparison of proliferation experiments performed over a period of time. Below 50 cell doublings, the Id1 transformants had a 3-fold lower rate of proliferation, as compared to Id2 transformants. Both the transformants also failed to respond to mitogenic stimulation. A significant increase in the proliferation rate of Id1 transformants was observed when measured after 50 cell doublings. Interestingly, before and after 50 cell doublings the rate of proliferation between controls was similar, but a significant increase (3-fold) in proliferation was observed after stimulation of Id1 transformants with mitogens. A similar increase in proliferation in response to serum as a mitogen, but not EGF was observed with the Id2 transformants, (FIG. 1B).

The doubling times over a period of time, were also determined, to confirm if the transformants continue to grow indefinitely or undergo senescence. The rate of doubling was recorded soon after transformation of the Sertoli cells with Id1 or Id2 plasmids.

FIGS. 2A and B, show doubling number over a period of time, plotted against time required for each doubling. The number of days required for each doubling was recorded, in order to determine the average doubling time for Sertoli cells over-expressing either Id1 (FIG. 2A) or Id2 (FIG. 2B). FIGS. 2C and D show each progressive doubling number plotted against number of days in culture, in order to determine if cells were undergoing senescence. A linear and continuous increase in doubling over a period of time, suggests that Sertoli cells over-expressing Id1 (FIG. 2C) or Id2 (FIG. 2D), did not undergo senescence over the period of time indicated on the X-axis. The data is an integration of cells counted before and after each doubling, in triplicates, over a period of more than 700 days.

Figure 2:
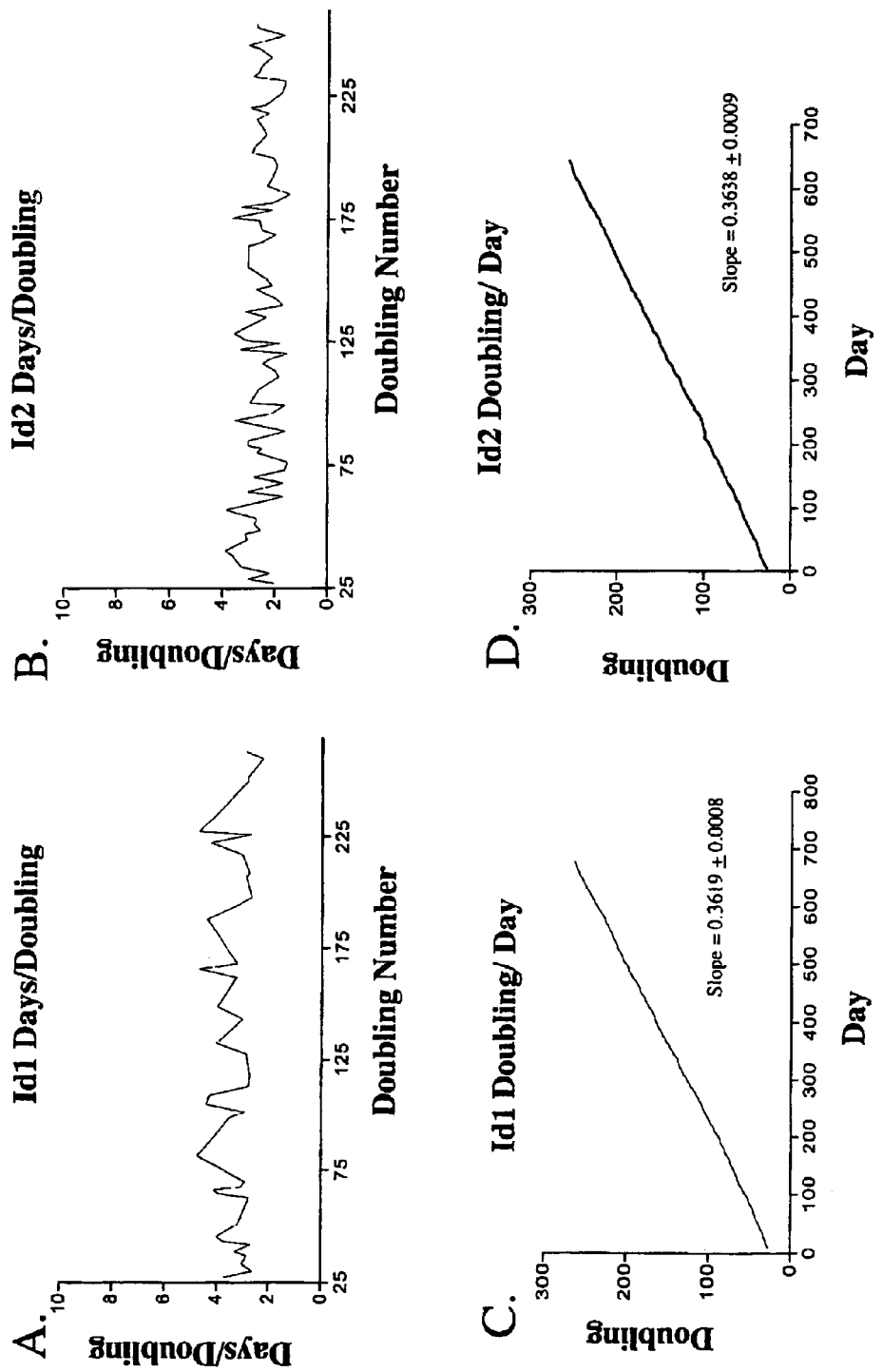
FIG. 2: Graphs showing doubling time of Sertoli cells over-expressing Id1 or Id2 as described in Example 2, infra.

As shown in FIG. 2A, the transformed Sertoli cells continued to proliferate indefinitely (at least 700 days post transfection). The doubling time as shown in FIG. 2A, was about 3-5 days doubling. A plateau was not observed when the doubling number was plotted against days post transfection, suggesting that the Sertoli cells did not undergo senescence at any time after transfection (FIG. 2B). Usually, the cells that can continue to proliferate past 70 doublings are considered transformed (Alani et al. 1999). As shown in FIG. 2, the Sertoli cells stably transfected with a Id1 or Id2 plasmid, have continued to proliferate past 250 doublings. These results suggest that over-expression of Id1 and Id2 appears to transform the Sertoli cells, and promote them to re-enter the cell cycle.

Confirmation of Over-Expression of Id1 and Id2:

Western blot analyses using specific antibodies to Id1 and Id2, were used to confirm the over-expression of Id1 and Id2, in the Sertoli cell lines. Since Id1 and Id2 are also expressed by primary Sertoli cells (Chaudhary et al. 2001), the Western blot experiments were designed using optimum protein concentrations at which endogenous Id levels become undetectable in the primary, non-transformed Sertoli cell cultures.

Figure 3:
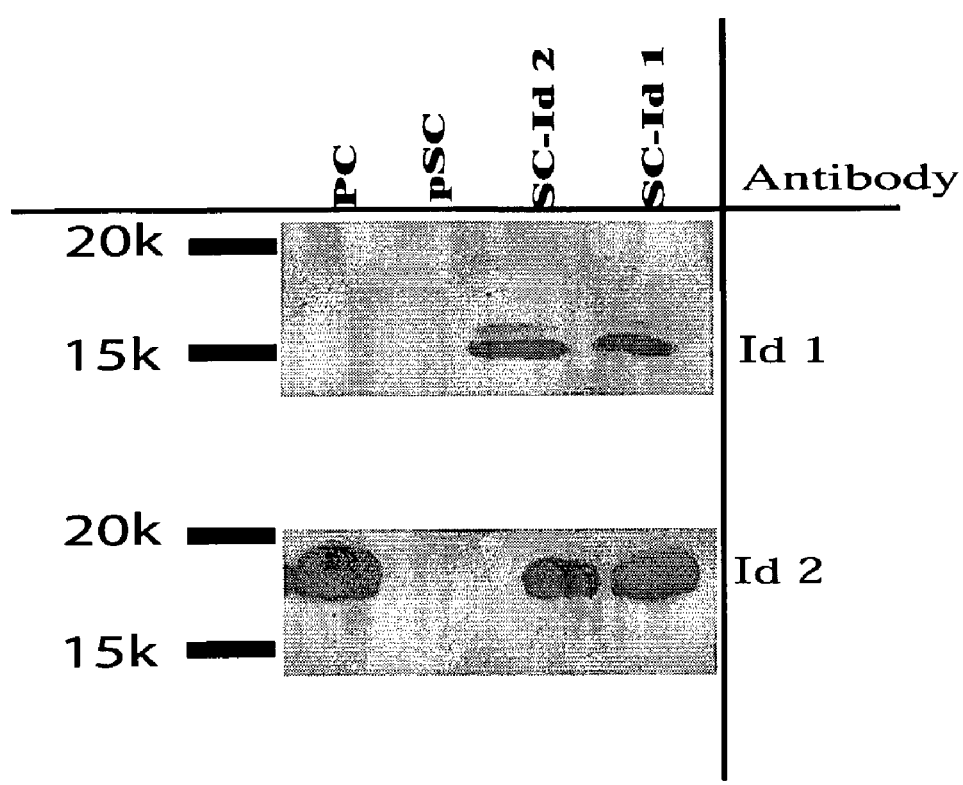
FIG. 3: Shows a Western blot analysis of Id1 and Id2 using the corresponding antibodies on cell lysates obtained from the primary Sertoli cells (pSC), or Sertoli cells over-expressing either Id1 (SCId1), or Id2 (SCId2), as described in Example 2, infra.

FIG. 3 shows the results of the Western blot analyses using the corresponding antibodies on cell lysates obtained from the primary Sertoli cells (pSC), or Sertoli cells over-expressing either Id1 (SCId1), or Id2 (SCId2). Also shown is the western blot of peritubular cells (PC). The approximate size of the specific immuno-protein complex is shown on the right. A representative of 3 different experiments is shown.

Sertoli cells, after several days in culture, have no Id expression. Lysates from these cells were compared to the Sertoli-Id lines. The Western analyses demonstrates that the Id1 and Id2 proteins were not detected in primary Sertoli cells, as shown in FIG. 3. Id1 and Id2 proteins were both detected in Sertoli cells transformed with either Id1 or Id2, respectively. Interestingly, increased levels of Id2 and Id1 levels were also observed in cells transformed with the opposing Id1 or Id2 proteins. These experiments confirm that Sertoli cells transformed with Id1 and Id2 expression plasmids induce the cognate proteins at a level significantly higher than the non-transformed cells (FIG. 3). Therefore, the transfection over-expression of either Id1 or Id2, induced the over-expression of both Id1 and Id2, in both Sertoli cell Id lines.

Characterization of Sertoli Cell Line Morphology

Figure 4:
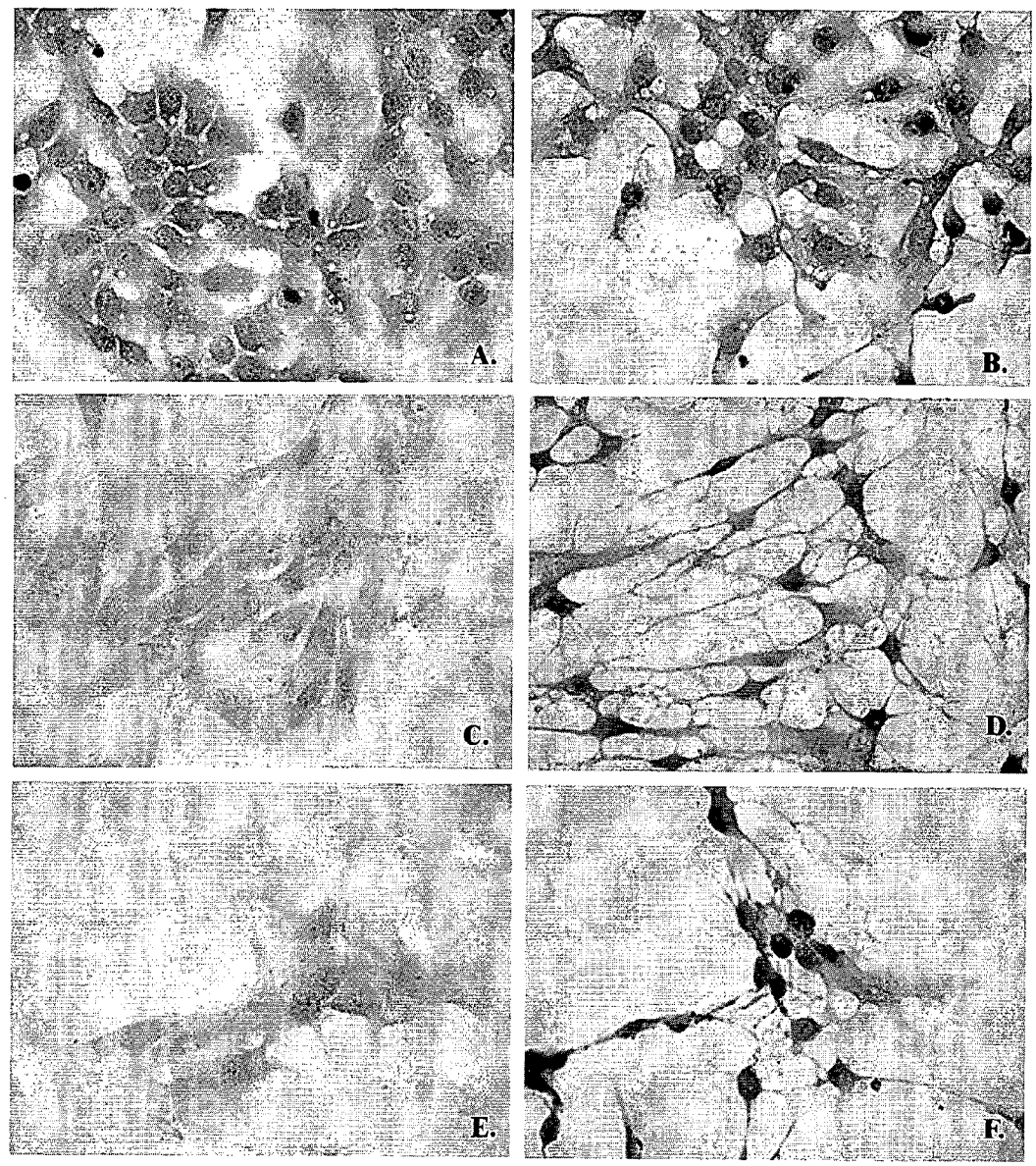
FIG. 4: Representative photographic images showing the morphology of Sertoli cells as observed under the light microscope, as described in Example 2, infra.

The Sertoli cell lines were designated SC-Id1 and SC-Id2, respectively. The primary Sertoli cells stained with H&E showed a typical morphology (FIG. 4). The large Sertoli cell nucleus showed the presence of dense nucleoli (FIG. 4). The irregular shape of the primary SC cells was changed to a smooth elongated and flattened morphology following over-expression with Id1 or Id2 (FIG. 4). The presence of dense nucleoli in cells over-expressing Id1 or Id2 was consistent with the primary Sertoli cell (FIG. 4). A striking similarity in the morphology was observed after treatment of primary Sertoli cells and SC-Id line cells with cAMP. This included an increase in the nuclear density and appearance of long cytoplasmic extensions. In the Id1 or Id2 over-expressing cells, cAMP treatments also increased nuclear density, with the appearance of long cytoplasmic extensions (FIG. 4). These observations suggest that the cAMP response, at least in terms of morphological changes, is retained by the Sertoli cells over expressing Id1 or Id2.

Characterization of Sertoli Cell Differentiated Genes

Reverse Transcriptase-Polymerase Chain Reaction of the genes normally expressed by primary Sertoli cells was used to confirm that the corresponding Id over-expressing cells were derived from the primary post-mitotic Sertoli cells.

Figure 5:
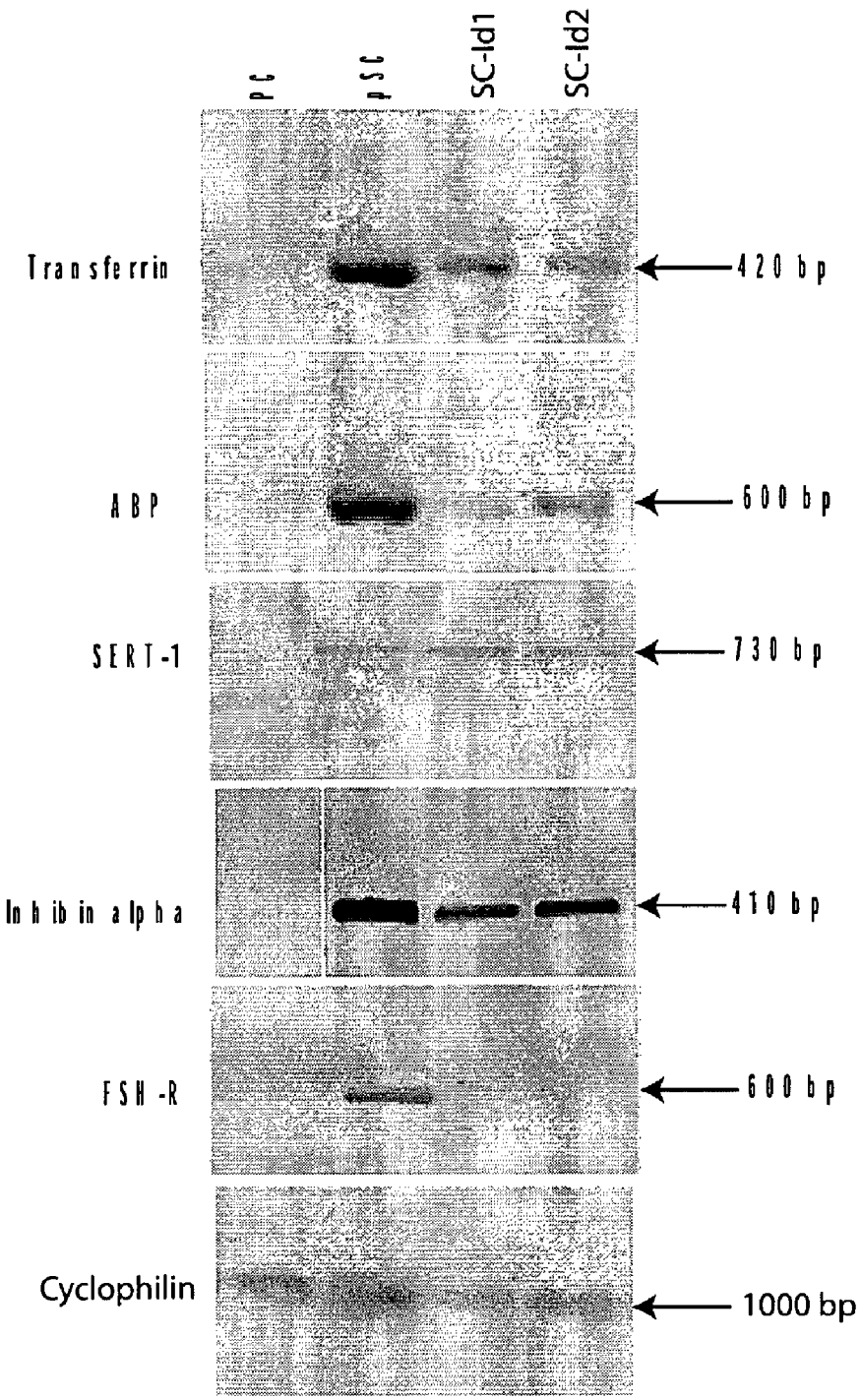
FIG. 5: Shows the results of reverse transcriptase polymerase chain reaction (RT-PCR) of genes normally expressed by primary Sertoli cells, as described in Example 2, infra. The size of each RT-PCR product is shown on the right. The RT-PCR is a representative of at least six experiments.

FIG. 5 shows the results of reverse transcriptase polymerase chain reaction (RT-PCR) of genes normally expressed by primary Sertoli cells. RT-PCR was performed on total RNA using gene specific primers listed in Table 1. The primary peritubular cells (PC) were used as a negative control, primary Sertoli cells (pSC) were used as a positive control, and Sertoli cell ID1 (SC-Id1) and ID2 (SC-Id2) lines were assayed at 50-120 doublings. The genes analyzed were transferrin, androgen binding protein (ABP), SERT-1, inhibin-alpha and FSH receptor (FSH-R). Cyclophilin (RT-PCR) was used to monitor the reverse transcription loading. The size (base pair) of each RT-PCR product is shown in the right of FIG. 5. The RT-PCR is representative of at least six experiments.

The SERT-1 gene is expressed primarily by Sertoli cells, (FIG. 5, lane 2, pSC), and was expressed by SC-Id lines over-expressing either Id1 or Id2 (FIG. 5, lane 3, SCId1 or lane 4, SCId2). Consistent with the observation that SERT-1 is Sertoli cell-specific, the testis peritubular cells did not express SERT-1 (FIG. 5, lane 1, PC). These results suggest that the SC-Id lines over-expressing Id, retain SERT-1 expression, and confirm the identity of Id over-expressing cells, as derived from primary Sertoli cells. The Sertoli cells over-expressing either Id1 or Id2, also expressed androgen binding protein, transferrin and inhibin alpha, as shown in FIG. 5.

These results demonstrate specific gene products of Sertoli cells, and show that the SC-Id lines retain some Sertoli cell differentiation functions. The expression of the FSH receptor was observed in the primary Sertoli cells but was lost following over-expression of Id1 or Id2, as shown in FIG. 5. Collectively, these results suggest that the cells over-expressing either Id1 or Id2, are derived from Sertoli cells and retain the ability to express many of the genes normally expressed by primary Sertoli cells, with the exception of the FSH receptor (Fshr).

Quantitative Microarray Analysis of Genes Expressed by Sertoli Cells

Microarray analysis was performed in order to quantitate the changes in the Sertoli cell transcriptome after ID over-expression (Tables 1 and 2). Comparisons were made with primary (non-transformed Sertoli cells) and SC-Id1 or SC-Id2 lines taken at approximately 80 doublings. The SC-Id1 line had 526 genes increase and 788 genes decreased greater than 2 fold in comparison to the primary Sertoli cells. The SC-Id2 line had 568 genes increase and 764 genes decrease.

As shown in Table 1, a decrease in transferrin, MIS, inhibin alpha subunit, and WT1 transcription factor was observed in the SC-Id lines, in comparison to primary Sertoli cells. Mullerian inhibiting substances (MIS) gene expression did not change significantly (Tables 1 and 2).

Over expression of Id1 or Id2 was accompanied by increased expression of Sry-related HMG box protein Sox11 and Cathepsin L. Cluster analysis demonstrated a number of cell cycle genes increased in the SC-Id lines, including the cyclins D and G, and cdk4 and cdc37, Table 1. The cell cycle inhibitor p21 decreased and p27 slightly decreased, while, p16 showed a small increase, (Tables 1 and 2). The retinoblastoma (Rb) gene and Rb binding protein (Rbbp9) gene were decreased, suggesting the cell cycle may have abnormal feedback mechanisms. Unfortunately, telomerase was not present on the microarray chip, so a preliminary experiment involved RT-PCR. Observations demonstrated the presence of telomerase reverse transcriptase (Tert) gene expression in the SC-Id lines, but at reduced levels compared to primary Sertoli cells.

Other gene clusters demonstrated general decreases in transcription factors and both increases and decreases in signal transduction and metabolic enzyme gene expression (Table 1). The semiquantitative data presented for PCR in FIG. 5, confirm the trends in data obtained from the microarray (Table 2) for selected genes. A statistical analysis of the microarray data was performed and all data presented in Tables 1 and 2, for specific genes is statistically different between the primary Sertoli cell and Sertoli cell Id-lines ($P<0.05$).

A detailed cluster analysis indicating the relationships (i.e. gene tree dendograms) of altered gene expression after ID transformation of the Sertoli cell is shown in FIG. 6. The changes in shading represent no change (lightest shading), increases (medium shading) and decreases (darkest shading) in related gene clusters with the gene tree dendrogram. This is a comparison between primary Sertoli, SC-Id1 and SC-Id2, and does not relate to primary Sertoli as with Tables 1 and 2. Although most changes in gene expression were similar in the SC-Id1 ad SC-Id2 lines (lightest shading), some differences were observed. Most of the gene expression in primary Sertoli cells was either increased (medium shading) or decreased (darkest shading) in relation to the SC-Id lines. Several of the specific gene clusters (i.e. cell cycle, signal transduction and transcription factor genes) involved, are also indicated in FIG. 6.

TABLE 1

SERTOLI ID-LINES-MICROARRAY GENE EXPRESSION ANALYSIS
Rat 13,000 Gene Chip (Affimetrix)

|  | SC-Id1 line | SC-Id2 line |
|---|---|---|
| (Total) Genes Increased (>2x) | 526 | 568 |
| (Total) Genes Decreased (>2x) | 788 | 764 |

TABLE 1-continued

SERTOLI ID-LINES-MICROARRAY GENE EXPRESSION ANALYSIS
Rat 13,000 Gene Chip (Affimetrix)

|  | SC-Id1 line | SC-Id2 line |
|---|---|---|
| | Sertoli Cell Differentiation Genes | |
| | Fold Increase (+) or Decrease (−) | |
| Transferrin | −168.5 | −90.7 |
| ABP | −1.9 | −1.7 |
| FSHR | −9.6 | −13.8 |
| Ceruloplasmin | −13.5 | −28.7 |
| Inhibin-Alpha | −5.5 | −6.4 |
| MIS | −1.0 | −1.1 |
| WT1 | −163.0 | −38.3 |
| SOX11 | +3.6 | +3.4 |
| CP2/Cathepsin L | +2.6 | +1.3 |
| | Cell Cycle Genes | |
| | Fold Increase (+) or Decrease (−) | |
| Cyclin D1 | +3.3 | +1.7 |
| Cyclin D2 | +3.2 | +3.4 |
| Cyclin D3 | +6.5 | +4.2 |
| Cyclin G | +3.8 | +3.6 |
| cdk4 | +2.4 | +2.6 |
| Cdc37 | +1.9 | +2.0 |
| p21 | −2.5 | −1.9 |
| p16 (CDKN2A, INK4a) | +1.3 | +1.4 |
| p27 (CDKN1B) | −1.2 | −1.3 |
| Rb binding protein | −5.0 | −3.6 |
| Rb | −2.7 | −2.5 |
| E2F | −2.0 | −2.0 |
| | Transcription Factor Genes | |
| (Total) Genes Increased (>2X) | 15 | 14 |
| (Total) Genes Decreased (>2X) | 44 | 43 |
| | Signal Transduction Genes | |
| (Total) Genes Increased (>2X) | 42 | 37 |
| (Total) Genes Decreased (>2X) | 57 | 52 |
| | Metabolic Genes | |
| (Total) Genes Increased (>2X) | 10 | 8 |
| (Total) Genes Decreased (>2X) | 29 | 36 |

TABLE 2

| Acc. No. | Common Name | Signal SC primary | SEM+/− | Id1 | SEM+/− | Id2 | SEM+/− |
|---|---|---|---|---|---|---|---|
| | Sertoli Cell Specific Genes | | | | | | |
| D38380 | transferrin | 3370.8 | 375.2 | 20.2 | 1.7 | 37.2 | 11.5 |
| M58040 | transferrin receptor | 75.1 | 18.3 | 20.9 | 6.7 | 37.0 | 7.2 |
| S98336 | Mullerian inhibiting substance | 167.0 | 20.5 | 166.5 | 8.8 | 150.8 | 9.1 |
| M36453 | inhibin alpha-subunit | 446.0 | 34.5 | 81.4 | 3.2 | 69.7 | 4.0 |
| AF044058 | androgen receptor interacting protein | 271.9 | 8.9 | 143.1 | 6.8 | 164.4 | 5.8 |
| S63358 | WT1 zinc-finger homolog [rats, testis] | 374.9 | 36.4 | 2.3 | 0.9 | 9.8 | 0.7 |
| M34043 | thymosin beta-10 (testis-specific) gene | 3156.1 | 198.4 | 3739.8 | 80.0 | 2418.2 | 55.6 |
| X15705 | testis-specific heat shock protein-related gene hst70 | 90.4 | 42.9 | 4.1 | 0.6 | 4.0 | 0.1 |
| AB009662 | testis specific protein | 61.9 | 43.7 | 2.6 | 0.6 | 1.3 | 0.8 |
| L33869 | ceruloplasmin mRNA | 347.8 | 151.1 | 25.8 | 1.4 | 12.1 | 1.7 |
| AJ004858 | Sry-related HMG-box protein Sox11 | 21.3 | 3.1 | 75.6 | 16.2 | 71.6 | 3.9 |

TABLE 2-continued

| Acc. No. | Common Name | Signal SC primary | SEM+/− | Id1 | SEM+/− | Id2 | SEM+/− |
|---|---|---|---|---|---|---|---|
| J01435 | cytochrome oxidase subunit I [Sertoli cells] | 7889.4 | 326.1 | 8014.5 | 702.4 | 7252.9 | 111.5 |
| M38759 | androgen binding protein | 467.0 | 121.3 | 9.1 | 5.2 | 7.6 | 1.1 |
| S85184 | Cyclic Protein-2 = cathepsin L proenzyme [Sertoli cells] | 260.1 | 10.4 | 665.1 | 30.9 | 340.2 | 46.7 |
| M37482 | inhibin beta-subunit | 68.2 | 9.5 | 84.4 | 14.5 | 76.2 | 4.3 |
| AF077195 | Sertoli cell protein (SC4) | 35.4 | 4.6 | 11.2 | 5.0 | 7.9 | 1.5 |
| M23264 | androgen receptor | 28.7 | 4.0 | 24.3 | 4.5 | 13.7 | 0.4 |
| L02842 | FSHR | 24.9 | 16.9 | 2.6 | 1.1 | 1.8 | 0.9 |
| Cell Cycle Genes | | | | | | | |
| D14014 | Cyclin D1 | 70.3 | 9.9 | 232.9 | 25.1 | 117.0 | 6.1 |
| D16308 | Cyclin D2 | 154.5 | 78.1 | 493.2 | 42.9 | 524.5 | 7.2 |
| D16309 | Cyclin D3 | 55.6 | 36.5 | 359.1 | 18.2 | 232.1 | 18.3 |
| D38560 | Cyclin G | 219.3 | 34.8 | 833.3 | 33.8 | 796.7 | 25.0 |
| L11007 | cdk4 | 315.2 | 4.7 | 861.0 | 101.7 | 763.2 | 78.2 |
| D26564_at | cdc34 | 200.6 | 7.8 | 380.7 | 9.3 | 403.0 | 59.0 |
| L41275 | p21 | 49.8 | 3.8 | 19.6 | 11.5 | 26.6 | 4.8 |
| S79760_at | p16 | 49.2 | 2.3 | 59.1 | 15.6 | 68.8 | 0.3 |
| D83792_at | p27 | 13.4 | 1.0 | 11.3 | 4.1 | 17.1 | 1.5 |
| D25233cds_at | Rb | 63.8 | 3.8 | 23.5 | 1.0 | 25.3 | 0.3 |
| AF025819 | Rb binding protein | 4.0 | 1.3 | 0.8 | 0.1 | 1.1 | 0.2 |
| U31668_at | E2F | 41.8 | 0.1 | 20.4 | 2.8 | 20.8 | 3.5 |

Discussion

The current Examples were designed in part, to investigate whether an altered expression of the members of the Id family, specifically Id1 and Id2, can allow re-entry of post-mitotic Sertoli cells into the cell cycle. Specifically, it was determined whether terminally differentiated post-mitotic Sertoli cells are competent to re-enter the cell cycle, if their levels are constitutively maintained in Sertoli cells. In order to make this determination, Id1 and Id2 were individually over-expressed in post mitotic rat Sertoli cells. Over-expression of Id1 or Id2 allowed post mitotic Sertoli cells to re-enter the cell cycle and undergo mitosis. The Sertoli cells continued to proliferate, even after 300 cell doublings. The functional markers of Sertoli cell differentiation such as transferrin, inhibin alpha, SERT-1 and ABP, continued to be expressed, albeit at lower levels. FSH receptor expression was lost in proliferating Sertoli cells.

The morphology of proliferating Sertoli cells resembled that of a cell undergoing proliferation, having a flattened phenotype. At no stage of proliferation did the cells exhibit senescence. The expression profile of proliferating Sertoli cells suggested an overall increase in cell cycle genes.

These results demonstrate that over-expression of Id1 and Id2 genes that are normally expressed by a terminally differentiated cell type, can initiate the cell cycle. Therefore model systems for other terminally differentiated cell types, such as neurons or myocytes, can be developed.

Previous studies to stimulate the terminally differentiated post-mitotic Sertoli cells to undergo cell proliferation have been unsuccessful. The rat and mouse Sertoli cell lines previously developed, such as MSC-1, RTS3-3, TM-4, ASC-17D, TTE3 (Bourdon et al. 1998; Capel et al. 1996; Dutertre et al. 1997; Hofmann et al. 1992; Mather 1980; Peschon et al. 1992; Rassoulzadegan et al. 1993; Roberts et al. 1995; Tabuchi et al. 2003; Walther et al. 1996), have been derived from tumorigenic models, or by over-expressing viral oncogenes, such as SV40 large T antigens, in proliferating pre-pubertal Sertoli cells. Therefore, the molecular events associated with Sertoli cell terminal differentiation have a dominant phenotype and are not permissive to proliferation. Over-expression of genes involved in proliferation and/or differentiation that are normally expressed by Sertoli cells, in response to hormones and growth factors, can provide more direct information on the associated molecular events involved in Sertoli cell terminal differentiation.

bHLH proteins have been shown to be involved in regulating differentiated functions, such as transferrin (Chaudhary et al. 1997; Chaudhary and Skinner 1999b), and ABP promoter activation, in post-mitotic Sertoli cells. The post pubertal Sertoli cells were also shown to express the dominant negative HLH proteins, Id1 and Id2 (Chaudhary et al. 2001; Sablitzky et al. 1998). In cultured primary Sertoli cells the levels of Id1 and Id2 expression decreased in response to FSH (Chaudhary et al. 2001). FSH is generally considered a differentiation promoting agent for Sertoli cells. This corresponds to Id proteins generally being considered as proliferation promoting and differentiation inhibiting factors. The ability of FSH to suppress Id expression, correlates with an increased differentiation and decreased proliferation of the cells. However, the expression of Id proteins by Sertoli cells suggests they may not only act as a switch between differentiation and proliferation.

These observations led to the proposal that stable over-expression of either Id1 and/or Id2, may allow post-mitotic Sertoli cells to re-enter the cell cycle and promote cell proliferation. This was supported by recent observations that Id over-expression can transform many different cell types such as keratinocytes (Alani et al. 1999). Unlike Sertoli cells, most of these cell types are quiescent, and after appropriate mitogenic stimuli can enter the cell cycle. The cellular transformation by Id proteins is mediated by stimulation of the cell cycle and activation of telomerase (Israel et al. 1999; Norton 2000; Yokota and Mori 2002). Consistent with these observations, an increased expression of Id proteins is also observed in many forms of cancer (Kebebew et al. 2000; Langlands et al. 2000; Lin et al. 2000; Maruyama et al. 1999; Takai et al. 2001; Wilson et al. 2001). The current Examples considered the effects of Id proteins on a terminally differentiated cell that is post-mitotic. Based on prior work, it was thought that these cells would not be able to re-enter the cell cycle, due to molecular events promoting the terminal differentiation.

As shown in these examples, over-expression of either Id1 or Id2 promoted Sertoli cell proliferation, which is not possible in the pubertal or adult Sertoli cells. ID1 over-expression promoted the proliferation of both pubertal (i.e. 20-day-old) and adult (i.e. 60-day-old) Sertoli cells. The observed increase in DNA synthesis was higher in cells expressing Id2, as compared to Id1. In addition, the proliferation rate may be dependent on mitogenic stimulation in cell over-expressing Id1 but is relatively independent in cells expressing Id2. The exact mechanism by which Id proteins initiate Sertoli cell proliferation is not known. However, Id over-expression is expected to involve alterations in cell cycle control genes such as p27, p21, c-Myc, p16 and Rb activity. This is based on the mechanism by which Id promotes proliferation in other cell systems, such as endothelial cells, keratinocytes and mammary epithelial cells (FIG. 7). FIG. 7 shows FSH acting at the FSH receptor activates cAMP and protein kinase A (PKA), that activates Sertoli cell differentiated genes and inhibits ID expression. ID binds retinoblastoma protein (Rb) that allows E2F to promote the cell cycle. ID blocks bHLH proteins needed for growth inhibitors p16, p21 and p27 expression, and so decreases growth inhibition.

In general, Id may regulate the expression/function of Myc (Lasorella et al. 2002), retinoblastoma proteins (Rb) (Iavarone et al. 1994) and related protein p107 and p130 (Lasorella et al. 1996) and cyclin dependent kinase (CDKN2) (Zebedee and Hara 2001).

Reversing the cell cycle arrest through ID binding to the Rb family of proteins releases E2F to then promote cell cycle gene (e.g. S-phase factors) expression (Iavarone et al., 1994). In addition to reversing the cell cycle arrest through its binding to the Rb family of proteins, Id2 may also antagonize the growth-suppressive activities of cyclin-dependent kinase inhibitors p16 (Alani et al. 2001; Ohtani et al. 2001) and p21 (FIG. 7) (Prabhu et al. 1997). C-myc activity in response to FSH has been reported in pre-pubertal and early pubertal Sertoli cells to be involved in cell proliferation (Lim et al. 1994). The cMyc-Id-pRb pathway has been shown to be active in many proliferative cells (Lasorella et al. 2000). Without being bound to any specific theory, based on these observations, Id over-expression may activate this pathway, allowing the cells to re-enter the cell cycle (FIG. 7).

The increase in both Id1 and Id2 levels following transformation with either Id1 or Id2 suggests that both the isoforms may be required to promote the Sertoli cell proliferation. This would explain why the cell phenotype is similar between the SC-Id1 and SC-Id2 lines. Observations suggest an interaction between the Id family members. The actions of either ID1 or ID2 may alter transcriptional activity such that the promoters for both ID genes are activated.

Interestingly, the Sertoli cells transformed with Id1 or Id2, failed to enter senescence, even after 200 cell doublings. Previous studies have proposed that Id over-expression may delay replicative senescence in human endothelial cells (Tang et al., 2002), keratinocytes (Alani et al., 2001) and fibroblasts (Zheng et al. 2004). A similar study using retroviral based over-expression of ID1 in human keratinocytes delayed the onset of replicative senescence (Nickoloff et al., 2000). Unlike the study of Alani et al., (2001), who selected the ID-1 transformants that had elevated telomerase activity and inactivated Rb/p16 pathway, Nickoloff et al., (2000) used unselected ID-1 transformants. This experimental discrepancy may have led to different conclusions in the ability of ID-1 to immortalize (Alani et al. 2000) or delay (Nickoloff et al. 2000) replicative senescence of human keratinocytes. These results suggested that immortalization may require the activation of telomerase TERT. The Examples herein provided Sertoli cells unselected for activation of telomerase and inactivation of the p16/Rb pathway. The ability of Sertoli cells that overexpress ID to survive and proliferate was the only selection performed. Preliminary studies support that telomerase (i.e. Tert) is present in the SC-Id lines, but at a reduced level compared to primary Sertoli cells. Previously high levels of telomerase reverse transcriptase (Tert) have been shown in other terminally differentiated cells such as neurons (Fu et al., 2002).

The role of Id genes in regulating senescence is also evident from the Id1 null mouse embryo fibroblasts that senesce prematurely because of increased expression of p16 (Alani et al. 2001). The molecular mechanisms involved in the bypass of senescence by Sertoli cells over expressing Id1 and Id2 may be unique. It is likely that ID proteins will influence telomerase activity and have a role in the blocked senescence. It may be that the terminally differentiated post-mitotic nature of the cell promotes or allows this immortalization. If the molecular control of terminal differentiation involves a permanent alteration in the cell cycle pathways, then Id over-expression could be used to study this process in more detail. Moreover, Id over-expression can be used to promote cell proliferation in post-mitotic cells such as neurons or muscle cells. In the event an inducible promoter could be used, then regeneration of these terminally differentiated cells could provide therapeutic strategies for neuro-degenerative or muscle degenerative diseases. These examples with Sertoli cells, provide insights into a link between Id proteins, and the post-mitotic state of these and other terminally differentiated cells.

The presence of Sertoli genes such as inhibin alpha, transferrin, SERT-1 and ABP suggests that Id1/Id2 over-expression was permissive to the expression of these differentiated genes, which are normally expressed by differentiated Sertoli cells. The levels of their expression were diminished as compared to the primary Sertoli cells, as demonstrated in the microarray and RT-PCR experiments. The magnitude of the change in gene expression is sometimes different between the two procedures. This is likely due in part to PCR using two oligonucleotide primers while the microarray procedure involves 16 different oligonucleotide primers for the specific gene. The observed decrease can be at least partially explained, based on the observations that transferrin gene expression is regulated by an E Box present in the proximal promoter region of transferrin (Chaudhary et al. 1997). Previous experiments have shown that transferrin promoter activity can be blocked by either mutating the E-box, or by transiently over-expressing Id (Chaudhary et al. 1997). The loss of transferrin expression in these SC-Id cell lines, further confirms the previous results, that bHLH proteins are involved in regulating the expression of the transferrin gene. Ectopically expressed Id1 or Id2 may titer out the positively acting bHLH protein, making them unavailable for binding and activating differentiated gene expression (FIG. 7). Similar mechanisms are responsible for the down-regulation of ABP (Saxlund et al., 2004). The complete loss of FSH receptor in Sertoli cells over expressing Id1/Id2 may also be due to lack of available bHLH transcription factors required for inducing FSH receptor expression (Heckert et al. 1998).

The analysis of the Sertoli cell transcriptome in primary Sertoli cells and the Sertoli-Id lines demonstrates the presence of a number of Sertoli cell differentiated genes, but at reduced levels of expression. Therefore, the cells had a lower level of differentiated function, but did not dramatically alter cellular differentiation. A number of differentiated markers increased in expression (i.e. Sox 11, cyclic protein 2) suggesting these genes may have a distinct role and regulation in contrast to those decreased. A number of cell cycle genes were increased as discussed. Other cellular pathways influenced by the over-expression of ID1 or ID2 were transcriptional regulation pathways, signal transduction pathways and metabolic pathways (Table 1 and FIG. 6).

The relationships between the gene clusters is shown in FIG. 6, depicting the results of smooth correlation cluster analysis of changes in the transcriptomes of primary Sertoli cells (SC Primary), Sertoli cell-Id1 (SC-Id1) and Sertoli cell-ID2 (SC-ID2) at 80 doublings. Comparison was made between each separately. The dendrogram with relative expression relationships on the right of the Figure correlates with increased gene clusters (medium shading) and decreased (dark shading), as indicated by the correlation panel. Data for all genes (>2x) minus the EST's, cell cycle genes, transcription factor genes and signal transduction genes are presented in FIG. 6. Analysis was carried out using a GeneSpring software procedure using the data summarized in Tables 1 and 2.

The results shown in FIG. 6 demonstrate the majority of changes were similar between SC-Id1 and SC-Id2. The genes that are distinct between ID1 and ID2 likely reflect differences in the actions of ID1 versus ID2. In general, cell cycle gene clusters were increased, while differentiated genes and transcription factor gene clusters were decreased in response to ID over-expression. This correlates with the decrease in cellular differentiation and increase in cell cycle induction summarized in FIG. 7. This analysis provides insights into how these cellular pathways respond between the terminally differentiated state and active cell cycle proliferative state.

A distinction needs to be made in the Sertoli cell lines generated by over-expression of Id1/Id2, versus those obtained by SV40 T antigen or other oncogenes. The SC-Id cell lines were developed using over-expression of a gene normally expressed by Sertoli cells in response to, and these genes are required to maintain Sertoli cell differentiated functions. Id genes are also a normal gene involved in regulating the cell cycle (Zebedee and Hara 2001). The functional morphology, physiology and gene expression profile of these Sertolic cell lines over expressing Id1/Id2 may more closely resemble the primary Sertoli cells, as compared to the cell lines developed by SV40 T antigen. This is evident from the strikingly similar morphology between primary Sertoli cells and Sertoli cells over-expressing Id1/Id2. However, certain similarities between all the cell-lines exist, such as loss of FSH receptor (McGuinness et al. 1994). The Examples herein used a constitutively expressed Id construct. Alternatively, an inducible promoter is used to turn ID expression "on" and "off", to permit analysis of the transition of Sertoli cells from a post-mitotic to mitotic state. Terminal differentiation of the cells in regards to gene expression could be more precisely controlled and monitored.

The efficiency of spermatogenesis is largely dependent on the number of Sertoli cells in the testis (Orth et al. 1988). These observations are supported by the FSH receptor and FSH beta subunit knockout models (Abel et al. 2000; Kumar et al. 1997). In these knockouts, a decrease in Sertoli cell numbers is directly reflected in terms of decreased spermatogenesis (Krishnamurthy et al. 2000). These observations support the notion that an increased Sertoli cell number may lead to quantitatively increased spermatogenesis. The effect of increased Sertoli cell proliferation on spermatogenesis can be studied in an inducible transgenic mouse model, e.g B57Black, in which Id1/2 gene expression is directed in Sertoli cells using Sertoli cell specific promoters, such as SERT-1, in stably integrated plasmids (Chaudhary et al., 2004). In the event Id over-expression increases Sertoli cell number, then a larger testis and greater sperm output is expected. This model requires turning "off" ID expression and allowing normal cellular differentiated gene expression to be present. Such results provide a basis for use of these methods to increase fertility and sperm output of a subject.

The results presented herein indicate the alteration of the post-mitotic nature of terminally differentiated cells. This has applications in many disease states, such as neuro-regeneration and muscle regeneration, as well as fertility enhancement. The proliferation and differentiation of a target cell, such as a neuron, are promoted in response to ID expression, allowing neural regeneration to occur.

REFERENCES

Abel M H, Wootton A N, Wilkins V, Huhtaniemi I, Knight P G, Charlton H M. 2000. The effect of a null mutation in the follicle-stimulating hormone receptor gene on mouse reproduction. Endocrinology 141(5):1795-1803.

Alani R M, Hasskarl J, Grace M, Hernandez M C, Israel M A, Munger K. 1999. Immortalization of primary human keratinocytes by the helix-loop-helix protein, Id-1. Proc Natl Acad Sci USA 96(17):9637-9641.

Alani R M, Young A Z, Shifflett C B. 2001. Id1 regulation of cellular senescence through transcriptional repression of p16/Ink4a. Proc Natl Acad Sci USA 98(14):7812-7816.

Anthony C T, Rosselli M, Skinner M K. 1991. Actions of the testicular paracrine factor (P-Mod-S) on Sertoli cell transferrin secretion throughout pubertal development. Endocrinology 129(1):353-360.

Anway M D, Folmer J, Wright W W, Zirkin B R. Isolation of Sertoli cells from adult rat testes: an approach to ex vivo studies of Sertoli cell function. Biol Reprod 2003; 68: 996-1002.

Bain G, Gruenwald S, Murre C. 1993. E2A and E2-2 are subunits of B-cell specific E2-box DNA-binding proteins. Mol Cell Biol 13(6):3522-3529.

Barone M V, Pepperkok R, Peverali F A, Philipson L. 1994. Id proteins control growth induction in mammalian cells. Proc Natl Acad Sci USA 91(11):4985-4988.

Benezra R, Davis R L, Lockshon D, Turner D L, Weintraub H. 1990. The protein Id: a negative regulator of helix-loop-helix DNA binding proteins. Cell 61 (1):49-59.

Bicknell K A, Surry E L, Brooks G. 2003. Targeting the cell cycle machinery for the treatment of cardiovascular disease. J Pharm Pharmacol 55(5):571-591.

Bourdon V, Lablack A, Abbe P, Segretain D; Pointis G. 1998. Characterization of a clonal Sertoli cell line using adult PyLT transgenic mice. Biol Reprod 58(2):591-599.

Braun K W, Vo M N, Kim K H. 2002. Positive regulation of retinoic acid receptor alpha by protein kinase C and mitogen-activated protein kinase in sertoli cells. Biol Reprod 67(1):29-37.

Bremner W J, Millar M R, Sharpe R M, Saunders P T. 1994. Immunohistochemical localization of androgen receptors in the rat testis: evidence for stage-dependent expression and regulation by androgens. Endocrinology 135(3):1227-1234.

Buzzard J J, Wreford N G, Morrison J R. 2003. Thyroid hormone, retinoic acid, and testosterone suppress proliferation and induce markers of differentiation in cultured rat sertoli cells. Endocrinology 144(9):3722-3731.

Capel B, Hawkins J R, Hirst E, Kioussis D, Lovell-Badge R. 1996. Establishment and characterization of conditionally immortalized cells from the mouse urogenital ridge. J Cell Sci 109 (Pt 5):899-909.

Chaudhary J, Cupp A S, Skinner M K. 1997. Role of basic-helix-loop-helix transcription factors in Sertoli cell differentiation: identification of an E-box response element in the transferrin promoter. Endocrinology 138(2):667-675.

Chaudhary J, Johnson J, Kim G, Skinner M K. 2001. Hormonal regulation and differential actions of the helix-loop-helix transcriptional inhibitors of differentiation (Id1, Id2, Id3, and Id4) in Sertoli cells. Endocrinology 142(5):1727-1736.

Chaudhary J, Kim G, Skinner M K. 1999. Expression of the basic helix-loop-helix protein REBalpha in rat testicular Sertoli cells. Biol Reprod 60(5):1244-1250.

Chaudhary J, Mosher R, Kim G, Skinner M K. 2000. Role of winged helix transcription factor (WIN) in the regulation of Sertoli cell differentiated functions: WIN acts as an early event gene for follicle-stimulating hormone. Endocrinology 141(8):2758-2766.

Chaudhary J, Sadler-Riggleman I, Skinner M K. Identification of a novel Sertoli cell gene product SERT that influences follicle stimulating hormone actions. Gene 2004; 324: 79-88.

Chaudhary J, Skinner M K. 1999a. The basic helix-loop-helix E2A gene product E47, not E12, is present in differentiating sertoli cells. Mol Reprod Dev 52:1-8.

Chaudhary J, Skinner M K. 1999b. Basic helix-loop-helix proteins can act at the E-box within the serum response element of the c-fos promoter to influence hormone-induced promoter activation in Sertoli cells. Mol Endocrinol 13(5):774-786.

Chaudhary J, Skinner M K. 1999c. E-box and cyclic adenosine monophosphate response elements are both required for follicle-stimulating hormone-induced transferrin promoter activation in Sertoli cells. Endocrinology 140(3): 1262-1271.

Christy B A, Sanders L K, Lau L F, Copeland N G, Jenkins N A, Nathans D. 1991. An Id-related helix-loop-helix protein encoded by a growth factor-inducible gene. Proc Natl Acad Sci USA 88(5):1815-1819.

Crepieux P, Marion S, Martinat N, Fafeur V, Vern Y L, Kerboeuf D, Guillou F, Reiter E. 2001. The ERK-dependent signalling is stage-specifically modulated by FSH, during primary Sertoli cell maturation. Oncogene 20(34):4696-4709.

Daggett M A, Rice D A, Heckert L L. 2000. Expression of steroidogenic factor 1 in the testis requires an E box and CCAAT box in its promoter proximal region. Biol Reprod 62(3):670-679.

Dorrington J H, Roller N F, Fritz I B. 1975. Effects of follicle-stimulating hormone on cultures of Sertoli cell preparations. Mol Cell Endocrinol 3(1):57-70.

Dutertre M, Rey R, Porteu A, Josso N, Picard J Y. 1997. A mouse Sertoli cell line expressing anti-Mullerian hormone and its type II receptor. Mol Cell Endocrinol 136(1):57-65.

Einarson M B, Chao M V. 1995. Regulation of Id1 and its association with basic helix-loop-helix proteins during nerve growth factor-induced differentiation of PC12 cells. Mol Cell Biol 15:4175-4183.

Fu W, Lu C, Mattson M P. Telomerase mediates the cell survival-promoting actions of brain-derived neurotrophic factor and secreted amyloid precursor protein in developing hippocampal neurons. J Neurosci 2002; 22: 10710-10719.

Goetz T L, Lloyd T L, Griswold M D. 1996. Role of E box and initiator region in the expression of the rat follicle-stimulating hormone receptor. J Biol Chem 271(52):33317-33324.

Gronning L M, Dahle M K, Tasken K A, Enerback S, Hedin L, Tasken K, Knutsen H K. 1999. Isoform-specific regulation of the CCAAT/enhancer-binding protein family of transcription factors by 3',5'-cyclic adenosine monophosphate in Sertoli cells. Endocrinology 140(2):835-843.

Hacker A, Capel B, Goodfellow P, Lovell-Badge R. 1995. Expression of Sry, the mouse sex determining gene. Development 121(6):1603-1614.

Hansson V V, Skalhegg B S, Tasken K. 2000. Cyclic-AMP-dependent protein kinase (PKA) in testicular cells. Cell specific expression, differential regulation and targeting of subunits of PKA. J Steroid Biochem Mol Biol 73(1-2):81-92.

Hara E, Yamaguchi T, Nojima H, Ide T, Campisi J, Okayama H, Oda K. 1994. Id related genes encoding helix-loop-helix proteins are required for G1 progression and are repressed in senescent human fibroblasts. J Biol Chem 269(3):2139-2145.

Hatano O, Takayama K, Imai T, Waterman M R, Takakusu A, Omura T, Morohashi K. 1994. Sex-dependent expression of a transcription factor, Ad4BP, regulating steroidogenic P-450 genes in the gonads during prenatal and postnatal rat development. Development 120(10):2787-2797.

Heckert L L, Daggett M A, Chen J. 1998. Multiple promoter elements contribute to activity of the follicle-stimulating hormone receptor (FSHR) gene in testicular Sertoli cells. Mol Endocrinol 12(10):1499-1512.

Hofmann M C, Narisawa S, Hess R A, Millan J L. 1992. Immortalization of germ cells and somatic testicular cells using the SV40 large T antigen. Exp Cell Res 201(2):417-435.

Holsberger D R, Jirawatnotai S, Kiyokawa H, Cooke P S. 2003. Thyroid hormone regulates the cell cycle inhibitor p27Kip1 in postnatal murine Sertoli cells. Endocrinology 144(9):3732-3738.

Hu J S, Olson E N, Kingston R E. 1992. HEB, a helix-loop-helix protein related to E2A and ITF2 that can modulate the DNA-binding ability of myogenic regulatory factors. Mol Cell Biol 12(3):1031-1042.

Iavarone A, Garg P, Lasorella A, Hsu J, Israel M A. 1994. The helix-loop-helix protein Id-2 enhances cell proliferation and binds to the retinoblastoma protein. Genes Dev 8(11): 1270-1284.

Israel M A, Hernandez M C, Florio M, Andres-Barquin P J, Mantani A, Carter J H, Julin C M. 1999. Id gene expression as a key mediator of tumor cell biology. Cancer Res 59(7 Suppl): 1726s-1730s.

Jegou B. 1992. The Sertoli cell in vivo and in vitro. Cell Biol Toxicol 8(3):49-54.

Jellinger K A. 2003. General aspects of neurodegeneration. J Neural Transm Suppl(65):101-144.

Jia M C, Ravindranath N, Papadopoulos V, Dym M. 1996. Regulation of c-fos mRNA expression in Sertoli cells by cyclic AMP, calcium, and protein kinase C mediated pathways. Mol Cell Biochem 156(1):43-49.

Kebebew E, Treseler P A, Duh Q Y, Clark O H. 2000. The helix-loop-helix transcription factor, Id-1, is overexpressed in medullary thyroid cancer. Surgery 128(6):952-957.

Ketola I, Anttonen M, Vaskivuo T, Tapanainen J S, Toppari J, Heikinheimo M. 2002. Developmental expression and spermatogenic stage specificity of transcription factors GATA-1 and GATA-4 and their cofactors FOG-1 and FOG-2 in the mouse testis. Eur J Endocrinol 147(3):397-406.

Krishnamurthy H, Danilovich N, Morales C R, Sairam M R. 2000. Qualitative and quantitative decline in spermatogenesis of the follicle-stimulating hormone receptor knockout (FORKO) mouse. Biol Reprod 62(5):1146-1159.

Kumar T R, Wang Y, Lu N, Matzuk M M. 1997. Follicle stimulating hormone is required for ovarian follicle maturation but not male fertility. Nat Genet 15(2):201-204.

Langlands K, Down G A, Kealey T. 2000. Id proteins are dynamically expressed in normal epidermis and dysregulated in squamous cell carcinoma. Cancer Res 60(21):5929-5933.

Langlands K, Yin X, Anand G, Prochownik E V. 1997. Differential interactions of Id proteins with basic-helix-loop-helix transcription factors. J Biol Chem 272(32):19785-19793.

Lasorella A, Boldrini R, Dominici C, Donfrancesco A, Yokota Y, Inserra A, Iavarone A. 2002. Id2 is critical for cellular proliferation and is the oncogenic effector of N-myc in human neuroblastoma. Cancer Res 62(1):301-306.

Lasorella A, Iavarone A, Israel M A. 1996. Id2 specifically alters regulation of the cell cycle by tumor suppressor proteins. Mol Cell Biol 16(6):2570-2578.

Lasorella A, Noseda M, Beyna M, Yokota Y, Iavarone A. 2000. Id2 is a retinoblastoma protein target and mediates signalling by Myc oncoproteins. Nature 407(6804):592-598.

Lassar A B, Davis R L, Wright W E, Kadesch T, Murre C, Voronova A, Baltimore D, Weintraub H. 1991. Functional activity of myogenic HLH proteins requires hetero oligomerization with E12/E47-like proteins in vivo. Cell 66(2):305-315.

Law G L, Griswold M D. 1994. Activity and form of sulfated glycoprotein 2 (clusterin) from cultured Sertoli cells, testis, and epididymis of the rat. Biol Reprod 50(3):669-679.

Lim K, Hwang B D. 1995. Follicle-stimulating hormone transiently induces expression of protooncogene c-myc in primary Sertoli cell cultures of early pubertal and prepubertal rat. Mol Cell Endocrinol 111(1):51-56.

Lim K, Yoo J H, Kim K Y, Kweon G R, Kwak S T, Hwang B D. 1994. Testosterone regulation of proto-oncogene c-myc expression in primary Sertoli cell cultures from prepubertal rats. J Androl 15(6):543-550.

Lin C Q, Singh J, Murata K, Itahana Y, Parrinello S, Liang S H, Gillett C E, Campisi J, Desprez P Y. 2000. A role for Id-1 in the aggressive phenotype and steroid hormone response of human breast cancer cells. Cancer Res 60(5):1332-1340.

Lovell-Badge R, Hacker A. 1995. The molecular genetics of Sry and its role in mammalian sex determination. Philos Trans R Soc Lond B Biol Sci 350(1333):205-214.

Loveys D A, Streiff M B, Kato G J. 1996. E2A basic-helix-loop-helix transcription factors are negatively regulated by serum growth factors and by the Id3 protein. Nucleic Acids Res 24(14):2813-2820.

Maruyama H, Kleeff J, Wildi S, Friess H, Buchler M W, Israel M A, Korc M. 1999. Id-1 and Id-2 are overexpressed in pancreatic cancer and in dysplastic lesions in chronic pancreatitis. Am J Pathol 155(3):815-822.

Massari M E, Murre C. 2000. Helix-loop-helix proteins: regulators of transcription in eucaryotic organisms. Mol Cell Biol 20(2):429-440.

Mather J P. 1980. Establishment and characterization of two distinct mouse testicular epithelial cell lines. Biol Reprod 23(1):243-252.

McGuinness M P, Linder C C, Morales C R, Heckert L L, Pikus J, Griswold M D. 1994. Relationship of a mouse Sertoli cell line (MSC-1) to normal Sertoli cells. Biol Reprod 51(1):116-124.

McLean D J, Friel P J, Pouchnik D, Griswold M D. Oligonucleotide microarray analysis of gene expression in follicle-stimulating hormone-treated rat Sertoli cells. Mol Endocrinol 2002; 16: 2780-2792.

Moens U, Setemes O M, Johansen B, Rekvig O P. Mechanisms of transcriptional regulation of cellular genes by SV40 large T- and small T-antigens. Virus Genes 1997; 15: 135-154.

Moldes M, Lasnier F, Feve B, Pairault J, Djian P. 1997. Id3 prevents differentiation of preadipose cells. Mol Cell Biol 17(4):1796-1804.

Murre C, Bain G, van Dijk M A, Engel I, Fumari B A, Massari M E, Matthews J R, Quong M W, Rivera R R, Stuiver M H. 1994. Structure and function of helix-loop helix proteins. Biochim Biophys Acta 1218(2):129-135.

Murre C, McCaw P S, Baltimore D. 1989a. A new DNA binding and dimerization motif in immunoglobulin enhancer binding, daughterless, MyoD, and myc proteins. Cell 56(5):777-783.

Murre C, McCaw P S, Vaessin H, Caudy M, Jan L Y, Jan Y N, Cabrera C V, Buskin J N, Hauschka S D, Lassar A B, et al. 1989b. Interactions between heterologous helix-loop-helix proteins generate complexes that bind specifically to a common DNA sequence. Cell 58(3):537-544.

Nickoloff B J, Chaturvedi V, Bacon P, Qin J Z, Denning M F, Diaz M O. Id-1 delays senescence but does not immortalize keratinocytes. J Biol Chem 2000; 275: 27501-27504.

Norton J D. 2000. ID helix-loop-helix proteins in cell growth, differentiation and tumorigenesis. J Cell Sci 113 (Pt 22):3897-3905.

Norton J N, Skinner M K. 1992. Regulation of Sertoli cell differentiation by the testicular paracrine factor PModS: potential role of immediate-early genes. Mol Endocrinol 6(12):2018-2026.

Ohtani N, Zebedee Z, Huot T J, Stinson J A, Sugimoto M, Ohashi Y, Sharrocks A D, Peters G, Hara E. 2001. Opposing effects of Ets and Id proteins on p16INK4a expression during cellular senescence. Nature 409(6823):1067-1070.

Orth J M, Gunsalus G L, Lamperti A A. 1988. Evidence from Sertoli cell-depleted rats indicates that spermatid number in adults depends on numbers of Sertoli cells produced during perinatal development. Endocrinology 122(3):787-794.

Palmero S, Prati M, Bolla F, Fugassa E. 1995. Tri-iodothyronine directly affects rat Sertoli cell proliferation and differentiation. J Endocrinol 145(2):355-362.

Peschon J J, Behringer R R, Cate R L, Harwood K A, Idzerda R L, Brinster R L, Palmiter R D. 1992. Directed expression of an oncogene to Sertoli cells in transgenic mice using mullerian inhibiting substance regulatory sequences. Mol Endocrinol 6(9):1403-1411.

Petersen C, Boitani C, Froysa B, Soder O. 2002. Interleukin-1 is a potent growth factor for immature rat sertoli cells. Mol Cell Endocrinol 186(1):37-47.

Prabhu S, Ignatova A, Park S T, Sun X H. 1997. Regulation of the expression of cyclin-dependent kinase inhibitor p21 by E2A and Id proteins. Mol Cell Biol 17(10):5888-5896.

Prasad K N, Cole W C, Yan X D, Nahreini P, Kumar B, Hanson A, Prasad J E. 2003. Defects in cAMP-pathway may initiate carcinogenesis in dividing nerve cells: A review. Apoptosis 8(6):579-586.

Quong M W, Massari M E, Zwart R, Murre C. 1993. A new transcriptional activation motif restricted to a class of helix-loop-helix proteins is functionally conserved in both yeast and mammalian cells. Mol Cell Biol 13(2):792-800.

Rassoulzadegan M, Paquis-Flucklinger V, Bertino B, Sage J, Jasin M, Miyagawa K, van Heyningen V, Besmer P, Cuzin F. 1993. Transmeiotic differentiation of male germ cells in culture. Cell 75(5):997-1006.

Roberts K P, Banerjee P P, Tindall J W, Zirkin B R. 1995. Immortalization and characterization of a Sertoli cell line from the adult rat. Biol Reprod 53(6):1446-1453.

Sablitzky F, Moore A, Bromley M, Deed R W, Newton J S, Norton J D. 1998. Stage- and subcellular-specific expression of Id proteins in male germ and Sertoli cells implicates distinctive regulatory roles for Id proteins during meiosis, spermatogenesis, and Sertoli cell function. Cell Growth Differ 9(12):1015-1024.

Saxlund M A, Sadler-Riggleman I, Skinner M K. Role of basic helix-loop-helix (bHLH) and CREB transcription factors in the regulation of Sertoli cell androgen binding protein expression. Molecular Reproduction and Development 2004; 68: 269-278.

Schlatt S, de Kretser D M, Loveland K L. 1996. Discriminative analysis of rat Sertoli and peritubular cells and their proliferation in vitro: evidence for follicle stimulating hormone-mediated contact inhibition of Sertoli cell mitosis. Biol Reprod 55(2):227-235.

Scobey M J, Fix C A, Walker W H. The Id2 transcriptional repressor Is induced by olliclestimulating hormone and cAMP. J Biol Chem 2004; 279: 16064-16070.

Sharpe R M, McKinnell C, Kivlin C, Fisher J S. 2003. Proliferation and functional maturation of Sertoli cells, and their relevance to disorders of testis function in adulthood. Reproduction 125(6):769-784.

Sharpe R M, Walker M, Millar M R, Atanassova N, Morris K, McKinnell C, Saunders P T, Fraser H M. 2000. Effect of neonatal gonadotropin-releasing hormone antagonist administration on sertoli cell number and testicular development in the marmoset: comparison with the rat. Biol Reprod 62(6):1685-1693.

Shima J E, McLean D J, McCarrey J R, Griswold M D. The Murine Testicular Transcriptome: Characterizing Gene Expression in the Testis During the Progression of Spermatogenesis. Biol Reprod 2004; 71: 319-330.

Silva F R, Leite L D, Wassermann G F. 2002. Rapid signal transduction in Sertoli cells. Eur J Endocrinol 147(3):425-433.

Simoni M, Weinbauer G F, Gromoll J, Nieschlag E. 1999. Role of FSH in male gonadal function. Ann Endocrinol (Paris) 60(2):102-106.

Skinner M K, Fetterolf P M, Anthony C T. 1988. Purification of a paracrine factor, P-Mod-S, produced by testicular peritubular cells that modulates Sertoli cell function. J Biol Chem 263(6):2884-2890.

Stork P J, Schmitt J M. 2002. Crosstalk between cAMP and MAP kinase signaling in the regulation of cell proliferation. Trends Cell Biol 12(6):258-266.

Tabuchi Y, Takahashi R, Ueda M, Obinata M. 2003. Development of a conditionally immortalized testicular Sertoli cell line RTS3-3 from adult transgenic rats harboring temperature-sensitive simian virus 40 large T-antigen gene. Cell Struct Funct 28(1):87-95.

Takai N, Miyazaki T, Fujisawa K, Nasu K, Miyakawa I. 2001. Id1 expression is associated with histological grade and invasive behavior in endometrial carcinoma. Cancer Lett 165(2):185-193.

Tam S K, Gu W, Mahdavi V, Nadal-Ginard B. 1995. Cardiac myocyte terminal differentiation. Potential for cardiac regeneration. Ann N Y Acad Sci 752:72-79.

Tang J, Gordon G M, Nickoloff B J, Foreman K E. 2002. The helix-loop-helix protein id-1 delays onset of replicative senescence in human endothelial cells. Lab Invest 82(8):1073-1079.

Tung P S, Skinner M K, Fritz I B. 1984. Fibronectin synthesis is a marker for peritubular cell contaminants in Sertoli cell-enriched cultures. Biol Reprod 30(1):199-211.

Turlejski K, Djavadian R. 2002. Life-long stability of neurons: a century of research on neurogenesis, neuronal death and neuron quantification in adult CNS. Prog Brain Res 136:39-65.

Walker W H. 2003. Molecular mechanisms controlling Sertoli cell proliferation and differentiation. Endocrinology 144(9):3719-3721.

Walker W H, Fucci L, Habener J F. 1995. Expression of the gene encoding transcription factor cyclic adenosine 3',5'-monophosphate (cAMP) response element-binding protein (CREB): regulation by follicle-stimulating hormone induced cAMP signaling in primary rat Sertoli cells. Endocrinology 136(8):3534-3545.

Walther N, Jansen M, Ergun S, Kascheike B, Ivell R. 1996. Sertoli cell lines established from H-2Kb-tsA58 transgenic mice differentially regulate the expression of cell-specific genes. Exp Cell Res 225(2):411-421.

Wegner M. 2001. Expression of transcription factors during oligodendroglial development. Microsc Res Tech 52(6):746-752.

Wei Q, Paterson B M. 2001. Regulation of MyoD function in the dividing myoblast. FEBS Lett 490(3):171-178.

Wilson J W, Deed R W, Inoue T, Balzi M, Becciolini A, Faraoni P, Potten C S, Norton J D. 2001. Expression of Id helix-loop-helix proteins in colorectal adenocarcinoma correlates with p53 expression and mitotic index. Cancer Res 61(24):8803-8810.

Yokota Y, Mori S. 2002. Role of Id family proteins in growth control. J Cell Physiol 190(1):21-28.

Yomogida K, Ohtani H, Harigae H, Ito E, Nishimune Y, Engel J D, Yamamoto M. 1994. Developmental stage- and spermatogenic cycle-specific expression of transcription factor GATA-1 in mouse Sertoli cells. Development 120(7):1759 1766.

Yoshikawa K. 2000. Cell cycle regulators in neural stem cells and postmitotic neurons. Neurosci Res 37(1):1-14.

Zebedee Z, Hara E. 2001. Id proteins in cell cycle control and cellular senescence. Oncogene 20(58):8317-8325.

Zheng W, Wang H, Xue L, Zhang Z, Tong T. Regulation of cellular senescence and p16(INK4a) expression by Id1 and E47 proteins in human diploid fibroblast. J Biol Chem 2004; 279: 31524-31532.

What is claimed is:

1. An isolated modified mammalian cell comprising a stably integrated introduced gene sequence, which stably expresses a protein which binds a basic helix-loop-helix (bHLH) protein, wherein the stably integrated introduced gene sequence is integrated into the cell genome, wherein the cell is a proliferating non-tumorigenic Sertoli cell and was post-mitotic prior to stable integration of the introduced gene sequence into the cell genome, wherein the protein is an Inhibitor of differentiation (Id) protein.

2. The modified cell of claim 1, which is selected from the group consisting of a differentiating cell and differentiated cell.

3. The modified cell of claim 1, wherein the Id protein is Id1, Id2, Id3, or Id4.

* * * * *